United States Patent
Birnbaum et al.

(10) Patent No.: US 11,846,639 B2
(45) Date of Patent: *Dec. 19, 2023

(54) LIGAND DISCOVERY FOR T CELL RECEPTORS

(71) Applicants: THE BOARD OF TRUSTEES OF THE LELAND STANFORD JUNIOR UNIVERSITY, Stanford, CA (US); CALIFORNIA INSTITUTE OF TECHNOLOGY, Pasadena, CA (US)

(72) Inventors: Michael Edward Birnbaum, Stanford, CA (US); Juan Luis Mendoza, Redwood City, CA (US); Michael Thomas Bethune, Pasadena, CA (US); David Baltimore, Pasadena, CA (US); Kenan Christopher Garcia, Menlo Park, CA (US)

(73) Assignees: The Board of Trustees of the Leland Stanford Junior University, Stanford, CA (US); CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/378,310

(22) Filed: Jul. 16, 2021

(65) Prior Publication Data
US 2022/0229067 A1    Jul. 21, 2022

Related U.S. Application Data

(63) Continuation of application No. 17/011,911, filed on Sep. 3, 2020, now Pat. No. 11,125,756, which is a continuation of application No. 15/301,930, filed as application No. PCT/US2015/024244 on Apr. 3, 2015, now Pat. No. 10,816,554.

(60) Provisional application No. 61/975,646, filed on Apr. 4, 2014.

(51) Int. Cl.
*G01N 33/68* (2006.01)
*C07K 14/00* (2006.01)

(52) U.S. Cl.
CPC ......... *G01N 33/6845* (2013.01); *C07K 14/00* (2013.01); *G01N 2333/7051* (2013.01); *G01N 2333/70539* (2013.01)

(58) Field of Classification Search
None
See application file for complete search history.

(56) References Cited

U.S. PATENT DOCUMENTS

| | | |
|---|---|---|
| 5,567,809 A * | 10/1996 | Apple ............... C12Q 1/6881 536/24.31 |
| 6,300,065 B1 | 10/2001 | Kieke et al. |
| 6,406,863 B1 | 6/2002 | Zhu et al. |
| 6,410,246 B1 | 6/2002 | Zhu et al. |
| 6,410,271 B1 | 6/2002 | Zhu et al. |
| 6,423,538 B1 | 7/2002 | Wittrup et al. |
| 6,534,633 B1 * | 3/2003 | Weidanz ............ C07K 16/22 530/387.3 |
| 6,696,251 B1 | 2/2004 | Wittrup et al. |
| 6,699,658 B1 | 3/2004 | Wittrup et al. |
| 6,709,844 B1 | 3/2004 | Levy |
| 6,759,243 B2 | 7/2004 | Kranz et al. |
| 6,861,234 B1 | 3/2005 | Simard et al. |
| 6,977,074 B2 | 12/2005 | Kündig et al. |
| 6,994,851 B1 | 2/2006 | Kundig et al. |
| 7,232,682 B2 | 6/2007 | Simard et al. |
| 7,364,729 B2 | 4/2008 | Kündig et al. |
| 7,378,234 B2 | 5/2008 | Buschle et al. |
| 7,390,654 B2 | 6/2008 | Levy |
| 7,465,787 B2 | 12/2008 | Wittrup et al. |
| 7,528,223 B2 | 5/2009 | Mattner et al. |
| 7,569,357 B2 | 8/2009 | Kranz et al. |
| 7,704,514 B2 | 4/2010 | Buschle et al. |
| 8,252,916 B2 | 8/2012 | Simard et al. |
| 8,277,815 B2 | 10/2012 | Buschle et al. |
| 8,313,894 B2 | 11/2012 | Flechtner et al. |
| 8,372,393 B2 | 2/2013 | Kündig et al. |
| 8,372,636 B2 | 2/2013 | Wittrup et al. |
| 8,450,247 B2 | 5/2013 | Peelle et al. |
| 8,637,305 B2 | 1/2014 | Simard et al. |
| 8,741,576 B2 | 6/2014 | Tangri et al. |
| 8,784,837 B2 | 7/2014 | Buschle et al. |
| 8,916,340 B2 | 12/2014 | Sadegh-Nasseri |
| 9,005,927 B2 | 4/2015 | Hufton et al. |
| 9,012,181 B2 | 4/2015 | Hufton et al. |
| 9,034,601 B2 | 5/2015 | Hufton et al. |
| 9,040,258 B2 | 5/2015 | Hufton et al. |
| 9,045,791 B2 | 6/2015 | Flechtner et al. |
| 9,068,980 B2 | 6/2015 | Hufton et al. |

(Continued)

FOREIGN PATENT DOCUMENTS

| | | |
|---|---|---|
| WO | WO 2004/015395 | 2/2004 |
| WO | WO 2009/106073 | 9/2009 |
| WO | WO 2012/022975 | 2/2012 |

OTHER PUBLICATIONS

Zhu et al (Eur. J. Immunol. 27:1933-41) (Year: 1997).*

(Continued)

*Primary Examiner* — Christopher M Gross
(74) *Attorney, Agent, or Firm* — Pamela J. Sherwood; Bozicevic, Field & Francis LLP

(57) ABSTRACT

Compositions and methods are provided for the identification of peptide sequences that are ligands for a T cell receptor (TCR) of interest, in a given MHC context.

15 Claims, 36 Drawing Sheets

Specification includes a Sequence Listing.

(56) References Cited

U.S. PATENT DOCUMENTS

| | | |
|---|---|---|
| 9,116,149 B2 | 8/2015 | Hufton et al. |
| 9,139,637 B2 | 9/2015 | Wittrup et al. |
| 9,488,645 B2 | 11/2016 | Rong et al. |
| 9,556,428 B2 | 1/2017 | Hufton et al. |
| 9,873,870 B2 | 1/2018 | Flechtner et al. |
| 10,059,936 B2 | 8/2018 | Hufton et al. |
| 11,125,756 B2 * | 9/2021 | Birnbaum ............... C07K 14/00 |
| 2002/0081579 A1 | 6/2002 | Skeiky et al. |
| 2002/0165149 A1 | 11/2002 | Kranz et al. |
| 2003/0003650 A1 | 1/2003 | Song |
| 2003/0036506 A1 | 2/2003 | Kranz et al. |
| 2004/0072246 A1 | 4/2004 | Martin et al. |
| 2006/0051358 A1 | 3/2006 | Banchereau et al. |
| 2007/0054262 A1 | 3/2007 | Baker et al. |
| 2008/0219947 A1 * | 9/2008 | Linette ............. C07K 14/70539 435/325 |
| 2010/0210473 A1 | 8/2010 | Bowley et al. |
| 2014/0242101 A1 | 8/2014 | Andersen |
| 2017/0051036 A1 | 2/2017 | Jakobsen et al. |
| 2018/0052176 A1 | 2/2018 | Holt et al. |

OTHER PUBLICATIONS

Wen et al (Methods in molecular biology 1061:245-64) (Year: 2013).*

Wen et al (J. Immunological Methods 3:37-33) (Year: 2008).*

Adams et al., "T cell receptor signaling is limited by docking geometry to peptide-major histocompatibility complex," Immunity, Nov. 23, 2011, 35(5):681-693, doi:10.1016/j.immuni.2011.09.013.

Birnbaum et al., "Diversity-oriented approaches for interrogating T-cell receptor repertoire, ligand recognition, and function," Immunol Rev, Nov. 2012, 250(1):82-101, doi:10.1111/imr.12006.

Brophy et al., "A yeast display system for engineering functional peptide-MHC complexes," J Immunol Methods, 2003, 272:235-346.

Dudley et al., "Full-length novel MHC class I allele discovery by next-generation sequencing: two platforms are better than one," Immunogenetics, Jan. 2014, 66(1):15-24.

Mitaksov et al., "Structural engineering of pMHC reagents for T Cell vaccines and diagnosics," Chemy Biol, 2007, 14:909-922.

International Search Report dated Jul. 27, 2015 in PCT/US2015/024244.

* cited by examiner

Figure 1 (Cont. 1)
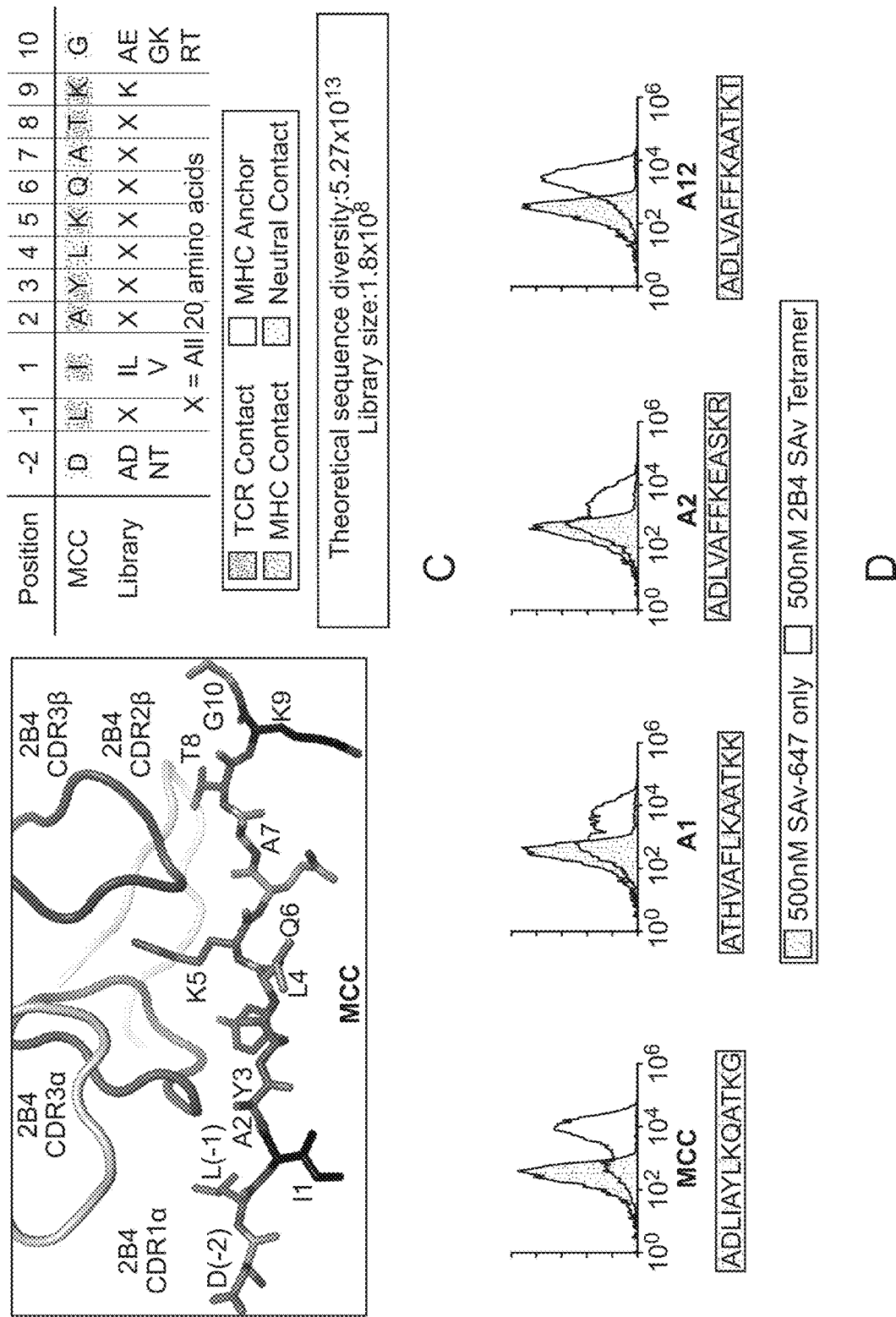

A

Figure 2 (Cont. 1)
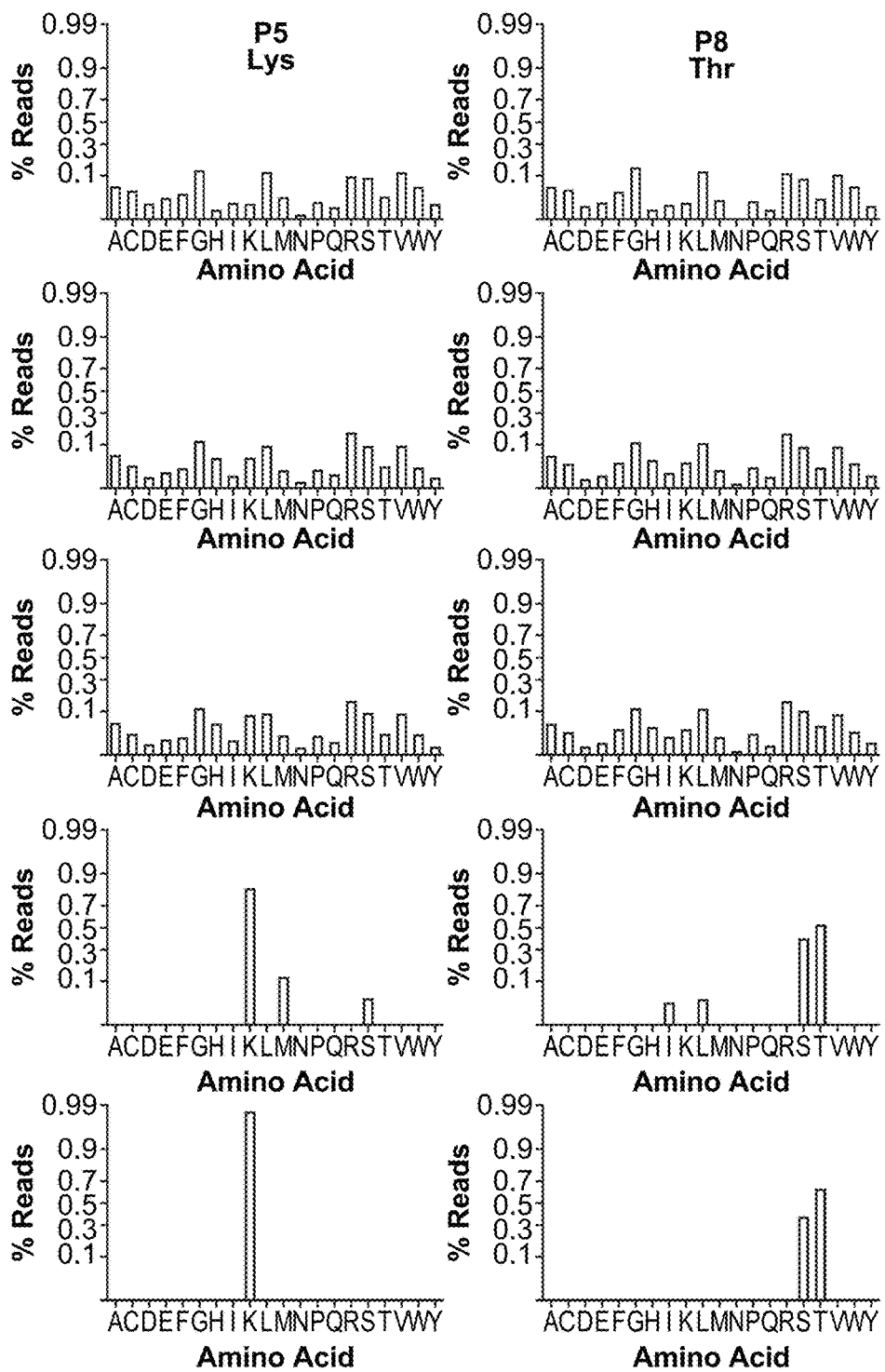
A

Figure 2 (Cont. 2)
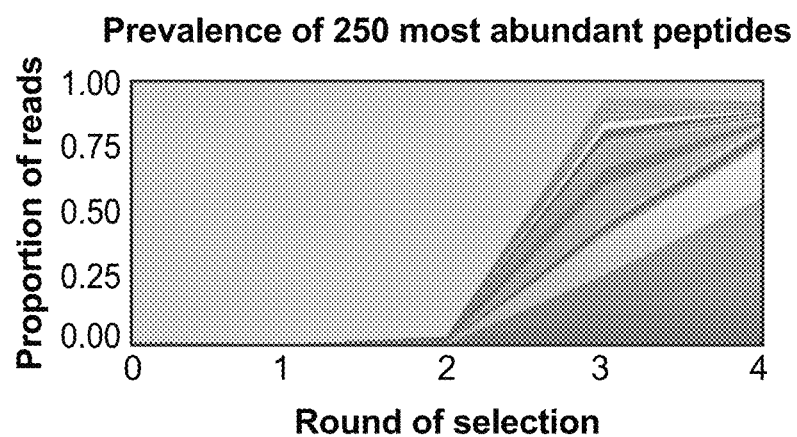
B
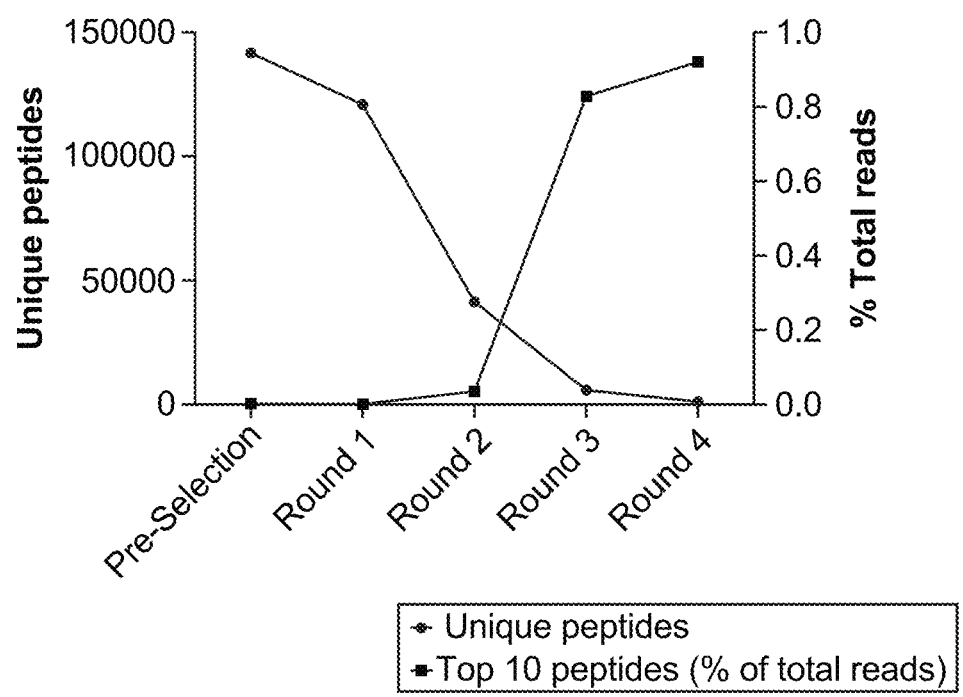
C

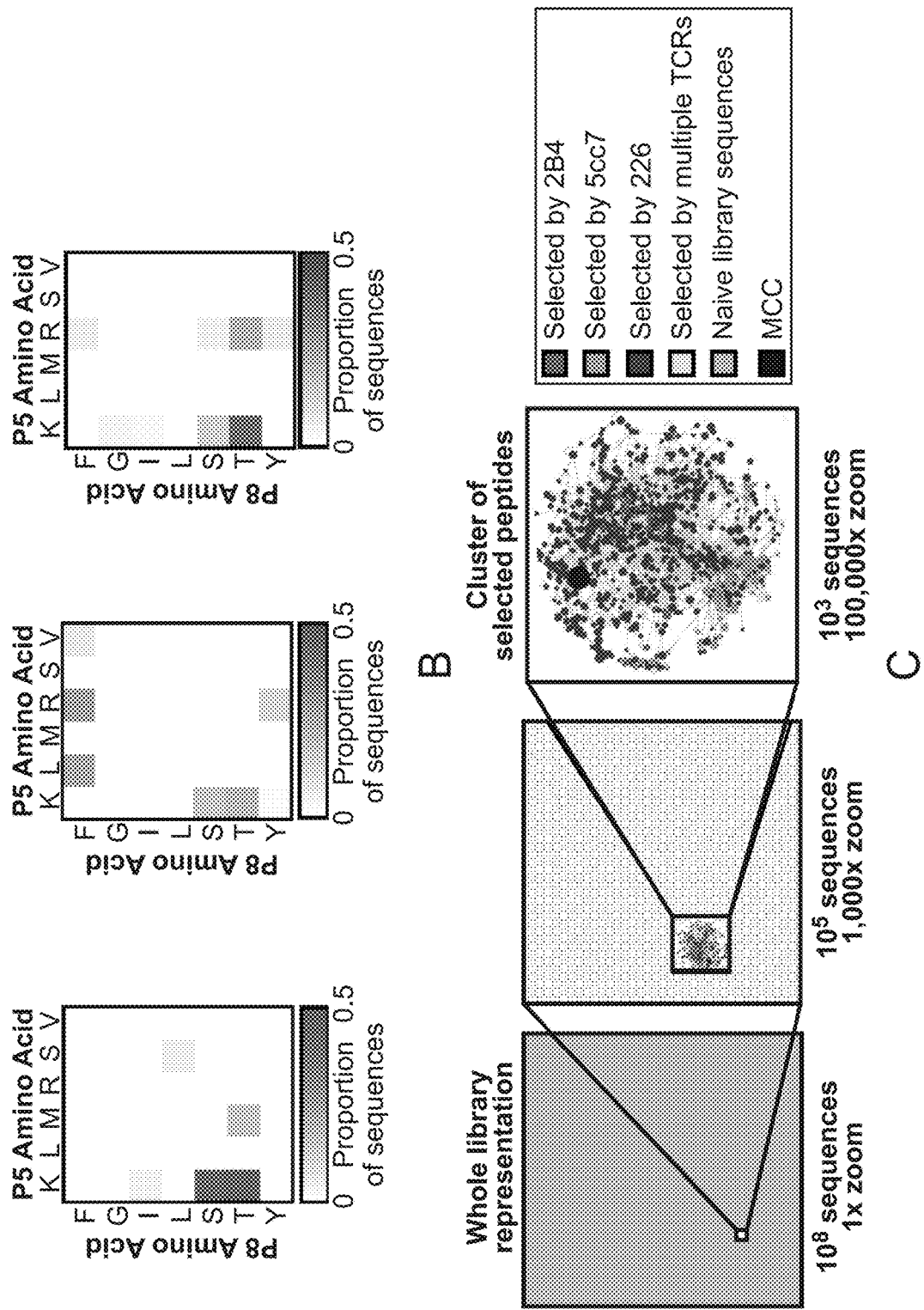
Figure 3 (Cont. 1)

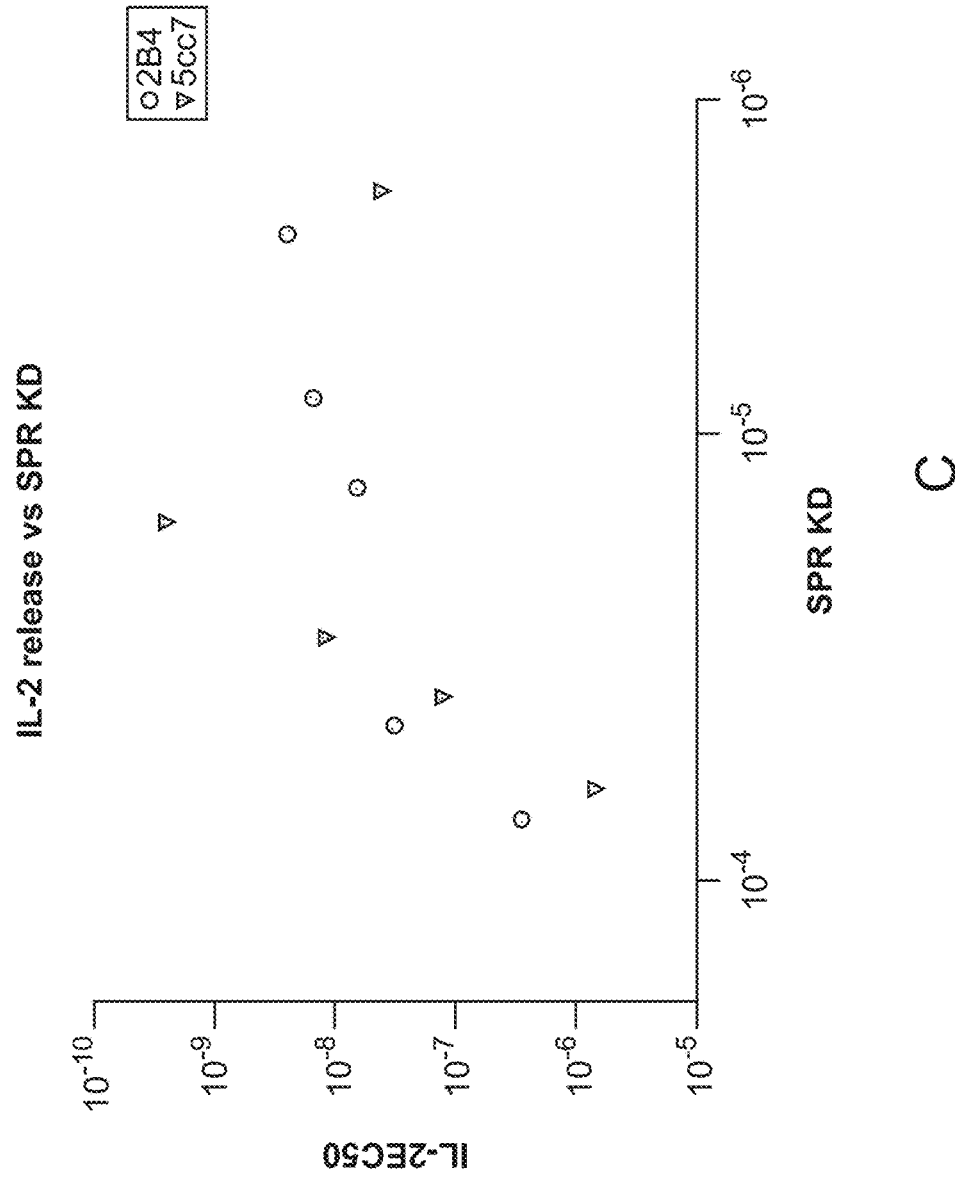

Figure 5 (Cont. 1)
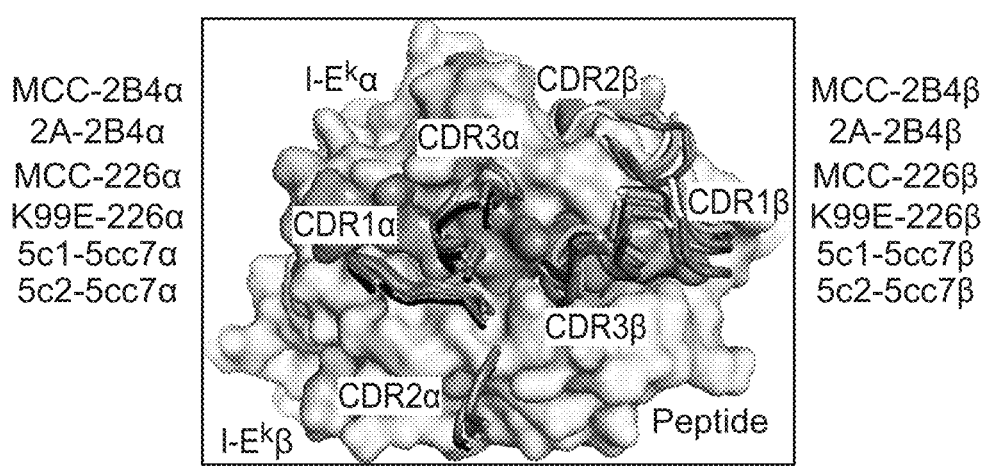
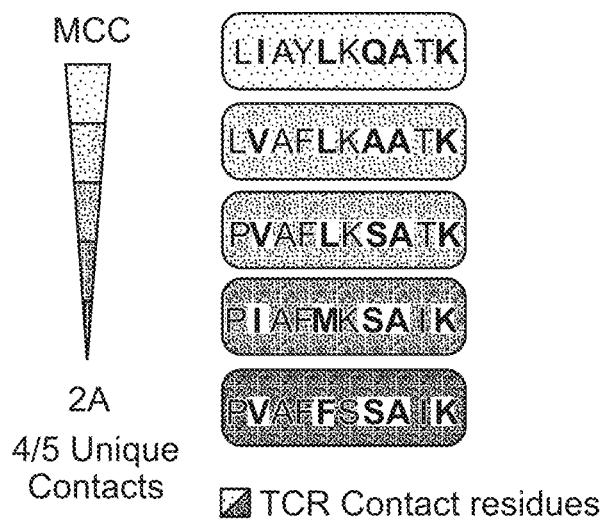

Figure 6
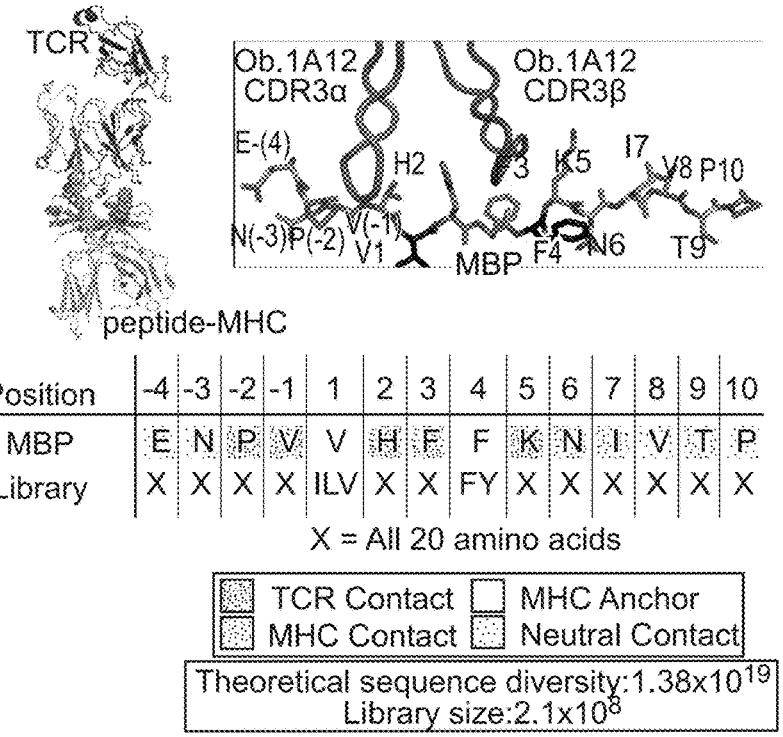
A
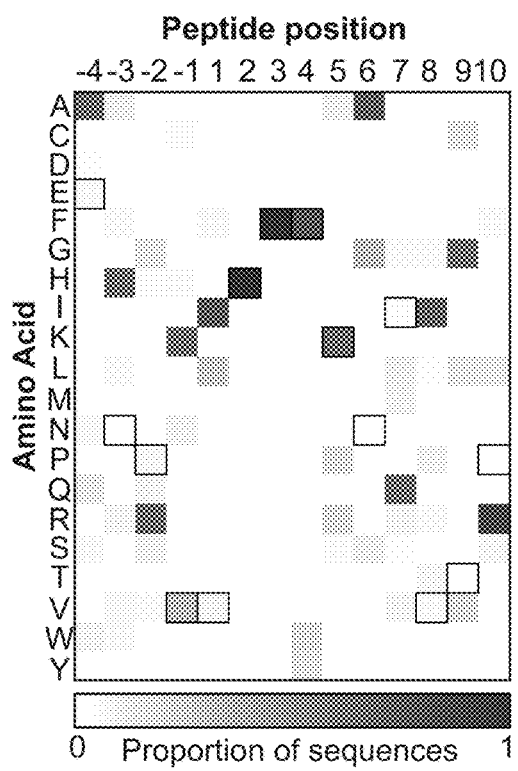
B

Figure 6 (Cont. 1)
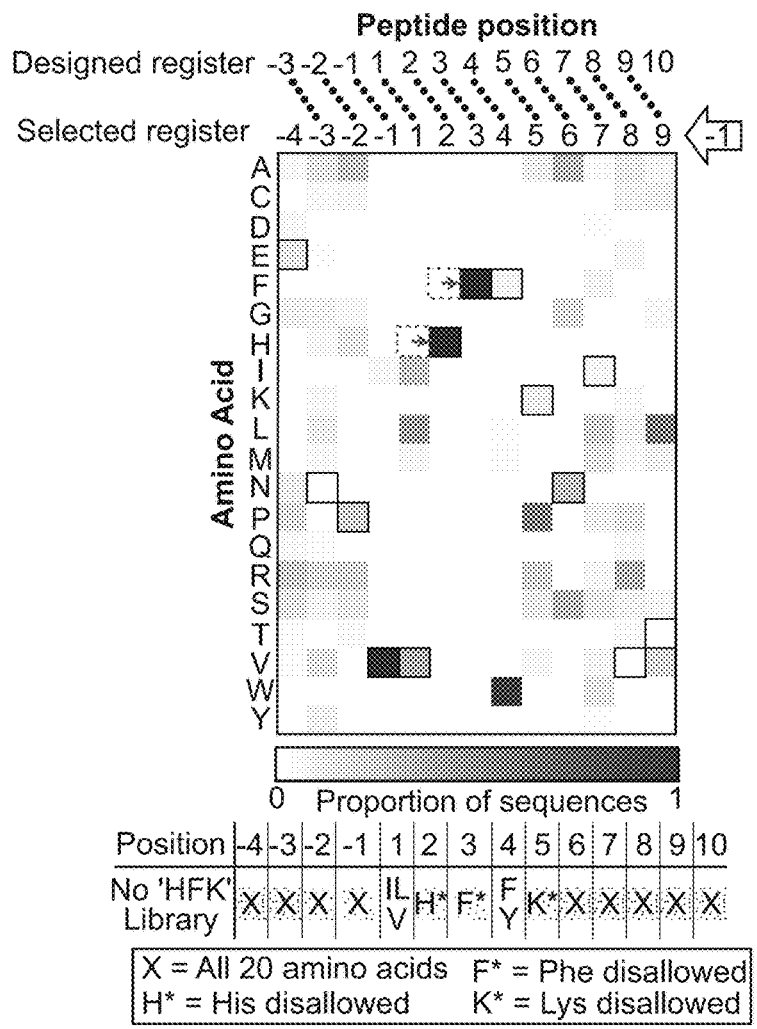
C
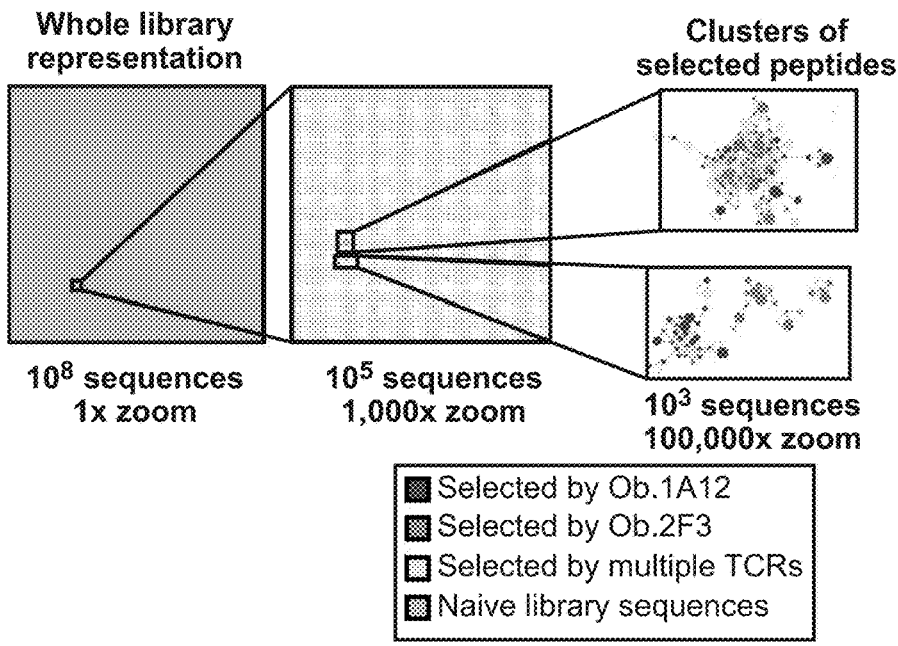
D

A

Figure 7 (Cont. 1)
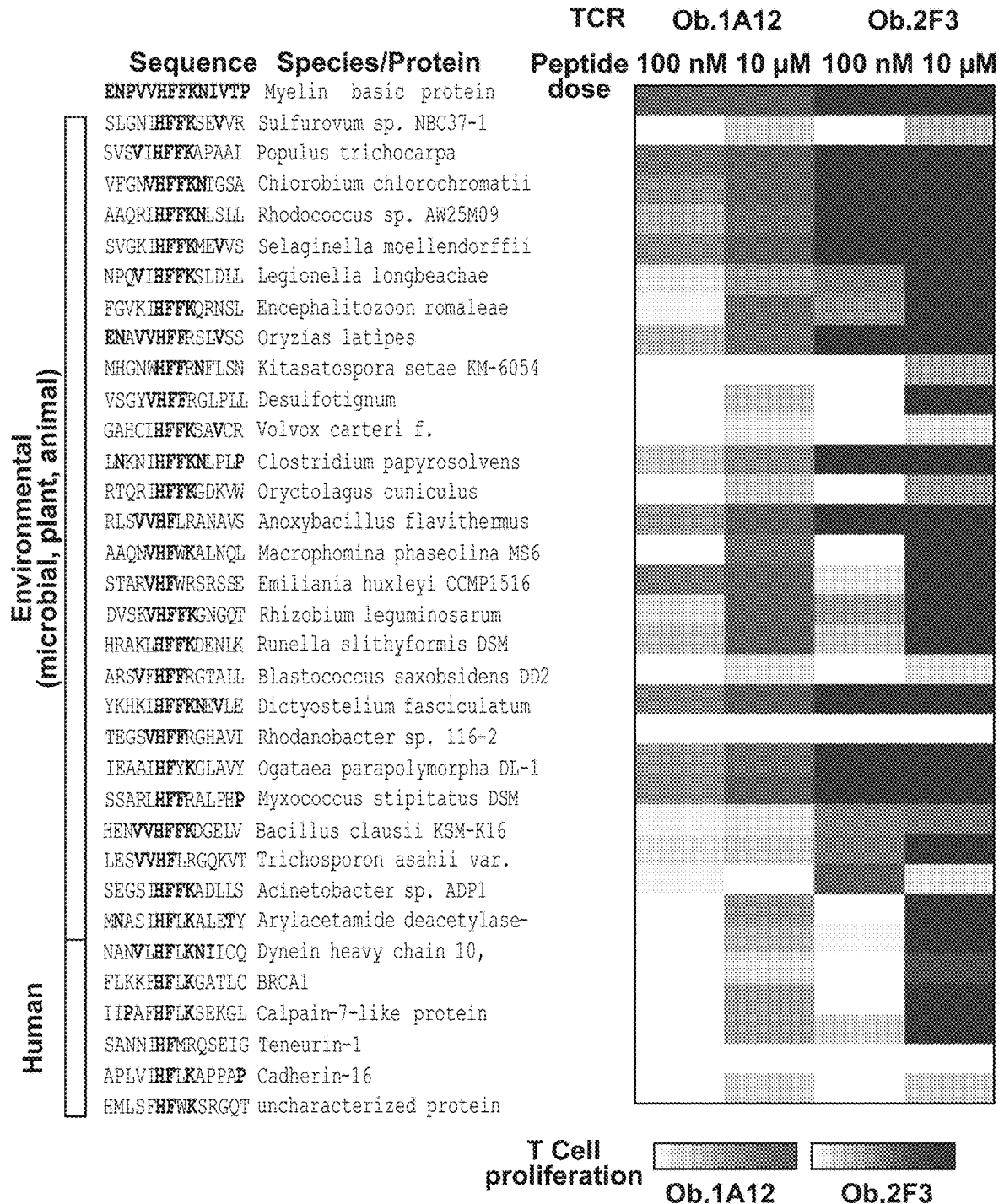
B

Figure 9

2B4 I-E$^k$ Deep sequencing

| Selection round | Total sequences | Corrected sequences | Unique peptide | % of 40 most abundant peptides | Corrected Unique peptides† |
|---|---|---|---|---|---|
| 0 | 287733 | 168895 | 132464 | 0.3 | |
| 1 | 264945 | 180366 | 115616 | 0.4 | |
| 2 | 168404 | 116762 | 39564 | 5.2 | 3010 |
| 3 | 377095 | 325998 | 5655 | 92.70 | 207 |
| 4 | 168595 | 163185 | 1170 | 97.70 | 149 |

| Peptide | Rd 0 Reads | Rd 1 Reads | Rd 2 Reads | Rd 3 Reads | Rd 4 Reads |
|---|---|---|---|---|---|
| ADLVAFFKEASKR | 32 | 19 | 407 | 44480 | 51187 |
| ATHVAFLKAATKK | 48 | 30 | 513 | 45157 | 48637 |
| AAQVAFLKAATKA | 28 | 27 | 731 | 48876 | 34095 |
| ATHVAFLKAATKA | 5 | 2 | 23 | 7129 | 4645 |
| AAQVAFLKAATKK | 3 | 3 | 32 | 6641 | 4331 |
| ADWVAFLKQATKG | 4 | 0 | 63 | 3085 | 2803 |
| ADLVAFFKEASKK | 0 | 0 | 5 | 1474 | 1473 |
| AAPVAFLKSASKT | 19 | 16 | 769 | 45760 | 1180 |
| ANGLAFFKSASKT | 15 | 8 | 257 | 19671 | 1144 |
| ATHVAFLKAATKR | 1 | 0 | 6 | 1117 | 1011 |
| ADLVAFLKAATKA | 1 | 1 | 4 | 871 | 860 |
| ADLVAFLKAATKK | 3 | 0 | 1 | 677 | 827 |
| ADGVAFFMSATKT | 4 | 12 | 473 | 32275 | 792 |
| ADLVAFFKEASKA | 1 | 0 | 2 | 1080 | 775 |
| ADLVAFLKAATKA | 0 | 0 | 4 | 833 | 695 |
| ATHVAFLKAASKR | 2 | 2 | 3 | 564 | 633 |
| ADLVAFFKAATKK | 0 | 0 | 1 | 598 | 565 |
| AAQVAFFKEASKR | 2 | 0 | 4 | 564 | 496 |
| ATHVAFLKEASKR | 2 | 0 | 3 | 415 | 380 |
| ATHVAFFKEASKR | 1 | 0 | 1 | 315 | 334 |
| ADLVAFFKEATKK | 0 | 1 | 3 | 286 | 331 |
| ADAIAFFSSSLKR | 8 | 2 | 236 | 11190 | 261 |
| ADPIAFMKSAIKK | 2 | 5 | 266 | 9138 | 242 |
| ADLVAFFKSASKT | 2 | 1 | 2 | 820 | 211 |
| ATHVAFLKAATKT | 2 | 1 | 4 | 1144 | 210 |

| TCR | Total sequences | Corrected Unique peptides |
|---|---|---|
| 5cc7 Rd3 | 1000609 | 897 |
| 226 Rd3 | 711890 | 303 |

| Peptide | Rd 0 Reads | Rd 1 Reads | Rd 2 Reads | Rd 3 Reads | Rd 4 Reads |
|---|---|---|---|---|---|
| | | 5c.c7 TCR reads | | | |
| ANGVAFFLTPFKA | 24 | 24 | 27277 | 201208 | 238583 |
| AAQVAFLKAATKA | 14 | 15 | 19721 | 148655 | 186297 |
| ADGVGFLKAASKR | 10 | 11 | 11984 | 99513 | 163019 |
| AAGVAFFRVPYKE | 1 | 4 | 4042 | 24818 | 38599 |
| ADGVGFFVSPFKK | 5 | 5 | 5795 | 42320 | 29621 |
| ADWIAYFRSPFFKG | 5 | 33 | 17265 | 129855 | 26895 |
| ADGLAYFRSSFKG | 5 | 9 | 10336 | 59971 | 9597 |
| ADLVGFFKTATKK | 2 | 3 | 2392 | 16250 | 6895 |
| ANLVAFFRSPYKA | 0 | 3 | 2978 | 19718 | 5394 |
| ADRLAYFLQPYKR | 0 | 0 | 1450 | 8898 | 5076 |
| | | 226 TCR reads | | | |
| AAQVAFLKAATKA | 14 | 34 | 8948 | 28248 | 54054 |
| ADLVAFFKEASKR | 13 | 22 | 7200 | 23036 | 40973 |
| ADKIAFFKSVTKK | 0 | 16 | 6980 | 18954 | 37810 |
| ANLLGYHKVPTKK | 1 | 36 | 9452 | 28169 | 26362 |
| ADPVAFFRSPFKT | 2 | 11 | 4229 | 9425 | 19895 |
| ATDIAFFRACTKG | 0 | 15 | 5172 | 13091 | 18423 |
| ANRIAWVKAATKT | 3 | 21 | 4887 | 12395 | 15334 |
| ADWVGWFKAATKG | 0 | 17 | 3291 | 9547 | 14181 |
| ADWIAYFRSPFKG | 5 | 12 | 3688 | 9735 | 13059 |
| ATYVAFSKSATKR | 0 | 2 | 2760 | 8177 | 12977 |

Figure 11
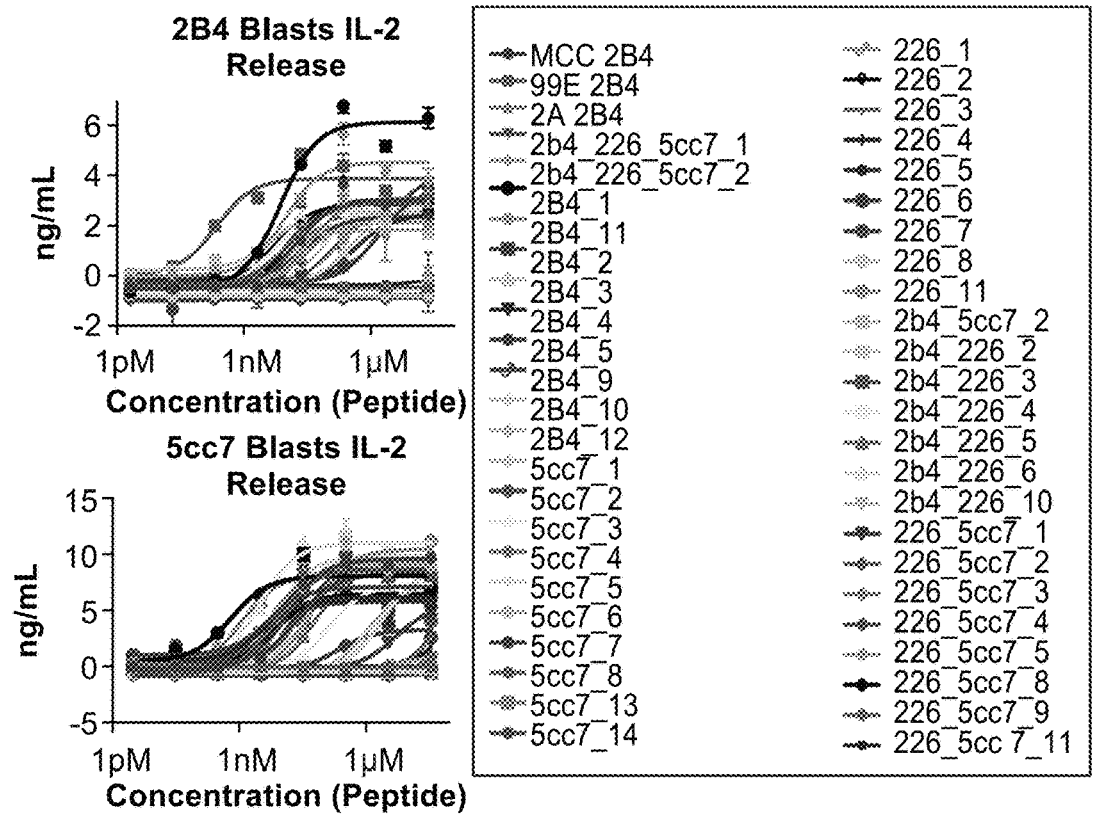
A
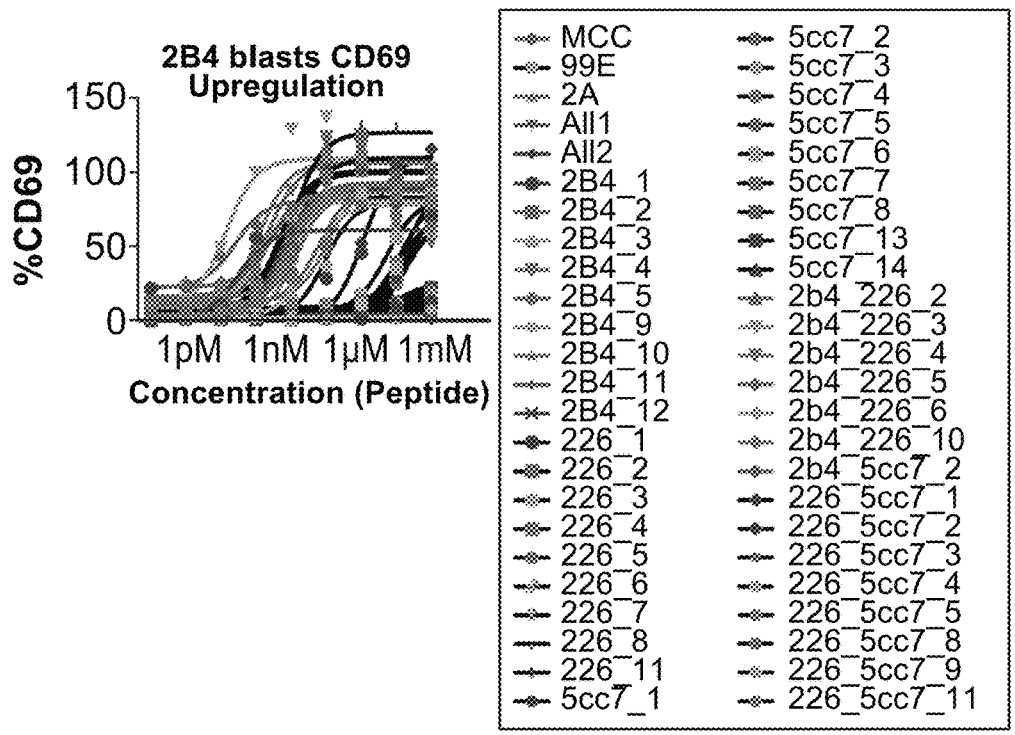
B

Figure 11 (Cont. 1)
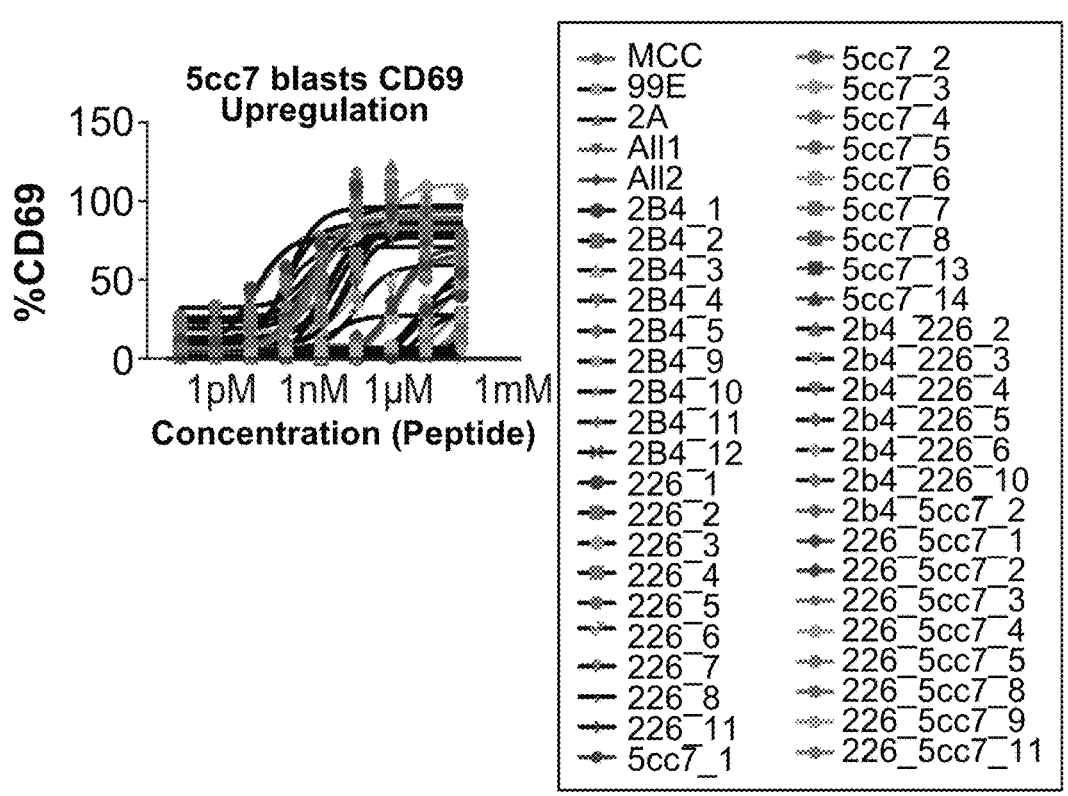
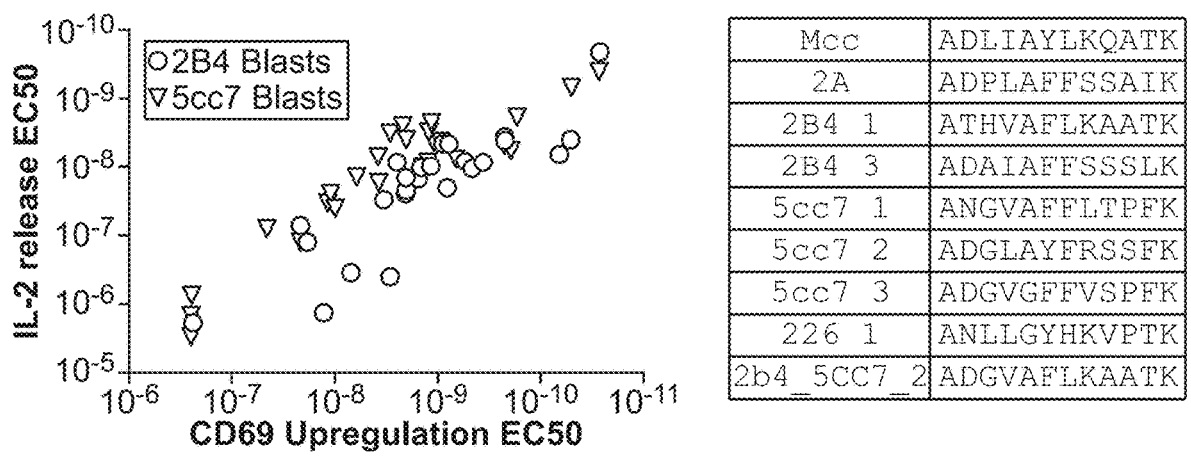

Figure 11 (Cont. 2)
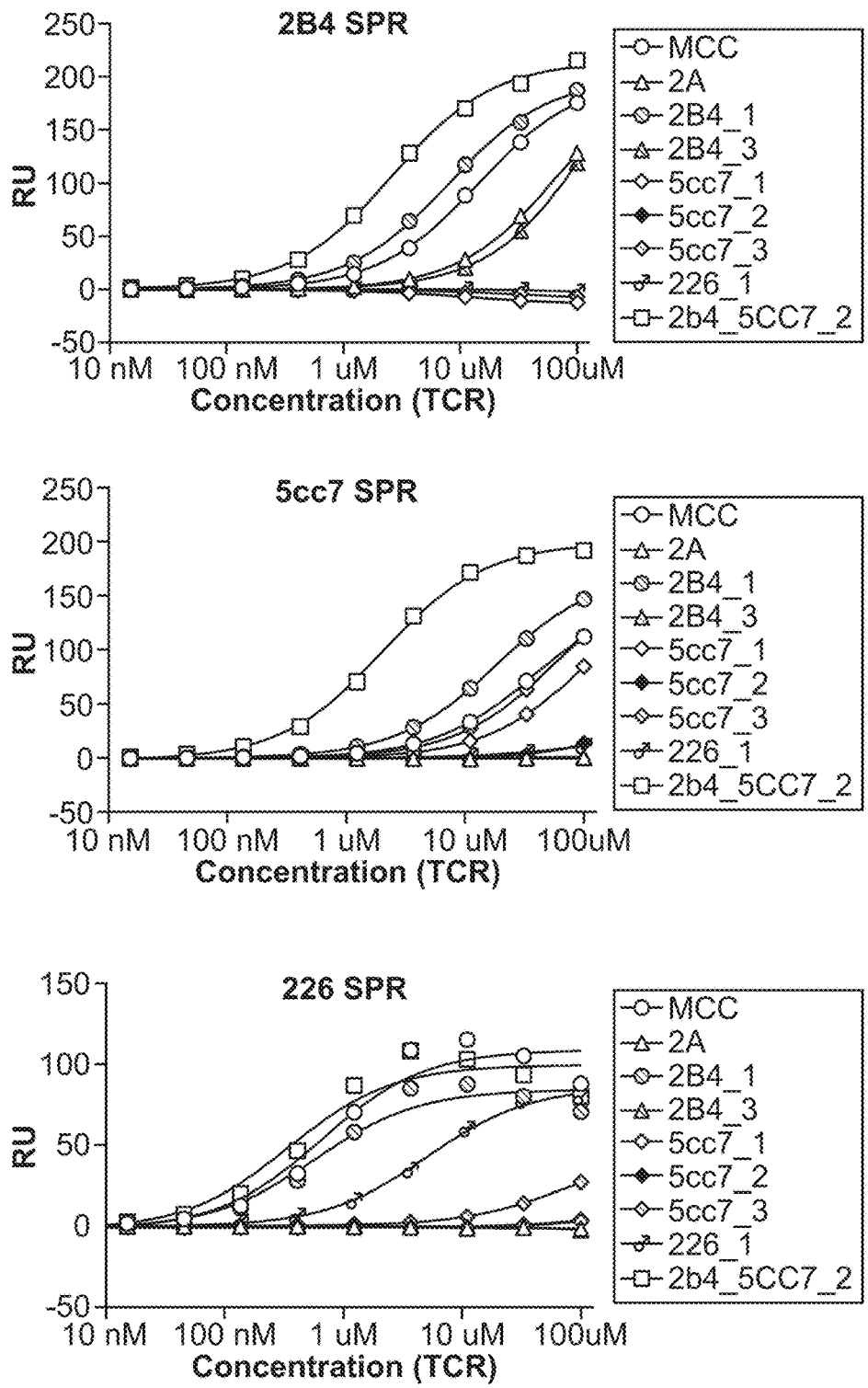
F

Figure 12
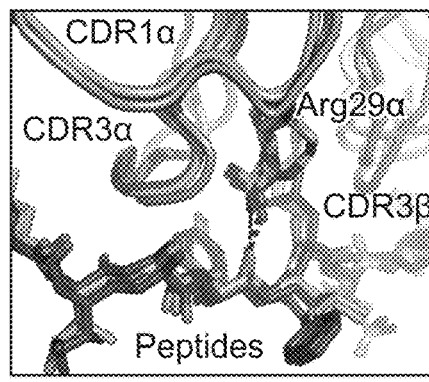
A
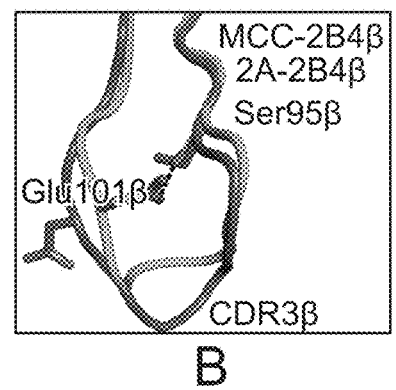
B
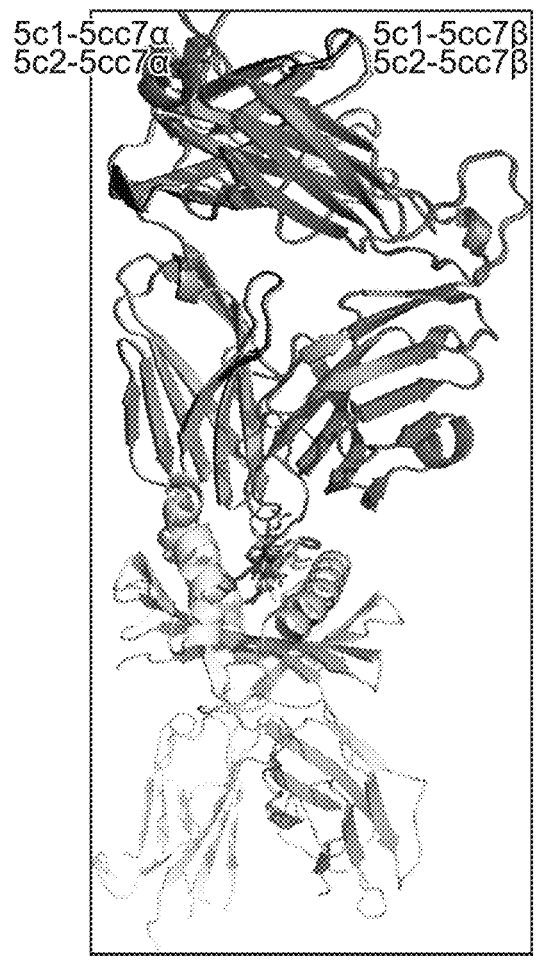
C
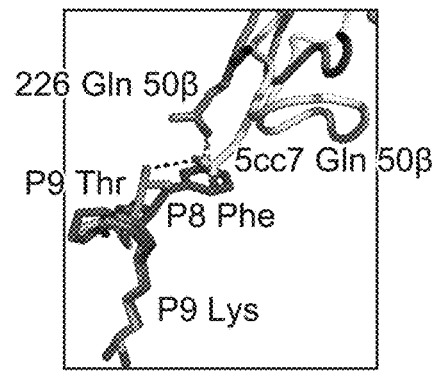
D
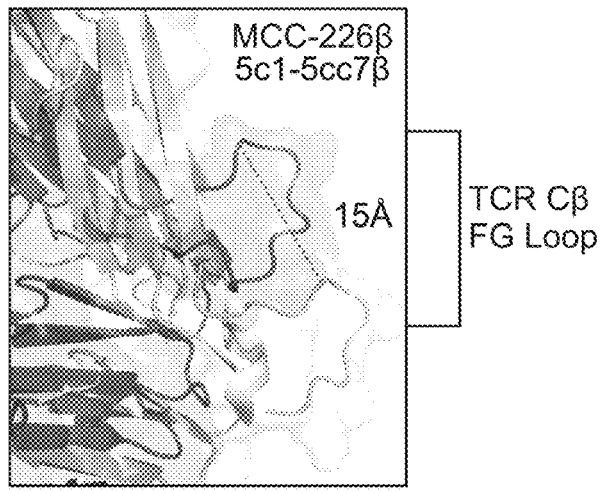
E

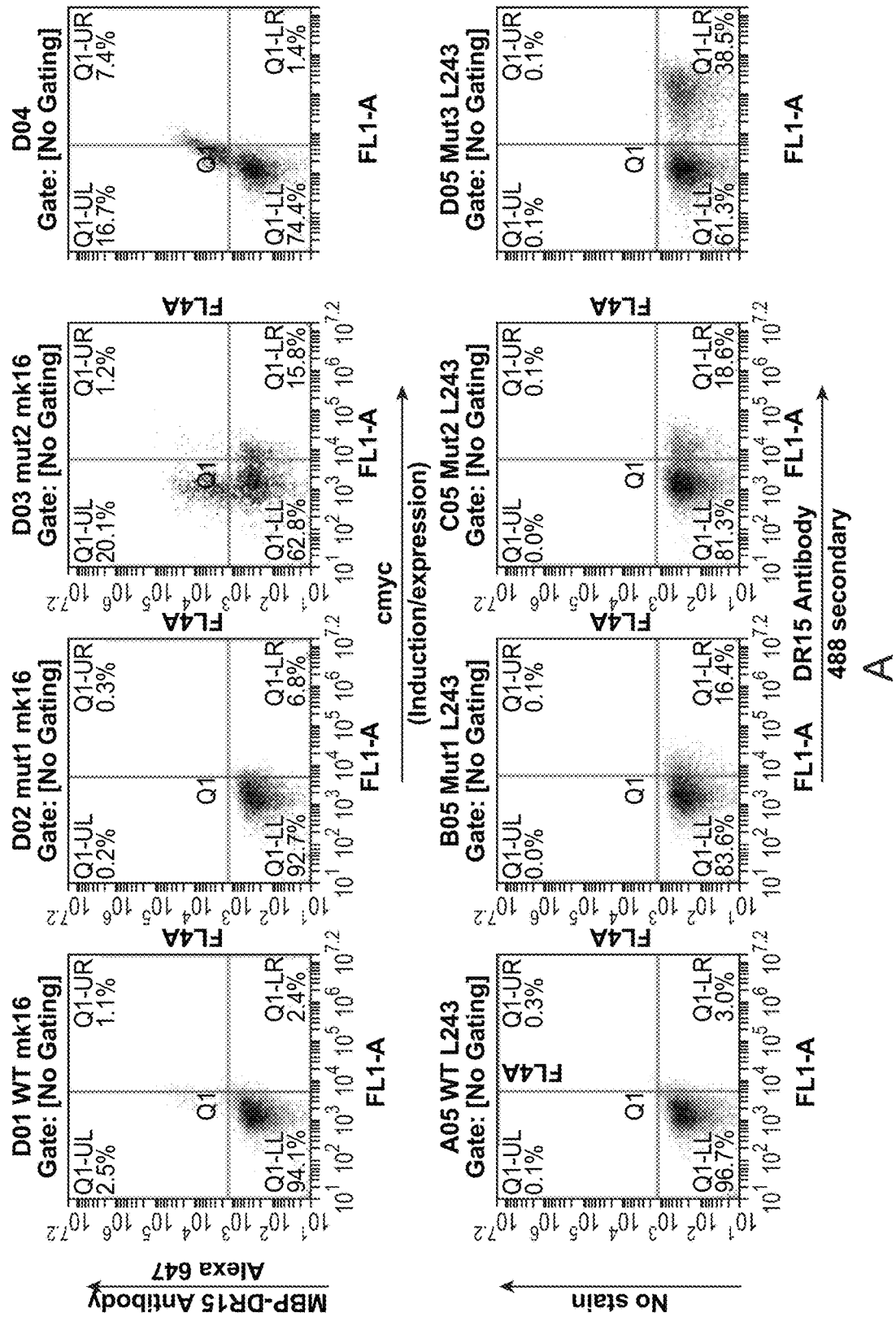
Figure 13 (Cont. 1)

Figure 13 (Cont. 2)
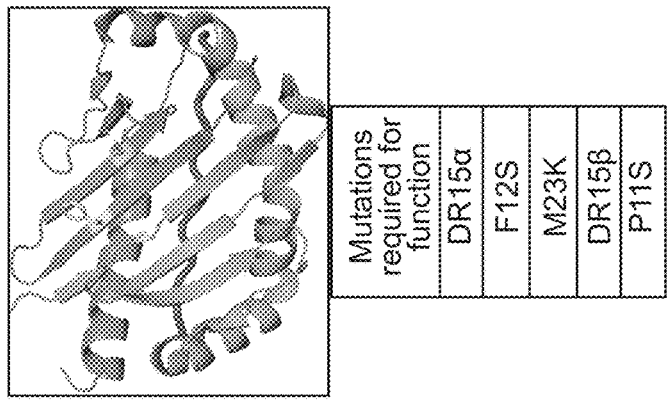
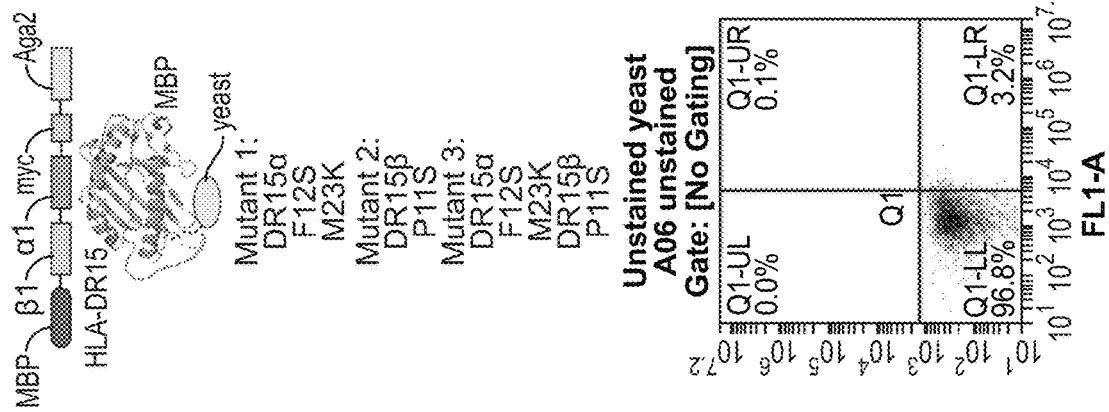

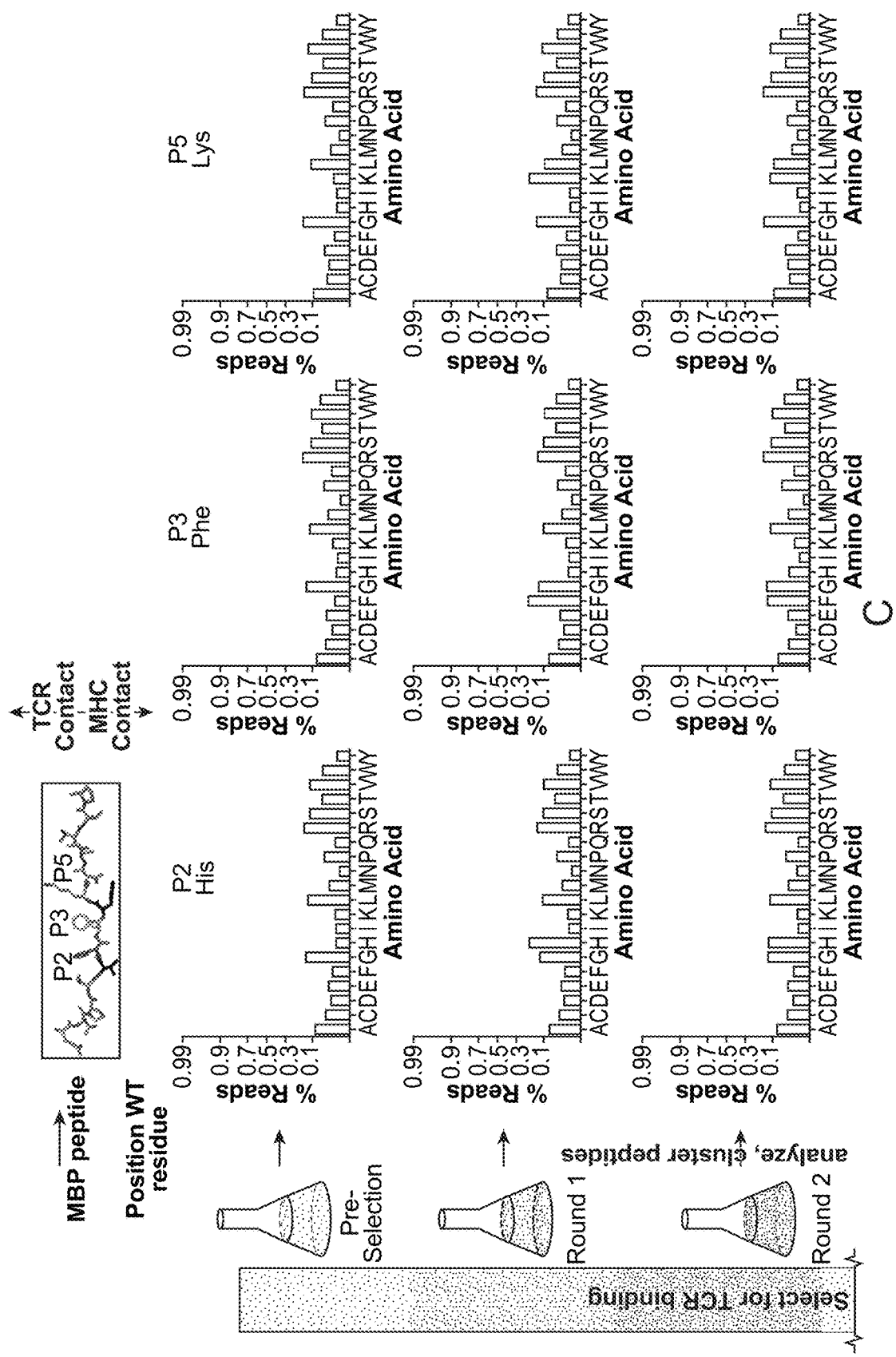
Figure 13 (Cont. 3)

Figure 13 (Cont. 4)
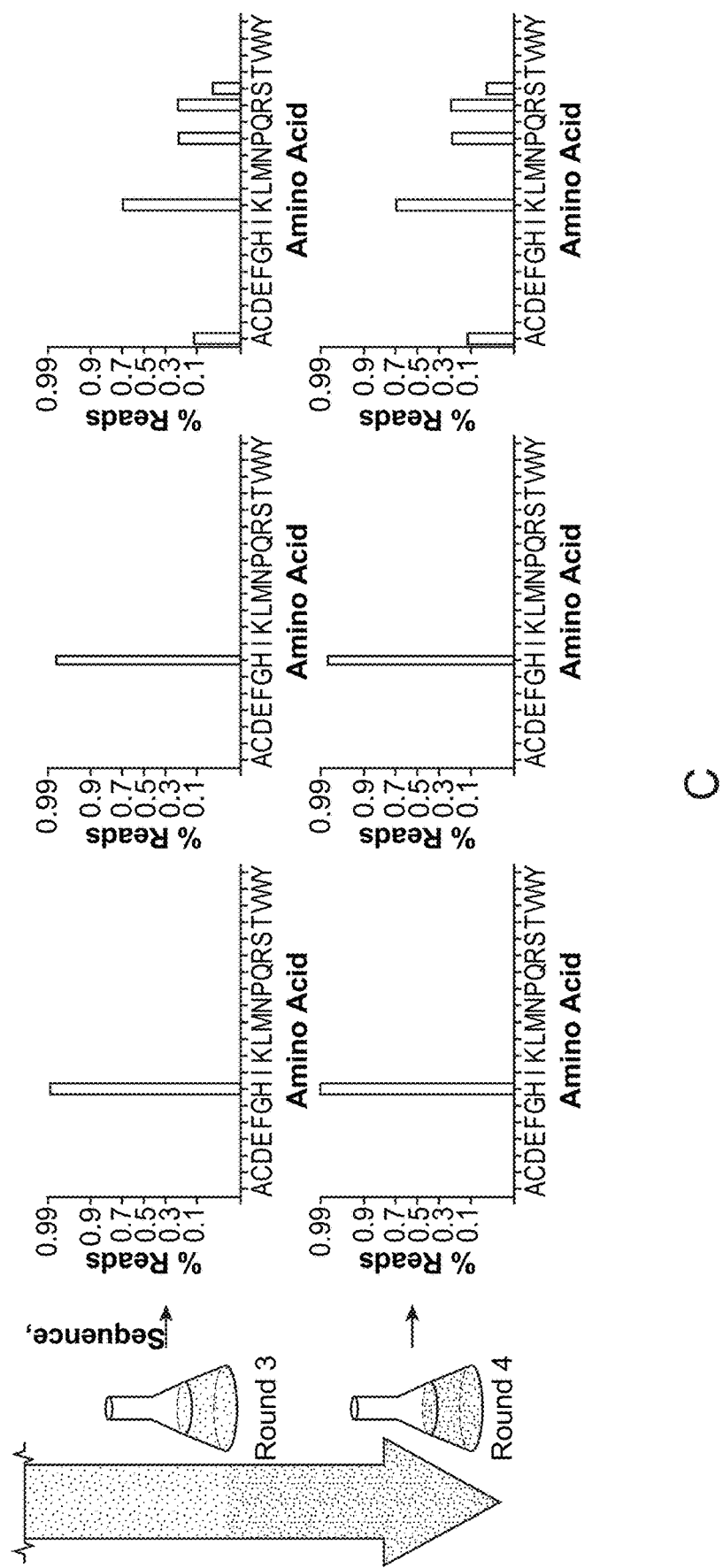

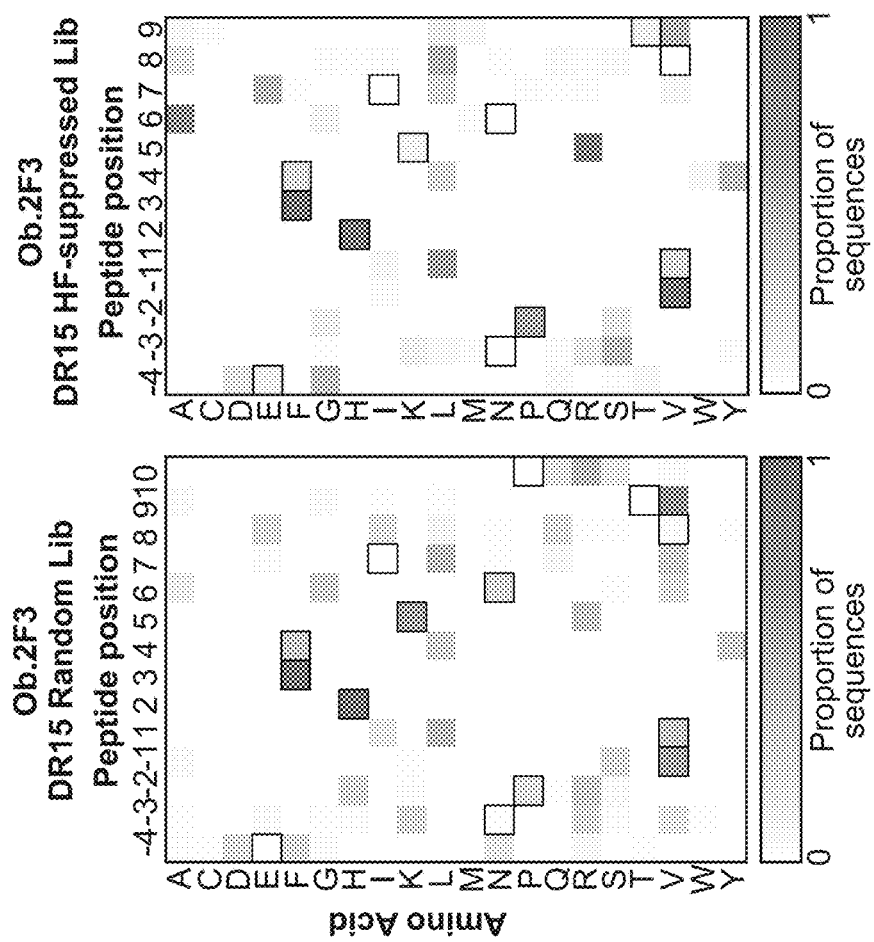
Figure 13 (Cont. 5)

HLA-A2
SEQ ID NO:1
ELAGIGILTVGGGGSGGGGSGGGGSIQRTPKIQVYSRHPAENGKSNFLNCYVSGFHPSDIEVDLLKNGERIEKVEHSDLSFSKDWSFYLLYYTEFTPTEKDEY
ACRVNHVTLSQPKIVKWDRDMGGGGSGGGGSGGGGSHSMRYFFTSVSRPGRGEPRFIAVGYVDDTQFVRFDSDAASQRMEPRAPWIEQEGPEYW
DGETRKVKAHSQTHRVDLGTLRGAYNQSEAGSHTVQRMYGCDVGSDWRFLRGYHQYAYDGKDYIALKEDLRSWTAADMAAQTTKHKWEAAHVAEQL
RAYLEGTCVEWLRRYLENGKETLQRTDAPKTHMTHHAVSDHEATLRCWALSFYPAEITLTWQRDGEDQTQDTELVETRPAGDRTFQKWAAVVVPSGQ
EQRYTCHVQHEGLPKPLTLRWEPSS
Peptide
β2-Microglobulin
MHC α1-α3

**HLA-B57*03**
SEQ ID NO:2
KAFSPEVIPMFGGGGSGGGGSGGGGSIQRTPKIQVYSRHPAENGKSNFLNCYVSGFHPSDIEVDLLKNGERIEKVEHSDLSFSKDWSFYLLYYTEFTPTEKDE
YACRVNHVTLSQPKIVKWDRDMGGGGSGGGGSGGGGSHSMRYFYTAMSRPGRGEPRFIAVGYVDDTQFVRFDSDAASPRMAPRAPWIEQEGPEY
WDGETRNMKASAQTYRENLRIALRAYNQSEAGSHIQVMYGCDVGPDGRLLRGHNQYAYDGKDYIALNEDLSSWTAADTAAQITQRKWEAARVAEQLR
AYLEGLCVEWLRRYLENGKETLQRADPPKTHVTHHPISDHEATLRCWALGFYPAEITLTWQRDGEDQTQDTELVETRPAGDRTFQKWAAVVVPSGEEQ
RYTCHVQHEGLPKPLTLRWEPSS
Peptide
β2-Microglobulin
MHC α1-α3

HLA-DR15
SEQ ID NO:3
ENPVVHFFKNIVTPRGGGGSGGGGSGGGGSGGDTRPRFLVQSKRECHFFNGTERVRFLDRYFYNQEESVRFDSDVGEFRAVTELGRPDAEYWNSQKDILEQ
ARAAVDTYCRHNYGVVESFTVQRRVQGGGGSGGGGIKEEHVIIQAEYLNPDQSGEFKFDFDGDEIFHVDMAKKETVWRLEEFGRFASFEAQGALANIAVD
KANLEIMTKRSNYTPIT
Peptide
MHC β1
MHC α1

Figure 15 (Cont. 1)

H-2L^d
SEQ ID NO 4
QLSPFPFDLGGGGSGGGGSSYIALNEDLRTWTAIDMAAQITRRKWEQAGAAEYYRAYLEGECVEWLHRYLKNGNATLLGGGGSGGGGPHSMRYFETA
VSRPGLGEPRYISVGYVDDKEFVRFDSDAENPRYEPQVPWMEQEGPEYWERITQIAKGQEQWFRVNLRTLLGAYNQSAGGTHTLQWMYGCDVGSDGRL
LRGYEQFAYDG
Peptide
MHC α2
MHC α1

I-E^k
SEQ ID NO 5
ADLIAYLKQATKGGGGSGGGGSGGGGSGRPSFTEYCKSECHFYNGTQRVRLLVRYFYNSEENLRFDSDVGEFRAVTELGRPDAENWNSQPEFLEQKRAEVD
TVCRHNYEIFDNFLVPRRVEGGGSGGGGIKEEHTIQAESYILPDKRGEFMFDFDGDEIFHVDIEKSETIWRLEEFAKFASFEVQGALANIAVDKANLDV
MKERSNNTPDA
Peptide
MHC β1
MHC α1

HLA-DR4
SEQ ID NO 6
MQLLRCFSIFSVIASVLAIKEEHVIQAEFYLNPDQSGEFMFDFDGDEIFHVDLAKKETVWRLEEFGRFASFEAQGALANIAVDKANLEIMTKRSNYTPITNV
PPEVTVLTNSPVELREPNVLICFIDKFTPPVVNVTWLRNGKPVTTGMSETVFLPREDHLFRKFHYLPFLPSTEDVYDCRVEHWGLDEPLLKHWEFDAPSP
LPETTEGGSGYPYDYAGSGATNFSLLKQAGDVEENPGPMQLLRCFSIFSVIASVLAFSWGAEGQRPGFGFGGGSGGGSGGGDTRPRFLEQVK
HECHFFNGTERVRFLDRYFYNQEEYVRFDSEVGEYRAVTELGRPDAEYWNSQKDLLEQKRAAVDTYCRHNYGVGESFTVQRRVYPEVTVYPAKTQPLQ
HHNLLVCSVNGFYPGSIEVRWFRNGQEEKTGVVSTGLIQNGDWTFQTLVMLETVPRSGEVYTCQVEHPSLTSPLTVEWRARSESAQSK
Leader sequence
MHC α1α2
2A cleavage sequence
Leader sequence
Peptide
MHC β1β2

SEQUENCE LISTING

<160> NUMBER OF SEQ ID NOS: 278

<210> SEQ ID NO 1
<211> LENGTH: 420
<212> TYPE: PRT
<213> ORGANISM: Artificial sequence
<220> FEATURE:
<223> OTHER INFORMATION: synthetic amino acid sequence

<400> SEQUENCE: 1

```
Glu Leu Ala Gly Ile Gly Ile Leu Thr Val Gly Gly Gly Ser Gly
1               5                   10                  15

Gly Gly Gly Ser Gly Gly Gly Ser Ile Gln Arg Thr Pro Lys Ile
                20                  25                  30

Gln Val Tyr Ser Arg His Pro Ala Glu Asn Gly Lys Ser Asn Phe Leu
            35                  40                  45

Asn Cys Tyr Val Ser Gly Phe His Pro Ser Asp Ile Glu Val Asp Leu
        50                  55                  60

Leu Lys Asn Gly Glu Arg Ile Glu Lys Val Glu His Ser Asp Leu Ser
65                  70                  75                  80

Phe Ser Lys Asp Trp Ser Phe Tyr Leu Leu Tyr Tyr Thr Glu Phe Thr
                85                  90                  95

Pro Thr Glu Lys Asp Glu Tyr Ala Cys Arg Val Asn His Val Thr Leu
            100                 105                 110

Ser Gln Pro Lys Ile Val Lys Trp Asp Arg Asp Met Gly Gly Gly Gly
        115                 120                 125

Ser Gly Gly Gly Gly Ser Gly Gly Gly Ser Gly Gly Gly Gly Ser
    130                 135                 140

His Ser Met Arg Tyr Phe Phe Thr Ser Val Ser Arg Pro Gly Arg Gly
145                 150                 155                 160

Glu Pro Arg Phe Ile Ala Val Gly Tyr Val Asp Asp Thr Gln Phe Val
                165                 170                 175

Arg Phe Asp Ser Asp Ala Ala Ser Gln Arg Met Glu Pro Arg Ala Pro
            180                 185                 190

Trp Ile Glu Gln Glu Gly Pro Glu Tyr Trp Asp Gly Glu Thr Arg Lys
        195                 200                 205

Val Lys Ala His Ser Gln Thr His Arg Val Asp Leu Gly Thr Leu Arg
    210                 215                 220

Gly Ala Tyr Asn Gln Ser Glu Ala Gly Ser His Thr Val Gln Arg Met
225                 230                 235                 240

Tyr Gly Cys Asp Val Gly Ser Asp Trp Arg Phe Leu Arg Gly Tyr His
```

```
                    245                 250                 255
Gln Tyr Ala Tyr Asp Gly Lys Asp Tyr Ile Ala Leu Lys Glu Asp Leu
            260                 265                 270

Arg Ser Trp Thr Ala Ala Asp Met Ala Ala Gln Thr Thr Lys His Lys
        275                 280                 285

Trp Glu Ala Ala His Val Ala Glu Gln Leu Arg Ala Tyr Leu Glu Gly
    290                 295                 300

Thr Cys Val Glu Trp Leu Arg Arg Tyr Leu Glu Asn Gly Lys Glu Thr
305                 310                 315                 320

Leu Gln Arg Thr Asp Ala Pro Lys Thr His Met Thr His His Ala Val
            325                 330                 335

Ser Asp His Glu Ala Thr Leu Arg Cys Trp Ala Leu Ser Phe Tyr Pro
        340                 345                 350

Ala Glu Ile Thr Leu Thr Trp Gln Arg Asp Gly Glu Asp Gln Thr Gln
    355                 360                 365

Asp Thr Glu Leu Val Glu Thr Arg Pro Ala Gly Asp Gly Thr Phe Gln
370                 375                 380

Lys Trp Ala Ala Val Val Pro Ser Gly Gln Glu Gln Arg Tyr Thr
385                 390                 395                 400

Cys His Val Gln His Glu Gly Leu Pro Lys Pro Leu Thr Leu Arg Trp
            405                 410                 415

Glu Pro Ser Ser
            420

<210> SEQ ID NO 2
<211> LENGTH: 421
<212> TYPE: PRT
<213> ORGANISM: Artificial sequence
<220> FEATURE:
<223> OTHER INFORMATION: synthetic amino acid sequence

<400> SEQUENCE: 2

Lys Ala Phe Ser Pro Glu Val Ile Pro Met Phe Gly Gly Gly Gly Ser
1               5                   10                  15

Gly Gly Gly Gly Ser Gly Gly Gly Ser Ile Gln Arg Thr Pro Lys
            20                  25                  30

Ile Gln Val Tyr Ser Arg His Pro Ala Glu Asn Gly Lys Ser Asn Phe
        35                  40                  45

Leu Asn Cys Tyr Val Ser Gly Phe His Pro Ser Asp Ile Glu Val Asp
    50                  55                  60

Leu Leu Lys Asn Gly Glu Arg Ile Glu Lys Val Glu His Ser Asp Leu
65                  70                  75                  80

Ser Phe Ser Lys Asp Trp Ser Phe Tyr Leu Leu Tyr Tyr Thr Glu Phe
            85                  90                  95

Thr Pro Thr Glu Lys Asp Glu Tyr Ala Cys Arg Val Asn His Val Thr
        100                 105                 110

Leu Ser Gln Pro Lys Ile Val Lys Trp Asp Arg Asp Met Gly Gly Gly
    115                 120                 125

Gly Ser Gly Gly Gly Gly Ser Gly Gly Gly Ser Gly Gly Gly Gly
130                 135                 140

Ser His Ser Met Arg Tyr Phe Tyr Thr Ala Met Ser Arg Pro Gly Arg
145                 150                 155                 160

Gly Glu Pro Arg Phe Ile Ala Val Gly Tyr Val Asp Asp Thr Gln Phe
            165                 170                 175

Val Arg Phe Asp Ser Asp Ala Ala Ser Pro Arg Met Ala Pro Arg Ala
```

```
            180                 185                 190
Pro Trp Ile Glu Gln Glu Gly Pro Glu Tyr Trp Asp Gly Glu Thr Arg
        195                 200                 205

Asn Met Lys Ala Ser Ala Gln Thr Tyr Arg Glu Asn Leu Arg Ile Ala
    210                 215                 220

Leu Arg Ala Tyr Asn Gln Ser Glu Ala Gly Ser His Ile Ile Gln Val
225                 230                 235                 240

Met Tyr Gly Cys Asp Val Gly Pro Asp Gly Arg Leu Leu Arg Gly His
            245                 250                 255

Asn Gln Tyr Ala Tyr Asp Gly Lys Asp Tyr Ile Ala Leu Asn Glu Asp
        260                 265                 270

Leu Ser Ser Trp Thr Ala Ala Asp Thr Ala Ala Gln Ile Thr Gln Arg
    275                 280                 285

Lys Trp Glu Ala Ala Arg Val Ala Glu Gln Leu Arg Ala Tyr Leu Glu
290                 295                 300

Gly Leu Cys Val Glu Trp Leu Arg Arg Tyr Leu Glu Asn Gly Lys Glu
305                 310                 315                 320

Thr Leu Gln Arg Ala Asp Pro Pro Lys Thr His Val Thr His His Pro
            325                 330                 335

Ile Ser Asp His Glu Ala Thr Leu Arg Cys Trp Ala Leu Gly Phe Tyr
        340                 345                 350

Pro Ala Glu Ile Thr Leu Thr Trp Gln Arg Asp Gly Glu Asp Gln Thr
    355                 360                 365

Gln Asp Thr Glu Leu Val Glu Thr Arg Pro Ala Gly Asp Arg Thr Phe
370                 375                 380

Gln Lys Trp Ala Ala Val Val Val Pro Ser Gly Glu Glu Gln Arg Tyr
385                 390                 395                 400

Thr Cys His Val Gln His Glu Gly Leu Pro Lys Pro Leu Thr Leu Arg
            405                 410                 415

Trp Glu Pro Ser Ser
            420

<210> SEQ ID NO 3
<211> LENGTH: 217
<212> TYPE: PRT
<213> ORGANISM: Artificial sequence
<220> FEATURE:
<223> OTHER INFORMATION: synthetic amino acid sequence

<400> SEQUENCE: 3

Glu Asn Pro Val Val His Phe Phe Lys Asn Ile Val Thr Pro Arg Gly
1               5                   10                  15

Gly Gly Gly Ser Gly Gly Gly Ser Gly Gly Gly Ser Gly Gly Gly Asp
            20                  25                  30

Thr Arg Pro Arg Phe Leu Trp Gln Ser Lys Arg Glu Cys His Phe Phe
        35                  40                  45

Asn Gly Thr Glu Arg Val Arg Phe Leu Asp Arg Tyr Phe Tyr Asn Gln
    50                  55                  60

Glu Glu Ser Val Arg Phe Asp Ser Asp Val Gly Glu Phe Arg Ala Val
65                  70                  75                  80

Thr Glu Leu Gly Arg Pro Asp Ala Glu Tyr Trp Asn Ser Gln Lys Asp
                85                  90                  95

Ile Leu Glu Gln Ala Arg Ala Ala Val Asp Thr Tyr Cys Arg His Asn
            100                 105                 110

Tyr Gly Val Val Glu Ser Phe Thr Val Gln Arg Arg Val Gln Gly Gly
```

115                 120                 125
Gly Gly Ser Gly Gly Ile Lys Glu Glu His Val Ile Gln Ala
    130                 135                 140
Glu Ser Tyr Leu Asn Pro Asp Gln Ser Gly Glu Phe Lys Phe Asp Phe
145                 150                 155                 160
Asp Gly Asp Glu Ile Phe His Val Asp Met Ala Lys Lys Glu Thr Val
                165                 170                 175
Trp Arg Leu Glu Glu Phe Gly Arg Phe Ala Ser Phe Glu Ala Gln Gly
            180                 185                 190
Ala Leu Ala Asn Ile Ala Val Asp Lys Ala Asn Leu Glu Ile Met Thr
            195                 200                 205
Lys Arg Ser Asn Tyr Thr Pro Ile Thr
            210                 215

<210> SEQ ID NO 4
<211> LENGTH: 207
<212> TYPE: PRT
<213> ORGANISM: Artificial sequence
<220> FEATURE:
<223> OTHER INFORMATION: synthetic amino acid sequence

<400> SEQUENCE: 4

Gln Leu Ser Pro Phe Pro Phe Asp Leu Gly Gly Gly Ser Gly Gly
1               5                   10                  15
Gly Gly Ser Gly Gly Ser Tyr Tyr Ile Ala Leu Asn Glu Asp Leu Arg
            20                  25                  30
Thr Trp Thr Ala Thr Asp Met Ala Ala Gln Ile Thr Arg Arg Lys Trp
        35                  40                  45
Glu Gln Ala Gly Ala Ala Glu Tyr Tyr Arg Ala Tyr Leu Glu Gly Glu
    50                  55                  60
Cys Val Glu Trp Leu His Arg Tyr Leu Lys Asn Gly Asn Ala Thr Leu
65                  70                  75                  80
Leu Gly Gly Gly Gly Ser Gly Gly Pro His Ser Met Arg Tyr Phe Glu
                85                  90                  95
Thr Ala Val Ser Arg Pro Gly Leu Gly Glu Pro Arg Tyr Ile Ser Val
            100                 105                 110
Gly Tyr Val Asp Asp Lys Glu Phe Val Arg Phe Asp Ser Asp Ala Glu
        115                 120                 125
Asn Pro Arg Tyr Glu Pro Gln Val Pro Trp Met Glu Gln Glu Gly Pro
    130                 135                 140
Glu Tyr Trp Glu Arg Ile Thr Gln Ile Ala Lys Gly Gln Glu Gln Trp
145                 150                 155                 160
Phe Arg Val Asn Leu Arg Thr Leu Leu Gly Ala Tyr Asn Gln Ser Ala
                165                 170                 175
Gly Gly Thr His Thr Leu Gln Trp Met Tyr Gly Cys Asp Val Gly Ser
            180                 185                 190
Asp Gly Arg Leu Leu Arg Gly Tyr Glu Gln Phe Ala Tyr Asp Gly
        195                 200                 205

<210> SEQ ID NO 5
<211> LENGTH: 210
<212> TYPE: PRT
<213> ORGANISM: Artificial sequence
<220> FEATURE:
<223> OTHER INFORMATION: synthetic amino acid sequence

<400> SEQUENCE: 5

Ala Asp Leu Ile Ala Tyr Leu Lys Gln Ala Thr Lys Gly Gly Gly Ser
1               5                   10                  15

Gly Gly Gly Gly Ser Gly Gly Ser Gly Arg Pro Ser Phe Thr Glu
            20                  25                  30

Tyr Cys Lys Ser Glu Cys His Phe Tyr Asn Gly Thr Gln Arg Val Arg
                35                  40                  45

Leu Leu Val Arg Tyr Phe Tyr Asn Ser Glu Glu Asn Leu Arg Phe Asp
        50                  55                  60

Ser Asp Val Gly Glu Phe Arg Ala Val Thr Glu Leu Gly Arg Pro Asp
65                  70                  75                  80

Ala Glu Asn Trp Asn Ser Gln Pro Glu Phe Leu Glu Gln Lys Arg Ala
                85                  90                  95

Glu Val Asp Thr Val Cys Arg His Asn Tyr Glu Ile Phe Asp Asn Phe
                100                 105                 110

Leu Val Pro Arg Arg Val Glu Gly Gly Gly Ser Gly Gly Gly Ile
        115                 120                 125

Lys Glu Glu His Thr Ile Thr Gln Ala Glu Ser Tyr Thr Leu Pro Asp
    130                 135                 140

Lys Arg Gly Glu Phe Met Phe Asp Phe Asp Gly Asp Glu Ile Phe His
145                 150                 155                 160

Val Asp Ile Glu Lys Ser Glu Thr Ile Trp Arg Leu Glu Glu Phe Ala
                165                 170                 175

Lys Phe Ala Ser Phe Glu Val Gln Gly Ala Leu Ala Asn Ile Ala Val
                180                 185                 190

Asp Lys Ala Asn Leu Asp Val Met Lys Glu Arg Ser Asn Asn Thr Pro
        195                 200                 205

Asp Ala
    210

<210> SEQ ID NO 6
<211> LENGTH: 490
<212> TYPE: PRT
<213> ORGANISM: Artificial sequence
<220> FEATURE:
<223> OTHER INFORMATION: synthetic amino acid sequence

<400> SEQUENCE: 6

Met Gln Leu Leu Arg Cys Phe Ser Ile Phe Ser Val Ile Ala Ser Val
1               5                   10                  15

Leu Ala Ile Lys Glu Glu His Val Ile Ile Gln Ala Glu Phe Tyr Leu
            20                  25                  30

Asn Pro Asp Gln Ser Gly Glu Phe Met Phe Asp Phe Asp Gly Asp Glu
        35                  40                  45

Ile Phe His Val Asp Leu Ala Lys Lys Glu Thr Val Trp Arg Leu Glu
50                  55                  60

Glu Phe Gly Arg Phe Ala Ser Phe Glu Ala Gln Gly Ala Leu Ala Asn
65                  70                  75                  80

Ile Ala Val Asp Lys Ala Asn Leu Glu Ile Met Thr Lys Arg Ser Asn
                85                  90                  95

Tyr Thr Pro Ile Thr Asn Val Pro Pro Glu Val Thr Val Leu Thr Asn
                100                 105                 110

Ser Pro Val Glu Leu Arg Glu Pro Asn Val Leu Ile Cys Phe Ile Asp
        115                 120                 125

Lys Phe Thr Pro Pro Val Val Asn Val Thr Trp Leu Arg Asn Gly Lys
    130                 135                 140

```
Pro Val Thr Thr Gly Met Ser Glu Thr Val Phe Leu Pro Arg Glu Asp
145                 150                 155                 160

His Leu Phe Arg Lys Phe His Tyr Leu Pro Phe Leu Pro Ser Thr Glu
                165                 170                 175

Asp Val Tyr Asp Cys Arg Val Glu His Trp Gly Leu Asp Glu Pro Leu
            180                 185                 190

Leu Lys His Trp Glu Phe Asp Ala Pro Ser Pro Leu Pro Glu Thr Thr
        195                 200                 205

Glu Gly Ser Gly Ser Tyr Pro Tyr Asp Val Pro Asp Tyr Ala Gly Ser
210                 215                 220

Gly Ala Thr Asn Phe Ser Leu Leu Lys Gln Ala Gly Asp Val Glu Glu
225                 230                 235                 240

Asn Pro Gly Pro Met Gln Leu Leu Arg Cys Phe Ser Ile Phe Ser Val
                245                 250                 255

Ile Ala Ser Val Leu Ala Phe Ser Trp Gly Ala Glu Gly Gln Arg Pro
            260                 265                 270

Gly Phe Gly Phe Gly Gly Gly Gly Ser Gly Gly Gly Ser Gly
        275                 280                 285

Gly Gly Ser Gly Gly Asp Thr Arg Pro Arg Phe Leu Glu Gln Val Lys
290                 295                 300

His Glu Cys His Phe Phe Asn Gly Thr Glu Arg Val Arg Phe Leu Asp
305                 310                 315                 320

Arg Tyr Phe Tyr Asn Gln Glu Glu Tyr Val Arg Phe Asp Ser Glu Val
                325                 330                 335

Gly Glu Tyr Arg Ala Val Thr Glu Leu Gly Arg Pro Asp Ala Glu Tyr
            340                 345                 350

Trp Asn Ser Gln Lys Asp Leu Leu Glu Gln Lys Arg Ala Ala Val Asp
        355                 360                 365

Thr Tyr Cys Arg His Asn Tyr Gly Val Gly Glu Ser Phe Thr Val Gln
370                 375                 380

Arg Arg Val Tyr Pro Glu Val Thr Val Tyr Pro Ala Lys Thr Gln Pro
385                 390                 395                 400

Leu Gln His His Asn Leu Leu Val Cys Ser Val Asn Gly Phe Tyr Pro
                405                 410                 415

Gly Ser Ile Glu Val Arg Trp Phe Arg Asn Gly Gln Glu Glu Lys Thr
            420                 425                 430

Gly Val Val Ser Thr Gly Leu Ile Gln Asn Gly Asp Trp Thr Phe Gln
        435                 440                 445

Thr Leu Val Met Leu Glu Thr Val Pro Arg Ser Gly Glu Val Tyr Thr
450                 455                 460

Cys Gln Val Glu His Pro Ser Leu Thr Ser Pro Leu Thr Val Glu Trp
465                 470                 475                 480

Arg Ala Arg Ser Glu Ser Ala Gln Ser Lys
                485                 490

<210> SEQ ID NO 7
<211> LENGTH: 13
<212> TYPE: PRT
<213> ORGANISM: Artificial sequence
<220> FEATURE:
<223> OTHER INFORMATION: synthetic amino acid sequence

<400> SEQUENCE: 7

Ala Asp Leu Ile Ala Tyr Leu Lys Gln Ala Thr Lys Gly
1               5                   10
```

```
<210> SEQ ID NO 8
<211> LENGTH: 13
<212> TYPE: PRT
<213> ORGANISM: Artificial sequence
<220> FEATURE:
<223> OTHER INFORMATION: synthetic amino acid sequence

<400> SEQUENCE: 8

Ala Thr His Val Ala Phe Leu Lys Ala Ala Thr Lys Lys
1               5                   10

<210> SEQ ID NO 9
<211> LENGTH: 13
<212> TYPE: PRT
<213> ORGANISM: Artificial sequence
<220> FEATURE:
<223> OTHER INFORMATION: synthetic amino acid sequence

<400> SEQUENCE: 9

Ala Asp Leu Val Ala Phe Phe Lys Glu Ala Ser Lys Arg
1               5                   10

<210> SEQ ID NO 10
<211> LENGTH: 13
<212> TYPE: PRT
<213> ORGANISM: Artificial sequence
<220> FEATURE:
<223> OTHER INFORMATION: synthetic amino acid sequence

<400> SEQUENCE: 10

Ala Asp Leu Val Ala Phe Phe Lys Ala Ala Thr Lys Thr
1               5                   10

<210> SEQ ID NO 11
<211> LENGTH: 12
<212> TYPE: PRT
<213> ORGANISM: Mus musculus

<400> SEQUENCE: 11

Ala Asp Pro Val Ala Phe Phe Ser Ser Ala Ile Lys
1               5                   10

<210> SEQ ID NO 12
<211> LENGTH: 12
<212> TYPE: PRT
<213> ORGANISM: Mus musculus

<400> SEQUENCE: 12

Ala Asp Leu Ile Ala Tyr Leu Lys Gln Ala Thr Lys
1               5                   10

<210> SEQ ID NO 13
<211> LENGTH: 12
<212> TYPE: PRT
<213> ORGANISM: Mus musculus

<400> SEQUENCE: 13

Ala Asn Gly Val Ala Phe Phe Leu Thr Pro Phe Lys
1               5                   10

<210> SEQ ID NO 14
<211> LENGTH: 12
<212> TYPE: PRT
<213> ORGANISM: Mus musculus

<400> SEQUENCE: 14
```

```
Ala Asp Leu Ile Ala Tyr Leu Lys Gln Ala Thr Lys
1               5                   10

<210> SEQ ID NO 15
<211> LENGTH: 10
<212> TYPE: PRT
<213> ORGANISM: Artificial sequence
<220> FEATURE:
<223> OTHER INFORMATION: synthetic amino acid sequence

<400> SEQUENCE: 15

Leu Ile Ala Tyr Leu Lys Gln Ala Thr Lys
1               5                   10

<210> SEQ ID NO 16
<211> LENGTH: 10
<212> TYPE: PRT
<213> ORGANISM: Artificial sequence
<220> FEATURE:
<223> OTHER INFORMATION: synthetic amino acid sequence

<400> SEQUENCE: 16

Leu Val Ala Phe Leu Lys Ala Ala Thr Lys
1               5                   10

<210> SEQ ID NO 17
<211> LENGTH: 10
<212> TYPE: PRT
<213> ORGANISM: Artificial sequence
<220> FEATURE:
<223> OTHER INFORMATION: synthetic amino acid sequence

<400> SEQUENCE: 17

Pro Val Ala Phe Leu Lys Ser Ala Thr Lys
1               5                   10

<210> SEQ ID NO 18
<211> LENGTH: 10
<212> TYPE: PRT
<213> ORGANISM: Artificial sequence
<220> FEATURE:
<223> OTHER INFORMATION: synthetic amino acid sequence

<400> SEQUENCE: 18

Pro Ile Ala Phe Met Lys Ser Ala Ile Lys
1               5                   10

<210> SEQ ID NO 19
<211> LENGTH: 10
<212> TYPE: PRT
<213> ORGANISM: Artificial sequence
<220> FEATURE:
<223> OTHER INFORMATION: synthetic amino acid sequence

<400> SEQUENCE: 19

Pro Val Ala Phe Phe Ser Ser Ala Ile Lys
1               5                   10

<210> SEQ ID NO 20
<211> LENGTH: 14
<212> TYPE: PRT
<213> ORGANISM: Homo sapiens

<400> SEQUENCE: 20

Glu Asn Pro Val Val His Phe Phe Lys Asn Ile Val Thr Pro
1               5                   10
```

```
<210> SEQ ID NO 21
<211> LENGTH: 14
<212> TYPE: PRT
<213> ORGANISM: Sulfurovum sp. NBC37-1

<400> SEQUENCE: 21

Ser Leu Gly Asn Ile His Phe Phe Lys Ser Glu Val Val Arg
1               5                   10

<210> SEQ ID NO 22
<211> LENGTH: 14
<212> TYPE: PRT
<213> ORGANISM: Populus trichocarpa

<400> SEQUENCE: 22

Ser Val Ser Val Ile His Phe Phe Lys Ala Pro Ala Ala Ile
1               5                   10

<210> SEQ ID NO 23
<211> LENGTH: 14
<212> TYPE: PRT
<213> ORGANISM: Chlorobium chlorochromatii

<400> SEQUENCE: 23

Val Phe Gly Asn Val His Phe Phe Lys Asn Thr Gly Ser Ala
1               5                   10

<210> SEQ ID NO 24
<211> LENGTH: 14
<212> TYPE: PRT
<213> ORGANISM: Rhodococcus sp. AW25M09

<400> SEQUENCE: 24

Ala Ala Gln Arg Ile His Phe Phe Lys Asn Leu Ser Leu Leu
1               5                   10

<210> SEQ ID NO 25
<211> LENGTH: 14
<212> TYPE: PRT
<213> ORGANISM: Selaginella moellendorffii

<400> SEQUENCE: 25

Ser Val Gly Lys Ile His Phe Phe Lys Met Glu Val Val Ser
1               5                   10

<210> SEQ ID NO 26
<211> LENGTH: 14
<212> TYPE: PRT
<213> ORGANISM: Legionella longbeachae

<400> SEQUENCE: 26

Asn Pro Gln Val Ile His Phe Phe Lys Ser Leu Asp Leu Leu
1               5                   10

<210> SEQ ID NO 27
<211> LENGTH: 14
<212> TYPE: PRT
<213> ORGANISM: Encephalitozoon romaleae

<400> SEQUENCE: 27

Phe Gly Val Lys Ile His Phe Phe Lys Gln Arg Asn Ser Leu
1               5                   10
```

```
<210> SEQ ID NO 28
<211> LENGTH: 14
<212> TYPE: PRT
<213> ORGANISM: Oryzias latipes

<400> SEQUENCE: 28

Glu Asn Ala Val Val His Phe Phe Arg Ser Leu Val Ser Ser
1               5                   10

<210> SEQ ID NO 29
<211> LENGTH: 14
<212> TYPE: PRT
<213> ORGANISM: Kitasatospora setae KM-6054

<400> SEQUENCE: 29

Met His Gly Asn Trp His Phe Phe Arg Asn Phe Leu Ser Asn
1               5                   10

<210> SEQ ID NO 30
<211> LENGTH: 14
<212> TYPE: PRT
<213> ORGANISM: Desulfotignum

<400> SEQUENCE: 30

Val Ser Gly Tyr Val His Phe Phe Arg Gly Leu Pro Leu Leu
1               5                   10

<210> SEQ ID NO 31
<211> LENGTH: 14
<212> TYPE: PRT
<213> ORGANISM: Volvox carteri f.

<400> SEQUENCE: 31

Gly Ala His Cys Ile His Phe Phe Lys Ser Ala Val Cys Arg
1               5                   10

<210> SEQ ID NO 32
<211> LENGTH: 14
<212> TYPE: PRT
<213> ORGANISM: Clostridium papyrosolvens

<400> SEQUENCE: 32

Leu Asn Lys Asn Ile His Phe Phe Lys Asn Leu Pro Leu Pro
1               5                   10

<210> SEQ ID NO 33
<211> LENGTH: 14
<212> TYPE: PRT
<213> ORGANISM: Oryctolagus cuniculus

<400> SEQUENCE: 33

Arg Thr Gln Arg Ile His Phe Phe Lys Gly Asp Lys Val Trp
1               5                   10

<210> SEQ ID NO 34
<211> LENGTH: 14
<212> TYPE: PRT
<213> ORGANISM: Anoxybacillus flavithermus

<400> SEQUENCE: 34

Arg Leu Ser Val Val His Phe Leu Arg Ala Asn Ala Val Ser
1               5                   10

<210> SEQ ID NO 35
<211> LENGTH: 14
```

```
<212> TYPE: PRT
<213> ORGANISM: Macrophomina phaseolina MS6

<400> SEQUENCE: 35

Ala Ala Gln Asn Val His Phe Trp Lys Ala Leu Asn Gln Leu
1               5                   10

<210> SEQ ID NO 36
<211> LENGTH: 14
<212> TYPE: PRT
<213> ORGANISM: Emiliania huxleyi CCMP1516

<400> SEQUENCE: 36

Ser Thr Ala Arg Val His Phe Trp Arg Ser Arg Ser Ser Glu
1               5                   10

<210> SEQ ID NO 37
<211> LENGTH: 14
<212> TYPE: PRT
<213> ORGANISM: Rhizobium leguminosarum

<400> SEQUENCE: 37

Asp Val Ser Lys Val His Phe Phe Lys Gly Asn Gly Gln Thr
1               5                   10

<210> SEQ ID NO 38
<211> LENGTH: 14
<212> TYPE: PRT
<213> ORGANISM: Runella slithyformis DSM

<400> SEQUENCE: 38

His Arg Ala Lys Leu His Phe Phe Lys Asp Glu Asn Leu Lys
1               5                   10

<210> SEQ ID NO 39
<211> LENGTH: 14
<212> TYPE: PRT
<213> ORGANISM: Blastococcus saxobsidens DD2

<400> SEQUENCE: 39

Ala Arg Ser Val Phe His Phe Phe Arg Gly Thr Ala Leu Leu
1               5                   10

<210> SEQ ID NO 40
<211> LENGTH: 14
<212> TYPE: PRT
<213> ORGANISM: Dictyostelium fasciculatum

<400> SEQUENCE: 40

Tyr Lys His Lys Ile His Phe Phe Lys Asn Glu Val Leu Glu
1               5                   10

<210> SEQ ID NO 41
<211> LENGTH: 14
<212> TYPE: PRT
<213> ORGANISM: Rhodanobacter sp. 116-2

<400> SEQUENCE: 41

Thr Glu Gly Ser Val His Phe Phe Arg Gly His Ala Val Ile
1               5                   10

<210> SEQ ID NO 42
<211> LENGTH: 14
<212> TYPE: PRT
<213> ORGANISM: Ogataea parapolymorpha DL-1
```

<400> SEQUENCE: 42

Ile Glu Ala Ala Ile His Phe Tyr Lys Gly Leu Ala Val Tyr
1               5                   10

<210> SEQ ID NO 43
<211> LENGTH: 14
<212> TYPE: PRT
<213> ORGANISM: Myxococcus stipitatus DSM

<400> SEQUENCE: 43

Ser Ser Ala Arg Leu His Phe Phe Arg Ala Leu Pro His Pro
1               5                   10

<210> SEQ ID NO 44
<211> LENGTH: 14
<212> TYPE: PRT
<213> ORGANISM: Bacillus clausii KSM-K16

<400> SEQUENCE: 44

His Glu Asn Val Val His Phe Phe Lys Asp Gly Glu Leu Val
1               5                   10

<210> SEQ ID NO 45
<211> LENGTH: 14
<212> TYPE: PRT
<213> ORGANISM: Trichosporon asahii var.

<400> SEQUENCE: 45

Leu Glu Ser Val Val His Phe Leu Arg Gly Gln Lys Val Thr
1               5                   10

<210> SEQ ID NO 46
<211> LENGTH: 14
<212> TYPE: PRT
<213> ORGANISM: Acinetobacter sp. ADP1

<400> SEQUENCE: 46

Ser Glu Gly Ser Ile His Phe Phe Lys Ala Asp Leu Leu Ser
1               5                   10

<210> SEQ ID NO 47
<211> LENGTH: 14
<212> TYPE: PRT
<213> ORGANISM: Homo sapiens

<400> SEQUENCE: 47

Met Asn Ala Ser Ile His Phe Leu Lys Ala Leu Glu Thr Tyr
1               5                   10

<210> SEQ ID NO 48
<211> LENGTH: 14
<212> TYPE: PRT
<213> ORGANISM: Homo sapiens

<400> SEQUENCE: 48

Asn Ala Asn Val Leu His Phe Leu Lys Asn Ile Ile Cys Gln
1               5                   10

<210> SEQ ID NO 49
<211> LENGTH: 14
<212> TYPE: PRT
<213> ORGANISM: Homo sapiens

<400> SEQUENCE: 49

```
Phe Leu Lys Lys Phe His Phe Leu Lys Gly Ala Thr Leu Cys
1               5                   10
```

<210> SEQ ID NO 50
<211> LENGTH: 14
<212> TYPE: PRT
<213> ORGANISM: Homo sapiens

<400> SEQUENCE: 50

```
Ile Ile Pro Ala Phe His Phe Leu Lys Ser Glu Lys Gly Leu
1               5                   10
```

<210> SEQ ID NO 51
<211> LENGTH: 14
<212> TYPE: PRT
<213> ORGANISM: Homo sapiens

<400> SEQUENCE: 51

```
Ser Ala Asn Asn Ile His Phe Met Arg Gln Ser Glu Ile Gly
1               5                   10
```

<210> SEQ ID NO 52
<211> LENGTH: 14
<212> TYPE: PRT
<213> ORGANISM: Homo sapiens

<400> SEQUENCE: 52

```
Ala Pro Leu Val Ile His Phe Leu Lys Ala Pro Pro Ala Pro
1               5                   10
```

<210> SEQ ID NO 53
<211> LENGTH: 14
<212> TYPE: PRT
<213> ORGANISM: Homo sapiens

<400> SEQUENCE: 53

```
His Met Leu Ser Phe His Phe Trp Lys Ser Arg Gly Gln Thr
1               5                   10
```

<210> SEQ ID NO 54
<211> LENGTH: 13
<212> TYPE: PRT
<213> ORGANISM: Artificial sequence
<220> FEATURE:
<223> OTHER INFORMATION: synthetic amino acid sequence

<400> SEQUENCE: 54

```
Ala Asp Leu Val Ala Phe Phe Lys Glu Ala Ser Lys Arg
1               5                   10
```

<210> SEQ ID NO 55
<211> LENGTH: 13
<212> TYPE: PRT
<213> ORGANISM: Artificial sequence
<220> FEATURE:
<223> OTHER INFORMATION: synthetic amino acid sequence

<400> SEQUENCE: 55

```
Ala Thr His Val Ala Phe Leu Lys Ala Ala Thr Lys Lys
1               5                   10
```

<210> SEQ ID NO 56
<211> LENGTH: 13
<212> TYPE: PRT
<213> ORGANISM: Artificial sequence

```
<220> FEATURE:
<223> OTHER INFORMATION: synthetic amino acid sequence

<400> SEQUENCE: 56

Ala Ala Gln Val Ala Phe Leu Lys Ala Ala Thr Lys Ala
1               5                   10

<210> SEQ ID NO 57
<211> LENGTH: 13
<212> TYPE: PRT
<213> ORGANISM: Artificial sequence
<220> FEATURE:
<223> OTHER INFORMATION: synthetic amino acid sequence

<400> SEQUENCE: 57

Ala Thr His Val Ala Phe Leu Lys Ala Ala Thr Lys Ala
1               5                   10

<210> SEQ ID NO 58
<211> LENGTH: 13
<212> TYPE: PRT
<213> ORGANISM: Artificial sequence
<220> FEATURE:
<223> OTHER INFORMATION: synthetic amino acid sequence

<400> SEQUENCE: 58

Ala Ala Gln Val Ala Phe Leu Lys Ala Ala Thr Lys Lys
1               5                   10

<210> SEQ ID NO 59
<211> LENGTH: 13
<212> TYPE: PRT
<213> ORGANISM: Artificial sequence
<220> FEATURE:
<223> OTHER INFORMATION: synthetic amino acid sequence

<400> SEQUENCE: 59

Ala Asp Trp Val Ala Phe Leu Lys Gln Ala Thr Lys Gly
1               5                   10

<210> SEQ ID NO 60
<211> LENGTH: 13
<212> TYPE: PRT
<213> ORGANISM: Artificial sequence
<220> FEATURE:
<223> OTHER INFORMATION: synthetic amino acid sequence

<400> SEQUENCE: 60

Ala Asp Leu Val Ala Phe Phe Lys Glu Ala Ser Lys Lys
1               5                   10

<210> SEQ ID NO 61
<211> LENGTH: 13
<212> TYPE: PRT
<213> ORGANISM: Artificial sequence
<220> FEATURE:
<223> OTHER INFORMATION: synthetic amino acid sequence

<400> SEQUENCE: 61

Ala Ala Pro Val Ala Phe Leu Lys Ser Ala Ser Lys Thr
1               5                   10

<210> SEQ ID NO 62
<211> LENGTH: 13
<212> TYPE: PRT
<213> ORGANISM: Artificial sequence
<220> FEATURE:
```

```
<223> OTHER INFORMATION: synthetic amino acid sequence

<400> SEQUENCE: 62

Ala Asn Gly Leu Ala Phe Phe Lys Ser Ala Ser Lys Thr
1               5                   10

<210> SEQ ID NO 63
<211> LENGTH: 13
<212> TYPE: PRT
<213> ORGANISM: Artificial sequence
<220> FEATURE:
<223> OTHER INFORMATION: synthetic amino acid sequence

<400> SEQUENCE: 63

Ala Thr His Val Ala Phe Leu Lys Ala Ala Thr Lys Arg
1               5                   10

<210> SEQ ID NO 64
<211> LENGTH: 13
<212> TYPE: PRT
<213> ORGANISM: Artificial sequence
<220> FEATURE:
<223> OTHER INFORMATION: synthetic amino acid sequence

<400> SEQUENCE: 64

Ala Asp Leu Val Ala Phe Leu Lys Ala Ala Thr Lys Ala
1               5                   10

<210> SEQ ID NO 65
<211> LENGTH: 13
<212> TYPE: PRT
<213> ORGANISM: Artificial sequence
<220> FEATURE:
<223> OTHER INFORMATION: synthetic amino acid sequence

<400> SEQUENCE: 65

Ala Asp Leu Val Ala Phe Leu Lys Ala Ala Thr Lys Lys
1               5                   10

<210> SEQ ID NO 66
<211> LENGTH: 13
<212> TYPE: PRT
<213> ORGANISM: Artificial sequence
<220> FEATURE:
<223> OTHER INFORMATION: synthetic amino acid sequence

<400> SEQUENCE: 66

Ala Asp Gly Val Ala Phe Phe Met Ser Ala Thr Lys Thr
1               5                   10

<210> SEQ ID NO 67
<211> LENGTH: 13
<212> TYPE: PRT
<213> ORGANISM: Artificial sequence
<220> FEATURE:
<223> OTHER INFORMATION: synthetic amino acid sequence

<400> SEQUENCE: 67

Ala Asp Leu Val Ala Phe Phe Lys Glu Ala Ser Lys Ala
1               5                   10

<210> SEQ ID NO 68
<211> LENGTH: 13
<212> TYPE: PRT
<213> ORGANISM: Artificial sequence
<220> FEATURE:
<223> OTHER INFORMATION: synthetic amino acid sequence
```

-continued

```
<400> SEQUENCE: 68

Ala Asp Leu Val Ala Phe Phe Lys Ala Ala Thr Lys Ala
1               5                   10

<210> SEQ ID NO 69
<211> LENGTH: 13
<212> TYPE: PRT
<213> ORGANISM: Artificial sequence
<220> FEATURE:
<223> OTHER INFORMATION: synthetic amino acid sequence

<400> SEQUENCE: 69

Ala Thr His Val Ala Phe Leu Lys Ala Ala Ser Lys Arg
1               5                   10

<210> SEQ ID NO 70
<211> LENGTH: 13
<212> TYPE: PRT
<213> ORGANISM: Artificial sequence
<220> FEATURE:
<223> OTHER INFORMATION: synthetic amino acid sequence

<400> SEQUENCE: 70

Ala Asp Leu Val Ala Phe Phe Lys Ala Ala Thr Lys Lys
1               5                   10

<210> SEQ ID NO 71
<211> LENGTH: 13
<212> TYPE: PRT
<213> ORGANISM: Artificial sequence
<220> FEATURE:
<223> OTHER INFORMATION: synthetic amino acid sequence

<400> SEQUENCE: 71

Ala Ala Gln Val Ala Phe Phe Lys Glu Ala Ser Lys Arg
1               5                   10

<210> SEQ ID NO 72
<211> LENGTH: 13
<212> TYPE: PRT
<213> ORGANISM: Artificial sequence
<220> FEATURE:
<223> OTHER INFORMATION: synthetic amino acid sequence

<400> SEQUENCE: 72

Ala Thr His Val Ala Phe Leu Lys Glu Ala Ser Lys Arg
1               5                   10

<210> SEQ ID NO 73
<211> LENGTH: 13
<212> TYPE: PRT
<213> ORGANISM: Artificial sequence
<220> FEATURE:
<223> OTHER INFORMATION: synthetic amino acid sequence

<400> SEQUENCE: 73

Ala Thr His Val Ala Phe Phe Lys Glu Ala Ser Lys Arg
1               5                   10

<210> SEQ ID NO 74
<211> LENGTH: 13
<212> TYPE: PRT
<213> ORGANISM: Artificial sequence
<220> FEATURE:
<223> OTHER INFORMATION: synthetic amino acid sequence
```

```
<400> SEQUENCE: 74

Ala Asp Leu Val Ala Phe Phe Lys Glu Ala Thr Lys Lys
1               5                   10

<210> SEQ ID NO 75
<211> LENGTH: 13
<212> TYPE: PRT
<213> ORGANISM: Artificial sequence
<220> FEATURE:
<223> OTHER INFORMATION: synthetic amino acid sequence

<400> SEQUENCE: 75

Ala Asp Ala Ile Ala Phe Phe Ser Ser Ser Leu Lys Arg
1               5                   10

<210> SEQ ID NO 76
<211> LENGTH: 13
<212> TYPE: PRT
<213> ORGANISM: Artificial sequence
<220> FEATURE:
<223> OTHER INFORMATION: synthetic amino acid sequence

<400> SEQUENCE: 76

Ala Asp Pro Ile Ala Phe Met Lys Ser Ala Ile Lys Lys
1               5                   10

<210> SEQ ID NO 77
<211> LENGTH: 13
<212> TYPE: PRT
<213> ORGANISM: Artificial sequence
<220> FEATURE:
<223> OTHER INFORMATION: synthetic amino acid sequence

<400> SEQUENCE: 77

Ala Asp Leu Val Ala Phe Phe Lys Ser Ala Ser Lys Thr
1               5                   10

<210> SEQ ID NO 78
<211> LENGTH: 13
<212> TYPE: PRT
<213> ORGANISM: Artificial sequence
<220> FEATURE:
<223> OTHER INFORMATION: synthetic amino acid sequence

<400> SEQUENCE: 78

Ala Thr His Val Ala Phe Leu Lys Ala Ala Thr Lys Thr
1               5                   10

<210> SEQ ID NO 79
<211> LENGTH: 13
<212> TYPE: PRT
<213> ORGANISM: Artificial sequence
<220> FEATURE:
<223> OTHER INFORMATION: synthetic amino acid sequence

<400> SEQUENCE: 79

Ala Asn Gly Val Ala Phe Phe Leu Thr Pro Phe Lys Ala
1               5                   10

<210> SEQ ID NO 80
<211> LENGTH: 13
<212> TYPE: PRT
<213> ORGANISM: Artificial sequence
<220> FEATURE:
<223> OTHER INFORMATION: synthetic amino acid sequence

<400> SEQUENCE: 80
```

```
Ala Ala Gln Val Ala Phe Leu Lys Ala Ala Thr Lys Ala
1               5                  10
```

<210> SEQ ID NO 81
<211> LENGTH: 13
<212> TYPE: PRT
<213> ORGANISM: Artificial sequence
<220> FEATURE:
<223> OTHER INFORMATION: synthetic amino acid sequence

<400> SEQUENCE: 81

```
Ala Asp Gly Val Gly Phe Leu Lys Ala Ala Ser Lys Arg
1               5                  10
```

<210> SEQ ID NO 82
<211> LENGTH: 13
<212> TYPE: PRT
<213> ORGANISM: Artificial sequence
<220> FEATURE:
<223> OTHER INFORMATION: synthetic amino acid sequence

<400> SEQUENCE: 82

```
Ala Ala Gly Val Ala Phe Phe Arg Val Pro Tyr Lys Glu
1               5                  10
```

<210> SEQ ID NO 83
<211> LENGTH: 13
<212> TYPE: PRT
<213> ORGANISM: Artificial sequence
<220> FEATURE:
<223> OTHER INFORMATION: synthetic amino acid sequence

<400> SEQUENCE: 83

```
Ala Asp Gly Val Gly Phe Phe Val Ser Pro Phe Lys Lys
1               5                  10
```

<210> SEQ ID NO 84
<211> LENGTH: 13
<212> TYPE: PRT
<213> ORGANISM: Artificial sequence
<220> FEATURE:
<223> OTHER INFORMATION: synthetic amino acid sequence

<400> SEQUENCE: 84

```
Ala Asp Trp Ile Ala Tyr Phe Arg Ser Pro Phe Lys Gly
1               5                  10
```

<210> SEQ ID NO 85
<211> LENGTH: 13
<212> TYPE: PRT
<213> ORGANISM: Artificial sequence
<220> FEATURE:
<223> OTHER INFORMATION: synthetic amino acid sequence

<400> SEQUENCE: 85

```
Ala Asp Gly Leu Ala Tyr Phe Arg Ser Ser Phe Lys Gly
1               5                  10
```

<210> SEQ ID NO 86
<211> LENGTH: 13
<212> TYPE: PRT
<213> ORGANISM: Artificial sequence
<220> FEATURE:
<223> OTHER INFORMATION: synthetic amino acid sequence

<400> SEQUENCE: 86

```
Ala Asp Leu Val Gly Phe Phe Lys Thr Ala Thr Lys Lys
1               5                   10
```

<210> SEQ ID NO 87
<211> LENGTH: 13
<212> TYPE: PRT
<213> ORGANISM: Artificial sequence
<220> FEATURE:
<223> OTHER INFORMATION: synthetic amino acid sequence

<400> SEQUENCE: 87

```
Ala Asn Leu Val Ala Phe Phe Arg Ser Pro Tyr Lys Ala
1               5                   10
```

<210> SEQ ID NO 88
<211> LENGTH: 13
<212> TYPE: PRT
<213> ORGANISM: Artificial sequence
<220> FEATURE:
<223> OTHER INFORMATION: synthetic amino acid sequence

<400> SEQUENCE: 88

```
Ala Asp Arg Leu Ala Tyr Phe Leu Gln Pro Tyr Lys Arg
1               5                   10
```

<210> SEQ ID NO 89
<211> LENGTH: 13
<212> TYPE: PRT
<213> ORGANISM: Artificial sequence
<220> FEATURE:
<223> OTHER INFORMATION: synthetic amino acid sequence

<400> SEQUENCE: 89

```
Ala Ala Gln Val Ala Phe Leu Lys Ala Ala Thr Lys Ala
1               5                   10
```

<210> SEQ ID NO 90
<211> LENGTH: 13
<212> TYPE: PRT
<213> ORGANISM: Artificial sequence
<220> FEATURE:
<223> OTHER INFORMATION: synthetic amino acid sequence

<400> SEQUENCE: 90

```
Ala Asp Leu Val Ala Phe Phe Lys Glu Ala Ser Lys Arg
1               5                   10
```

<210> SEQ ID NO 91
<211> LENGTH: 13
<212> TYPE: PRT
<213> ORGANISM: Artificial sequence
<220> FEATURE:
<223> OTHER INFORMATION: synthetic amino acid sequence

<400> SEQUENCE: 91

```
Ala Asp Lys Ile Ala Phe Phe Lys Ser Val Thr Lys Lys
1               5                   10
```

<210> SEQ ID NO 92
<211> LENGTH: 13
<212> TYPE: PRT
<213> ORGANISM: Artificial sequence
<220> FEATURE:
<223> OTHER INFORMATION: synthetic amino acid sequence

<400> SEQUENCE: 92

```
Ala Asn Leu Leu Gly Tyr His Lys Val Pro Thr Lys Lys
```

```
1               5                   10

<210> SEQ ID NO 93
<211> LENGTH: 13
<212> TYPE: PRT
<213> ORGANISM: Artificial sequence
<220> FEATURE:
<223> OTHER INFORMATION: synthetic amino acid sequence

<400> SEQUENCE: 93

Ala Asp Pro Val Ala Phe Phe Arg Ser Pro Phe Lys Thr
1               5                   10

<210> SEQ ID NO 94
<211> LENGTH: 13
<212> TYPE: PRT
<213> ORGANISM: Artificial sequence
<220> FEATURE:
<223> OTHER INFORMATION: synthetic amino acid sequence

<400> SEQUENCE: 94

Ala Thr Asp Ile Ala Phe Phe Arg Ala Cys Thr Lys Gly
1               5                   10

<210> SEQ ID NO 95
<211> LENGTH: 13
<212> TYPE: PRT
<213> ORGANISM: Artificial sequence
<220> FEATURE:
<223> OTHER INFORMATION: synthetic amino acid sequence

<400> SEQUENCE: 95

Ala Asn Arg Ile Ala Trp Val Lys Ala Ala Thr Lys Thr
1               5                   10

<210> SEQ ID NO 96
<211> LENGTH: 13
<212> TYPE: PRT
<213> ORGANISM: Artificial sequence
<220> FEATURE:
<223> OTHER INFORMATION: synthetic amino acid sequence

<400> SEQUENCE: 96

Ala Asp Trp Val Gly Trp Phe Lys Ala Ala Thr Lys Gly
1               5                   10

<210> SEQ ID NO 97
<211> LENGTH: 13
<212> TYPE: PRT
<213> ORGANISM: Artificial sequence
<220> FEATURE:
<223> OTHER INFORMATION: synthetic amino acid sequence

<400> SEQUENCE: 97

Ala Asp Trp Ile Ala Tyr Phe Arg Ser Pro Phe Lys Gly
1               5                   10

<210> SEQ ID NO 98
<211> LENGTH: 13
<212> TYPE: PRT
<213> ORGANISM: Artificial sequence
<220> FEATURE:
<223> OTHER INFORMATION: synthetic amino acid sequence

<400> SEQUENCE: 98

Ala Thr Tyr Val Ala Phe Ser Lys Ser Ala Thr Lys Arg
1               5                   10
```

```
<210> SEQ ID NO 99
<211> LENGTH: 12
<212> TYPE: PRT
<213> ORGANISM: Artificial sequence
<220> FEATURE:
<223> OTHER INFORMATION: synthetic amino acid sequence

<400> SEQUENCE: 99

Ala Asp Leu Ile Ala Tyr Leu Lys Gln Ala Thr Lys
1               5                   10

<210> SEQ ID NO 100
<211> LENGTH: 12
<212> TYPE: PRT
<213> ORGANISM: Artificial sequence
<220> FEATURE:
<223> OTHER INFORMATION: synthetic amino acid sequence

<400> SEQUENCE: 100

Ala Asp Pro Leu Ala Phe Phe Ser Ser Ala Ile Lys
1               5                   10

<210> SEQ ID NO 101
<211> LENGTH: 12
<212> TYPE: PRT
<213> ORGANISM: Artificial sequence
<220> FEATURE:
<223> OTHER INFORMATION: synthetic amino acid sequence

<400> SEQUENCE: 101

Ala Thr His Val Ala Phe Leu Lys Ala Ala Thr Lys
1               5                   10

<210> SEQ ID NO 102
<211> LENGTH: 12
<212> TYPE: PRT
<213> ORGANISM: Artificial sequence
<220> FEATURE:
<223> OTHER INFORMATION: synthetic amino acid sequence

<400> SEQUENCE: 102

Ala Asp Ala Ile Ala Phe Phe Ser Ser Ser Leu Lys
1               5                   10

<210> SEQ ID NO 103
<211> LENGTH: 12
<212> TYPE: PRT
<213> ORGANISM: Artificial sequence
<220> FEATURE:
<223> OTHER INFORMATION: synthetic amino acid sequence

<400> SEQUENCE: 103

Ala Asn Gly Val Ala Phe Phe Leu Thr Pro Phe Lys
1               5                   10

<210> SEQ ID NO 104
<211> LENGTH: 12
<212> TYPE: PRT
<213> ORGANISM: Artificial sequence
<220> FEATURE:
<223> OTHER INFORMATION: synthetic amino acid sequence

<400> SEQUENCE: 104

Ala Asp Gly Leu Ala Tyr Phe Arg Ser Ser Phe Lys
1               5                   10
```

```
<210> SEQ ID NO 105
<211> LENGTH: 12
<212> TYPE: PRT
<213> ORGANISM: Artificial sequence
<220> FEATURE:
<223> OTHER INFORMATION: synthetic amino acid sequence

<400> SEQUENCE: 105

Ala Asp Gly Val Gly Phe Phe Val Ser Pro Phe Lys
1               5                   10

<210> SEQ ID NO 106
<211> LENGTH: 12
<212> TYPE: PRT
<213> ORGANISM: Artificial sequence
<220> FEATURE:
<223> OTHER INFORMATION: synthetic amino acid sequence

<400> SEQUENCE: 106

Ala Asn Leu Leu Gly Tyr His Lys Val Pro Thr Lys
1               5                   10

<210> SEQ ID NO 107
<211> LENGTH: 12
<212> TYPE: PRT
<213> ORGANISM: Artificial sequence
<220> FEATURE:
<223> OTHER INFORMATION: synthetic amino acid sequence

<400> SEQUENCE: 107

Ala Asp Gly Val Ala Phe Leu Lys Ala Ala Thr Lys
1               5                   10

<210> SEQ ID NO 108
<211> LENGTH: 190
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (68)..(69)
<223> OTHER INFORMATION: n is a, c, g, or t
<220> FEATURE:
<221> NAME/KEY: misc_feature
<222> LOCATION: (74)..(75)
<223> OTHER INFORMATION: n is a, c, g, or t
<220> FEATURE:
<221> NAME/KEY: misc_feature
<222> LOCATION: (77)..(78)
<223> OTHER INFORMATION: n is a, c, g, or t
<220> FEATURE:
<221> NAME/KEY: misc_feature
<222> LOCATION: (80)..(81)
<223> OTHER INFORMATION: n is a, c, g, or t
<220> FEATURE:
<221> NAME/KEY: misc_feature
<222> LOCATION: (83)..(84)
<223> OTHER INFORMATION: n is a, c, g, or t
<220> FEATURE:
<221> NAME/KEY: misc_feature
<222> LOCATION: (86)..(87)
<223> OTHER INFORMATION: n is a, c, g, or t
<220> FEATURE:
<221> NAME/KEY: misc_feature
<222> LOCATION: (89)..(90)
<223> OTHER INFORMATION: n is a, c, g, or t
<220> FEATURE:
<221> NAME/KEY: misc_feature
<222> LOCATION: (92)..(93)
<223> OTHER INFORMATION: n is a, c, g, or t
<220> FEATURE:
```

```
<221> NAME/KEY: misc_feature
<222> LOCATION: (95)..(96)
<223> OTHER INFORMATION: n is a, c, g, or t

<400> SEQUENCE: 108
attttcaatt aagatgcagt tacttcgctg tttttcaata ttttctgtta ttgctagcgt    60
tttggctnnk dcknnknnkn nknnknnknn knnknnktwy ggtggaggag gttctggagg   120
tggtggtagt ggtggtggtg gttccataca aagaactcca aagatccaag tttacagtag   180
acatcctgct                                                          190

<210> SEQ ID NO 109
<211> LENGTH: 63
<212> TYPE: PRT
<213> ORGANISM: Artificial sequence
<220> FEATURE:
<223> OTHER INFORMATION: synthetic amino acid sequence
<220> FEATURE:
<221> NAME/KEY: misc_feature
<222> LOCATION: (23)..(33)
<223> OTHER INFORMATION: Xaa can be any naturally occurring amino acid

<400> SEQUENCE: 109

Phe Ser Ile Lys Met Gln Leu Leu Arg Cys Phe Ser Ile Phe Ser Val
1               5                   10                  15

Ile Ala Ser Val Leu Ala Xaa Xaa Xaa Xaa Xaa Xaa Xaa Xaa Xaa
            20                  25                  30

Xaa Gly Gly Gly Gly Ser Gly Gly Gly Ser Gly Gly Gly Gly Ser
        35                  40                  45

Ile Gln Arg Thr Pro Lys Ile Gln Val Tyr Ser Arg His Pro Ala
    50                  55                  60

<210> SEQ ID NO 110
<211> LENGTH: 11
<212> TYPE: PRT
<213> ORGANISM: Human immunodeficiency virus

<400> SEQUENCE: 110

Lys Ala Phe Ser Pro Glu Val Ile Pro Met Phe
1               5                   10

<210> SEQ ID NO 111
<211> LENGTH: 8
<212> TYPE: PRT
<213> ORGANISM: Artificial sequence
<220> FEATURE:
<223> OTHER INFORMATION: synthetic amino acid sequence

<400> SEQUENCE: 111

Asp Tyr Lys Asp Asp Asp Asp Lys
1               5

<210> SEQ ID NO 112
<211> LENGTH: 4
<212> TYPE: PRT
<213> ORGANISM: Artificial sequence
<220> FEATURE:
<223> OTHER INFORMATION: synthetic amino acid sequence

<400> SEQUENCE: 112

Ala Asp Asn Thr
1

<210> SEQ ID NO 113
```

```
<211> LENGTH: 6
<212> TYPE: PRT
<213> ORGANISM: Artificial sequence
<220> FEATURE:
<223> OTHER INFORMATION: synthetic amino acid sequence

<400> SEQUENCE: 113

Ala Glu Gly Lys Arg Thr
1               5

<210> SEQ ID NO 114
<211> LENGTH: 21
<212> TYPE: DNA
<213> ORGANISM: Artificial sequence
<220> FEATURE:
<223> OTHER INFORMATION: synthetic polynucleotide sequence

<400> SEQUENCE: 114
atgcaaaaac tgcataacca c                                              21

<210> SEQ ID NO 115
<211> LENGTH: 22
<212> TYPE: DNA
<213> ORGANISM: Artificial sequence
<220> FEATURE:
<223> OTHER INFORMATION: synthetic polynucleotide sequence

<400> SEQUENCE: 115
gggatttgct cgcatatagt tg                                             22

<210> SEQ ID NO 116
<211> LENGTH: 77
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t

<400> SEQUENCE: 116
tattgctagc gttttagcag ctrmtnnkvt tnnknnknnk nnknnknnkn nkaaarvagg    60
```
cggtggttcg ggcggtg                                                      77

<210> SEQ ID NO 117
<211> LENGTH: 24
<212> TYPE: DNA
<213> ORGANISM: Artificial sequence
<220> FEATURE:
<223> OTHER INFORMATION: synthetic polynucleotide sequence

<400> SEQUENCE: 117
cgtcatcatc tttataatcg gatc                                              24

<210> SEQ ID NO 118
<211> LENGTH: 67
<212> TYPE: DNA
<213> ORGANISM: Artificial sequence
<220> FEATURE:
<223> OTHER INFORMATION: synthetic polynucleotide sequence

<400> SEQUENCE: 118
ttcaattaag atgcagttac ttcgctgttt ttcaatattt tctgttattg ctagcgtttt       60
agcagct                                                                 67

<210> SEQ ID NO 119
<211> LENGTH: 50
<212> TYPE: DNA
<213> ORGANISM: Artificial sequence
<220> FEATURE:
<223> OTHER INFORMATION: synthetic polynucleotide sequence

<400> SEQUENCE: 119
accaccagat ccaccaccac ctttatcgtc atcatcttta taatcggatc                  50

<210> SEQ ID NO 120
<211> LENGTH: 84
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t

```
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (61)..(62)
<223> OTHER INFORMATION: n is a, c, g, or t

<400> SEQUENCE: 120
gttattgcta gcgtattggc cnnknnknnk nnkvtannkn nktwtnnknn knnknnknnk      60
nnkagaggtg gtggtggttc aggt                                            84

<210> SEQ ID NO 121
<211> LENGTH: 64
<212> TYPE: DNA
<213> ORGANISM: Artificial sequence
<220> FEATURE:
<223> OTHER INFORMATION: synthetic polynucleotide sequence

<400> SEQUENCE: 121
ttcaattaag atgcagttac ttcgctgttt ttcaatattt tctgttattg ctagcgtatt     60
ggcc                                                                 64

<210> SEQ ID NO 122
<211> LENGTH: 51
<212> TYPE: DNA
<213> ORGANISM: Artificial sequence
<220> FEATURE:
<223> OTHER INFORMATION: synthetic polynucleotide sequence

<400> SEQUENCE: 122
accgccacca ccagatccac caccacccaa gtcttcttca gaaataagct t              51

<210> SEQ ID NO 123
<211> LENGTH: 84
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (41)..(41)
```

<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (61)..(62)
<223> OTHER INFORMATION: n is a, c, g, or t

<400> SEQUENCE: 123
gttattgcta gcgtattggc cnnknnknnk nnkvtadnkv nktwtbnknn knnknnknnk    60
nnkagaggtg gtggtggttc aggt                                          84

<210> SEQ ID NO 124
<211> LENGTH: 84
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (61)..(62)
<223> OTHER INFORMATION: n is a, c, g, or t

<400> SEQUENCE: 124
gttattgcta gcgtattggc cnnknnknnk nnkvtadnkv nktwtnbknn knnknnknnk    60
nnkagaggtg gtggtggttc aggt                                          84

<210> SEQ ID NO 125
<211> LENGTH: 84
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (61)..(62)
<223> OTHER INFORMATION: n is a, c, g, or t

<400> SEQUENCE: 125
gttattgcta gcgtattggc cnnknnknnk nnkvtadnkn vktwtbnknn knnknnknnk    60
nnkagaggtg gtggtggttc aggt                                          84

<210> SEQ ID NO 126

```
<211> LENGTH: 84
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (61)..(62)
<223> OTHER INFORMATION: n is a, c, g, or t

<400> SEQUENCE: 126
gttattgcta gcgtattggc cnnknnknnk nnkvtadnkn vktwtnbknn knnknnknnk      60
nnkagaggtg gtggtggttc aggt                                            84

<210> SEQ ID NO 127
<211> LENGTH: 84
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
```

```
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (61)..(62)
<223> OTHER INFORMATION: n is a, c, g, or t

<400> SEQUENCE: 127
gttattgcta gcgtattggc cnnknnknnk nnkvtanbkv nktwtbnknn knnknnknnk      60
nnkagaggtg gtggtggttc aggt                                            84

<210> SEQ ID NO 128
<211> LENGTH: 84
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t
<220> FEATURE:
```

```
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (61)..(62)
<223> OTHER INFORMATION: n is a, c, g, or t

<400> SEQUENCE: 128
gttattgcta gcgtattggc cnnknnknnk nnkvtanbkv nktwtnbknn knnknnknnk        60
nnkagaggtg gtggtggttc aggt                                              84

<210> SEQ ID NO 129
<211> LENGTH: 84
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
```

<222> LOCATION: (61)..(62)
<223> OTHER INFORMATION: n is a, c, g, or t

<400> SEQUENCE: 129
gttattgcta gcgtattggc cnnknnknnk nnkvtanbkn vktwtbnknn knnknnknnk    60
nnkagaggtg gtggtggttc aggt    84

<210> SEQ ID NO 130
<211> LENGTH: 84
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (61)..(62)
<223> OTHER INFORMATION: n is a, c, g, or t

<400> SEQUENCE: 130
gttattgcta gcgtattggc cnnknnknnk nnkvtanbkn vktwtnbknn knnknnknnk    60
nnkagaggtg gtggtggttc aggt    84

<210> SEQ ID NO 131
<211> LENGTH: 84
<212> TYPE: DNA
<213> ORGANISM: Artificial sequence
<220> FEATURE:
<223> OTHER INFORMATION: synthetic polynucleotide sequence
<220> FEATURE:

```
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (61)..(62)
<223> OTHER INFORMATION: n is a, c, g, or t

<400> SEQUENCE: 131
gttattgcta gcgtattggc cnnknnknnk nnkrtacatt tctttarann knnknnknnk    60
nnkagaggtg gtggtggttc aggt                                          84

<210> SEQ ID NO 132
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 132
ctacacgacg ctcttccgat ctnnnnnnnn atcacgctgt tattgctagc gttttagca    59

<210> SEQ ID NO 133
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 133
ctacacgacg ctcttccgat ctnnnnnnnn cgatgtctgt tattgctagc gttttagca    59

<210> SEQ ID NO 134
<211> LENGTH: 59
<212> TYPE: DNA
<213> ORGANISM: Artificial sequence
```

```
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 134
ctacacgacg ctcttccgat ctnnnnnnnn ttaggcctgt tattgctagc gttttagca      59

<210> SEQ ID NO 135
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 135
ctacacgacg ctcttccgat ctnnnnnnnn tgaccactgt tattgctagc gttttagca      59

<210> SEQ ID NO 136
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 136
ctacacgacg ctcttccgat ctnnnnnnnn acagtgctgt tattgctagc gttttagca      59

<210> SEQ ID NO 137
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 137
ctacacgacg ctcttccgat ctnnnnnnnn ggctacctgt tattgctagc gttttagca      59

<210> SEQ ID NO 138
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 138
ctacacgacg ctcttccgat ctnnnnnnnn cttgtactgt tattgctagc gttttagca      59

<210> SEQ ID NO 139
<211> LENGTH: 59
<212> TYPE: DNA
```

```
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 139
ctacacgacg ctcttccgat ctnnnnnnnn agtcaactgt tattgctagc gttttagca      59

<210> SEQ ID NO 140
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 140
ctacacgacg ctcttccgat ctnnnnnnnn agttccctgt tattgctagc gttttagca      59

<210> SEQ ID NO 141
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 141
ctacacgacg ctcttccgat ctnnnnnnnn atgtcactgt tattgctagc gttttagca      59

<210> SEQ ID NO 142
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 142
ctacacgacg ctcttccgat ctnnnnnnnn ccgtccctgt tattgctagc gttttagca      59

<210> SEQ ID NO 143
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 143
ctacacgacg ctcttccgat ctnnnnnnnn gtagagctgt tattgctagc gttttagca      59

<210> SEQ ID NO 144
<211> LENGTH: 59
```

```
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 144
ctacacgacg ctcttccgat ctnnnnnnnn gtccgcctgt tattgctagc gttttagca      59

<210> SEQ ID NO 145
<211> LENGTH: 59
<212> TYPE: DNA
<213> ORGANISM: Artificial sequence
<220> FEATURE:
<223> OTHER INFORMATION: synthetic amino acid sequence
<220> FEATURE:
<221> NAME/KEY: misc_feature
<222> LOCATION: (23)..(30)
<223> OTHER INFORMATION: n is a, c, g, or t

<400> SEQUENCE: 145
ctacacgacg ctcttccgat ctnnnnnnnn gtgaaactgt tattgctagc gttttagca      59

<210> SEQ ID NO 146
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 146
ctacacgacg ctcttccgat ctnnnnnnnn gtggccctgt tattgctagc gttttagca      59

<210> SEQ ID NO 147
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 147
ctacacgacg ctcttccgat ctnnnnnnnn gttcgctgt tattgctagc gttttagca       59

<210> SEQ ID NO 148
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 148
ctacacgacg ctcttccgat ctnnnnnnnn cgtacgctgt tattgctagc gttttagca      59

<210> SEQ ID NO 149
```

```
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 149
ctacacgacg ctcttccgat ctnnnnnnnn gagtggctgt tattgctagc gttttagca      59

<210> SEQ ID NO 150
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 150
ctacacgacg ctcttccgat ctnnnnnnnn ggtagcctgt tattgctagc gttttagca      59

<210> SEQ ID NO 151
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 151
ctacacgacg ctcttccgat ctnnnnnnnn atgagcctgt tattgctagc gttttagca      59

<210> SEQ ID NO 152
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 152
ctacacgacg ctcttccgat ctnnnnnnnn attcctctgt tattgctagc gttttagca      59

<210> SEQ ID NO 153
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 153
ctacacgacg ctcttccgat ctnnnnnnnn caaaagctgt tattgctagc gttttagca      59
```

```
<210> SEQ ID NO 154
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 154
ctacacgacg ctcttccgat ctnnnnnnnn caactactgt tattgctagc gttttagca       59

<210> SEQ ID NO 155
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 155
ctacacgacg ctcttccgat ctnnnnnnnn cacgatctgt tattgctagc gttttagca       59

<210> SEQ ID NO 156
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 156
ctacacgacg ctcttccgat ctnnnnnnnn cactcactgt tattgctagc gttttagca       59

<210> SEQ ID NO 157
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 157
ctacacgacg ctcttccgat ctnnnnnnnn caggcgctgt tattgctagc gttttagca       59

<210> SEQ ID NO 158
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 158
ctacacgacg ctcttccgat ctnnnnnnnn catggcctgt tattgctagc gttttagca       59
```

```
<210> SEQ ID NO 159
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 159
ctacacgacg ctcttccgat ctnnnnnnnn cattttctgt tattgctagc gttttagca      59

<210> SEQ ID NO 160
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 160
ctacacgacg ctcttccgat ctnnnnnnnn cggaatctgt tattgctagc gttttagca      59

<210> SEQ ID NO 161
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 161
ctacacgacg ctcttccgat ctnnnnnnnn ctagctctgt tattgctagc gttttagca      59

<210> SEQ ID NO 162
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 162
ctacacgacg ctcttccgat ctnnnnnnnn ctatacctgt tattgctagc gttttagca      59

<210> SEQ ID NO 163
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 163
ctacacgacg ctcttccgat ctnnnnnnnn ctcagactgt tattgctagc gttttagca      59
```

<210> SEQ ID NO 164
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 164
ctacacgacg ctcttccgat ctnnnnnnnn tacagcctgt tattgctagc gttttagca    59

<210> SEQ ID NO 165
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 165
ctacacgacg ctcttccgat ctnnnnnnnn tataatctgt tattgctagc gttttagca    59

<210> SEQ ID NO 166
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 166
ctacacgacg ctcttccgat ctnnnnnnnn tcattcctgt tattgctagc gttttagca    59

<210> SEQ ID NO 167
<211> LENGTH: 59
<212> TYPE: DNA
<213> ORGANISM: Artificial sequence
<220> FEATURE:
<223> OTHER INFORMATION: synthetic amino acid sequence
<220> FEATURE:
<221> NAME/KEY: misc_feature
<222> LOCATION: (23)..(30)
<223> OTHER INFORMATION: n is a, c, g, or t

<400> SEQUENCE: 167
ctacacgacg ctcttccgat ctnnnnnnnn tcccgactgt tattgctagc gttttagca    59

<210> SEQ ID NO 168
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 168
ctacacgacg ctcttccgat ctnnnnnnnn tcgaagctgt tattgctagc gttttagca    59

<210> SEQ ID NO 169
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 169
ctacacgacg ctcttccgat ctnnnnnnnn tcggcactgt tattgctagc gttttagca    59

<210> SEQ ID NO 170
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 170
ctacacgacg ctcttccgat ctnnnnnnnn aaacacctgt tattgctagc gttttagca    59

<210> SEQ ID NO 171
<211> LENGTH: 54
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (22)..(29)
<223> OTHER INFORMATION: n is a, c, g, or t

<400> SEQUENCE: 171
gctgaaccgc tcttccgatc tnnnnnnnna actctttgag taccattata gaaa          54

<210> SEQ ID NO 172
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 172
ctacacgacg ctcttccgat ctnnnnnnnn atcacgctgt tattgctagc gtattggcc    59

<210> SEQ ID NO 173
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 173
ctacacgacg ctcttccgat ctnnnnnnnn cgatgtctgt tattgctagc gtattggcc     59

<210> SEQ ID NO 174
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 174
ctacacgacg ctcttccgat ctnnnnnnnn ttaggcctgt tattgctagc gtattggcc     59

<210> SEQ ID NO 175
<211> LENGTH: 59
<212> TYPE: DNA
<213> ORGANISM: Artificial sequence
<220> FEATURE:
<223> OTHER INFORMATION: synthetic amino acid sequence
<220> FEATURE:
<221> NAME/KEY: misc_feature
<222> LOCATION: (23)..(30)
<223> OTHER INFORMATION: n is a, c, g, or t

<400> SEQUENCE: 175
ctacacgacg ctcttccgat ctnnnnnnnn tgaccactgt tattgctagc gtattggcc     59

<210> SEQ ID NO 176
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 176
ctacacgacg ctcttccgat ctnnnnnnnn acagtgctgt tattgctagc gtattggcc     59

<210> SEQ ID NO 177
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 177
ctacacgacg ctcttccgat ctnnnnnnnn ggctacctgt tattgctagc gtattggcc     59

<210> SEQ ID NO 178
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 178
ctacacgacg ctcttccgat ctnnnnnnnn cttgtactgt tattgctagc gtattggcc    59

<210> SEQ ID NO 179
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 179
ctacacgacg ctcttccgat ctnnnnnnnn agtcaactgt tattgctagc gtattggcc    59

<210> SEQ ID NO 180
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 180
ctacacgacg ctcttccgat ctnnnnnnnn agttccctgt tattgctagc gtattggcc    59

<210> SEQ ID NO 181
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 181
ctacacgacg ctcttccgat ctnnnnnnnn atgtcactgt tattgctagc gtattggcc    59

<210> SEQ ID NO 182
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 182
ctacacgacg ctcttccgat ctnnnnnnnn ccgtccctgt tattgctagc gtattggcc    59

<210> SEQ ID NO 183
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 183
ctacacgacg ctcttccgat ctnnnnnnnn gtagagctgt tattgctagc gtattggcc    59

<210> SEQ ID NO 184
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 184
ctacacgacg ctcttccgat ctnnnnnnnn gtccgctgt tattgctagc gtattggcc    59

<210> SEQ ID NO 185
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 185
ctacacgacg ctcttccgat ctnnnnnnnn gtgaaactgt tattgctagc gtattggcc    59

<210> SEQ ID NO 186
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 186
ctacacgacg ctcttccgat ctnnnnnnnn gtggccctgt tattgctagc gtattggcc    59

<210> SEQ ID NO 187
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 187
ctacacgacg ctcttccgat ctnnnnnnnn gtttcgctgt tattgctagc gtattggcc    59

<210> SEQ ID NO 188
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)

<223> OTHER INFORMATION: n is a, c, g, or t

<400> SEQUENCE: 188
ctacacgacg ctcttccgat ctnnnnnnnn cgtacgctgt tattgctagc gtattggcc      59

<210> SEQ ID NO 189
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 189
ctacacgacg ctcttccgat ctnnnnnnnn gagtggctgt tattgctagc gtattggcc      59

<210> SEQ ID NO 190
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 190
ctacacgacg ctcttccgat ctnnnnnnnn ggtagcctgt tattgctagc gtattggcc      59

<210> SEQ ID NO 191
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 191
ctacacgacg ctcttccgat ctnnnnnnnn atgagcctgt tattgctagc gtattggcc      59

<210> SEQ ID NO 192
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 192
ctacacgacg ctcttccgat ctnnnnnnnn attcctctgt tattgctagc gtattggcc      59

<210> SEQ ID NO 193
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 193
ctacacgacg ctcttccgat ctnnnnnnnn caaaagctgt tattgctagc gtattggcc      59

<210> SEQ ID NO 194
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 194
ctacacgacg ctcttccgat ctnnnnnnnn caactactgt tattgctagc gtattggcc      59

<210> SEQ ID NO 195
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 195
ctacacgacg ctcttccgat ctnnnnnnnn cacgatctgt tattgctagc gtattggcc      59

<210> SEQ ID NO 196
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 196
ctacacgacg ctcttccgat ctnnnnnnnn cactcactgt tattgctagc gtattggcc      59

<210> SEQ ID NO 197
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 197
ctacacgacg ctcttccgat ctnnnnnnnn caggcgctgt tattgctagc gtattggcc      59

<210> SEQ ID NO 198
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:

<221> NAME/KEY: misc_feature
<222> LOCATION: (23)..(30)
<223> OTHER INFORMATION: n is a, c, g, or t

<400> SEQUENCE: 198
ctacacgacg ctcttccgat ctnnnnnnnn catggcctgt tattgctagc gtattggcc    59

<210> SEQ ID NO 199
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 199
ctacacgacg ctcttccgat ctnnnnnnnn cattttctgt tattgctagc gtattggcc    59

<210> SEQ ID NO 200
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 200
ctacacgacg ctcttccgat ctnnnnnnnn cggaatctgt tattgctagc gtattggcc    59

<210> SEQ ID NO 201
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 201
ctacacgacg ctcttccgat ctnnnnnnnn ctagctctgt tattgctagc gtattggcc    59

<210> SEQ ID NO 202
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 202
ctacacgacg ctcttccgat ctnnnnnnnn ctatacctgt tattgctagc gtattggcc    59

<210> SEQ ID NO 203
<211> LENGTH: 59
<212> TYPE: DNA
<213> ORGANISM: Artificial sequence
<220> FEATURE:
<223> OTHER INFORMATION: synthetic polynucleotide sequence

```
<220> FEATURE:
<221> NAME/KEY: misc_feature
<222> LOCATION: (23)..(30)
<223> OTHER INFORMATION: n is a, c, g, or t

<400> SEQUENCE: 203
ctacacgacg ctcttccgat ctnnnnnnnn ctcagactgt tattgctagc gtattggcc      59

<210> SEQ ID NO 204
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 204
ctacacgacg ctcttccgat ctnnnnnnnn tacagcctgt tattgctagc gtattggcc      59

<210> SEQ ID NO 205
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 205
ctacacgacg ctcttccgat ctnnnnnnnn tataatctgt tattgctagc gtattggcc      59

<210> SEQ ID NO 206
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 206
ctacacgacg ctcttccgat ctnnnnnnnn tcattcctgt tattgctagc gtattggcc      59

<210> SEQ ID NO 207
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 207
ctacacgacg ctcttccgat ctnnnnnnnn tcccgactgt tattgctagc gtattggcc      59

<210> SEQ ID NO 208
<211> LENGTH: 59
<212> TYPE: DNA
<213> ORGANISM: Artificial sequence
<220> FEATURE:
```

<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 208
ctacacgacg ctcttccgat ctnnnnnnnn tcgaagctgt tattgctagc gtattggcc        59

<210> SEQ ID NO 209
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 209
ctacacgacg ctcttccgat ctnnnnnnnn tcggcactgt tattgctagc gtattggcc        59

<210> SEQ ID NO 210
<211> LENGTH: 59
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (23)..(30)
<223> OTHER INFORMATION: n is a, c, g, or t

<400> SEQUENCE: 210
ctacacgacg ctcttccgat ctnnnnnnnn aaacacctgt tattgctagc gtattggcc        59

<210> SEQ ID NO 211
<211> LENGTH: 50
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (22)..(29)
<223> OTHER INFORMATION: n is a, c, g, or t

<400> SEQUENCE: 211
gctgaaccgc tcttccgatc tnnnnnnnnc gttgaaaaag tgacattctc                  50

<210> SEQ ID NO 212
<211> LENGTH: 58
<212> TYPE: DNA
<213> ORGANISM: Artificial sequence
<220> FEATURE:
<223> OTHER INFORMATION: synthetic polynucleotide sequence

<400> SEQUENCE: 212
aatgatacgg cgaccaccga gatctacact ctttccctac acgacgctct tccgatct         58

<210> SEQ ID NO 213
<211> LENGTH: 60
<212> TYPE: DNA
<213> ORGANISM: Artificial sequence
<220> FEATURE:
<223> OTHER INFORMATION: synthetic polynucleotide sequence

<400> SEQUENCE: 213

```
caagcagaag acggcatacg agatcggtct cggcattcct gctgaaccgc tcttccgatc    60
```

<210> SEQ ID NO 214
<211> LENGTH: 11
<212> TYPE: PRT
<213> ORGANISM: Artificial sequence
<220> FEATURE:
<223> OTHER INFORMATION: synthetic amino acid sequence

<400> SEQUENCE: 214

Asn Ser Leu Lys Pro Glu Ile Pro Asp Tyr Phe
1               5                   10

<210> SEQ ID NO 215
<211> LENGTH: 11
<212> TYPE: PRT
<213> ORGANISM: Artificial sequence
<220> FEATURE:
<223> OTHER INFORMATION: synthetic amino acid sequence

<400> SEQUENCE: 215

Gly Thr Ile Arg Pro Glu Ile Arg Glu Met Trp
1               5                   10

<210> SEQ ID NO 216
<211> LENGTH: 11
<212> TYPE: PRT
<213> ORGANISM: Artificial sequence
<220> FEATURE:
<223> OTHER INFORMATION: synthetic amino acid sequence

<400> SEQUENCE: 216

Ser Ser Gly Val Pro Glu Val Arg Met Met Phe
1               5                   10

<210> SEQ ID NO 217
<211> LENGTH: 11
<212> TYPE: PRT
<213> ORGANISM: Artificial sequence
<220> FEATURE:
<223> OTHER INFORMATION: synthetic amino acid sequence

<400> SEQUENCE: 217

Leu Ser Leu Arg Pro Glu Ile Pro Leu Phe Phe
1               5                   10

<210> SEQ ID NO 218
<211> LENGTH: 11
<212> TYPE: PRT
<213> ORGANISM: Artificial sequence
<220> FEATURE:
<223> OTHER INFORMATION: synthetic amino acid sequence

<400> SEQUENCE: 218

Lys Ser Phe Val Pro Glu Leu Lys Pro Ala Phe
1               5                   10

<210> SEQ ID NO 219
<211> LENGTH: 11
<212> TYPE: PRT
<213> ORGANISM: Artificial sequence
<220> FEATURE:
<223> OTHER INFORMATION: synthetic amino acid sequence

<400> SEQUENCE: 219

Trp Thr Tyr Arg Pro Glu Val Arg Gly Val Trp

-continued

```
1               5                   10

<210> SEQ ID NO 220
<211> LENGTH: 11
<212> TYPE: PRT
<213> ORGANISM: Artificial sequence
<220> FEATURE:
<223> OTHER INFORMATION: synthetic amino acid sequence

<400> SEQUENCE: 220

Arg Ser Phe Tyr Pro Glu Ile Arg Glu Tyr Trp
1               5                   10

<210> SEQ ID NO 221
<211> LENGTH: 11
<212> TYPE: PRT
<213> ORGANISM: Artificial sequence
<220> FEATURE:
<223> OTHER INFORMATION: synthetic amino acid sequence

<400> SEQUENCE: 221

Ser Ser Phe Ser Pro Glu Leu Arg Met Arg Trp
1               5                   10

<210> SEQ ID NO 222
<211> LENGTH: 11
<212> TYPE: PRT
<213> ORGANISM: Artificial sequence
<220> FEATURE:
<223> OTHER INFORMATION: synthetic amino acid sequence

<400> SEQUENCE: 222

Lys Ser Cys Thr Pro Glu Val Arg Glu Tyr Phe
1               5                   10

<210> SEQ ID NO 223
<211> LENGTH: 11
<212> TYPE: PRT
<213> ORGANISM: Artificial sequence
<220> FEATURE:
<223> OTHER INFORMATION: synthetic amino acid sequence

<400> SEQUENCE: 223

Ala Ser Phe Ser Pro Glu Leu Arg Met Ala Trp
1               5                   10

<210> SEQ ID NO 224
<211> LENGTH: 11
<212> TYPE: PRT
<213> ORGANISM: Artificial sequence
<220> FEATURE:
<223> OTHER INFORMATION: synthetic amino acid sequence

<400> SEQUENCE: 224

Lys Ser Leu Ala Pro Glu Val Arg Asp Leu Phe
1               5                   10

<210> SEQ ID NO 225
<211> LENGTH: 11
<212> TYPE: PRT
<213> ORGANISM: Artificial sequence
<220> FEATURE:
<223> OTHER INFORMATION: synthetic amino acid sequence

<400> SEQUENCE: 225

Asn Ser Val Lys Pro Glu Ile Arg Pro Val Trp
1               5                   10
```

```
<210> SEQ ID NO 226
<211> LENGTH: 11
<212> TYPE: PRT
<213> ORGANISM: Artificial sequence
<220> FEATURE:
<223> OTHER INFORMATION: synthetic amino acid sequence

<400> SEQUENCE: 226

Asn Ser Phe Arg Pro Glu Val Ala Met Lys Tyr
1               5                   10

<210> SEQ ID NO 227
<211> LENGTH: 11
<212> TYPE: PRT
<213> ORGANISM: Artificial sequence
<220> FEATURE:
<223> OTHER INFORMATION: synthetic amino acid sequence

<400> SEQUENCE: 227

Lys Ser Leu Thr Pro Glu Val Arg Gly Tyr Trp
1               5                   10

<210> SEQ ID NO 228
<211> LENGTH: 11
<212> TYPE: PRT
<213> ORGANISM: Artificial sequence
<220> FEATURE:
<223> OTHER INFORMATION: synthetic amino acid sequence

<400> SEQUENCE: 228

Tyr Ser Phe Lys Pro Glu Leu Lys Glu Ile Phe
1               5                   10

<210> SEQ ID NO 229
<211> LENGTH: 11
<212> TYPE: PRT
<213> ORGANISM: Artificial sequence
<220> FEATURE:
<223> OTHER INFORMATION: synthetic amino acid sequence

<400> SEQUENCE: 229

Ala Ser Phe Arg Pro Glu Leu Ala Glu Phe Trp
1               5                   10

<210> SEQ ID NO 230
<211> LENGTH: 11
<212> TYPE: PRT
<213> ORGANISM: Artificial sequence
<220> FEATURE:
<223> OTHER INFORMATION: synthetic amino acid sequence

<400> SEQUENCE: 230

Gly Ser Leu Ala Pro Glu Ile Arg Met Tyr Trp
1               5                   10

<210> SEQ ID NO 231
<211> LENGTH: 11
<212> TYPE: PRT
<213> ORGANISM: Artificial sequence
<220> FEATURE:
<223> OTHER INFORMATION: synthetic amino acid sequence

<400> SEQUENCE: 231

Arg Ser Phe Val Pro Glu Ile Gly Met Gly Phe
1               5                   10
```

<210> SEQ ID NO 232
<211> LENGTH: 11
<212> TYPE: PRT
<213> ORGANISM: Artificial sequence
<220> FEATURE:
<223> OTHER INFORMATION: synthetic amino acid sequence

<400> SEQUENCE: 232

Ser Ala Leu Arg Pro Glu Ile Arg Leu Leu Trp
1               5                   10

<210> SEQ ID NO 233
<211> LENGTH: 11
<212> TYPE: PRT
<213> ORGANISM: Human immunodeficiency virus 1
<220> FEATURE:
<221> NAME/KEY: misc_feature
<222> LOCATION: (8)..(9)
<223> OTHER INFORMATION: Xaa can be any naturally occurring amino acid

<400> SEQUENCE: 233

Lys Ala Phe Ser Pro Glu Val Xaa Xaa Met Phe
1               5                   10

<210> SEQ ID NO 234
<211> LENGTH: 11
<212> TYPE: PRT
<213> ORGANISM: Human immunodeficiency virus 1

<400> SEQUENCE: 234

Arg Ala Phe Ser Pro Glu Val Leu Pro Met Phe
1               5                   10

<210> SEQ ID NO 235
<211> LENGTH: 11
<212> TYPE: PRT
<213> ORGANISM: Human immunodeficiency virus 1

<400> SEQUENCE: 235

Lys Ala Phe Ser Pro Glu Val Leu Pro Met Phe
1               5                   10

<210> SEQ ID NO 236
<211> LENGTH: 11
<212> TYPE: PRT
<213> ORGANISM: Human immunodeficiency virus 1

<400> SEQUENCE: 236

Lys Ala Phe Ser Pro Glu Val Gly Pro Met Phe
1               5                   10

<210> SEQ ID NO 237
<211> LENGTH: 11
<212> TYPE: PRT
<213> ORGANISM: Human immunodeficiency virus 1
<220> FEATURE:
<221> NAME/KEY: misc_feature
<222> LOCATION: (8)..(8)
<223> OTHER INFORMATION: Xaa can be any naturally occurring amino acid

<400> SEQUENCE: 237

Lys Ala Phe Ser Pro Glu Val Xaa Pro Met Phe
1               5                   10

<210> SEQ ID NO 238
<211> LENGTH: 11

```
<212> TYPE: PRT
<213> ORGANISM: Human immunodeficiency virus 1

<400> SEQUENCE: 238

Lys Ala Phe Ser Pro Glu Val Lys Pro Met Phe
1               5                   10

<210> SEQ ID NO 239
<211> LENGTH: 11
<212> TYPE: PRT
<213> ORGANISM: Olsenella uli

<400> SEQUENCE: 239

Arg Ser Leu Ala Pro Glu Val Arg Gly Tyr Trp
1               5                   10

<210> SEQ ID NO 240
<211> LENGTH: 11
<212> TYPE: PRT
<213> ORGANISM: Canis lupus familiaris

<400> SEQUENCE: 240

Trp Thr Ser Ser Pro Glu Ile Arg Ala Val Phe
1               5                   10

<210> SEQ ID NO 241
<211> LENGTH: 11
<212> TYPE: PRT
<213> ORGANISM: Polaromonas sp. CF318

<400> SEQUENCE: 241

Ala Ser Ser Arg Pro Glu Leu Ala Leu Ala Tyr
1               5                   10

<210> SEQ ID NO 242
<211> LENGTH: 11
<212> TYPE: PRT
<213> ORGANISM: Ricciocarpos natans

<400> SEQUENCE: 242

Trp Thr Ser His Pro Glu Ile Lys Ala Ala Phe
1               5                   10

<210> SEQ ID NO 243
<211> LENGTH: 11
<212> TYPE: PRT
<213> ORGANISM: Thermobacillus composti KWC4

<400> SEQUENCE: 243

Arg Ser Leu Lys Pro Glu Val Arg Glu Val Phe
1               5                   10

<210> SEQ ID NO 244
<211> LENGTH: 11
<212> TYPE: PRT
<213> ORGANISM: Streptomyces coelicoflavus

<400> SEQUENCE: 244

Ala Ser Leu Arg Pro Glu Val Arg Glu Ala Phe
1               5                   10

<210> SEQ ID NO 245
<211> LENGTH: 11
<212> TYPE: PRT
<213> ORGANISM: Coleofasciculus chthonoplastes
```

<400> SEQUENCE: 245

Lys Ser Leu Tyr Pro Glu Ile Arg Glu Val Phe
1               5                   10

<210> SEQ ID NO 246
<211> LENGTH: 11
<212> TYPE: PRT
<213> ORGANISM: Janibacter sp. HTCC2649

<400> SEQUENCE: 246

Leu Ser Gly Val Pro Glu Ile Arg Glu Arg Trp
1               5                   10

<210> SEQ ID NO 247
<211> LENGTH: 11
<212> TYPE: PRT
<213> ORGANISM: Opitutaceae bacterium TAV5

<400> SEQUENCE: 247

Leu Thr Ile Arg Pro Glu Ile Arg Pro Arg Trp
1               5                   10

<210> SEQ ID NO 248
<211> LENGTH: 11
<212> TYPE: PRT
<213> ORGANISM: Leptonema illini

<400> SEQUENCE: 248

Ala Ser Phe Lys Pro Glu Leu Pro Asp Phe Phe
1               5                   10

<210> SEQ ID NO 249
<211> LENGTH: 11
<212> TYPE: PRT
<213> ORGANISM: Rhizobium sp.

<400> SEQUENCE: 249

Ser Thr Ile Ser Pro Glu Ile Arg Leu Phe Trp
1               5                   10

<210> SEQ ID NO 250
<211> LENGTH: 11
<212> TYPE: PRT
<213> ORGANISM: Eutypa lata UCREL1

<400> SEQUENCE: 250

Ala Ser Leu Lys Pro Glu Val Pro Leu Val Phe
1               5                   10

<210> SEQ ID NO 251
<211> LENGTH: 11
<212> TYPE: PRT
<213> ORGANISM: Herbaspirillum sp. CF444

<400> SEQUENCE: 251

Ser Ser Gly Ala Pro Glu Val Arg Glu Leu Phe
1               5                   10

<210> SEQ ID NO 252
<211> LENGTH: 11
<212> TYPE: PRT
<213> ORGANISM: Phytophthora infestans T30-4

<400> SEQUENCE: 252

Ser Ser Val Val Pro Glu Leu Pro Met Ala Phe
1               5                   10

<210> SEQ ID NO 253
<211> LENGTH: 11
<212> TYPE: PRT
<213> ORGANISM: Phytophthora sojae

<400> SEQUENCE: 253

Arg Ser Phe Tyr Pro Glu Leu Arg Leu Leu Phe
1               5                   10

<210> SEQ ID NO 254
<211> LENGTH: 11
<212> TYPE: PRT
<213> ORGANISM: Sporosarcina newyorkensis

<400> SEQUENCE: 254

Leu Thr Ile Ser Pro Glu Ile Pro Pro Tyr Phe
1               5                   10

<210> SEQ ID NO 255
<211> LENGTH: 11
<212> TYPE: PRT
<213> ORGANISM: Acinetobacter sp. P8-3-8

<400> SEQUENCE: 255

Glu Ser Phe Arg Pro Glu Ile Arg Gln Tyr Phe
1               5                   10

<210> SEQ ID NO 256
<211> LENGTH: 11
<212> TYPE: PRT
<213> ORGANISM: Candida orthopsilosis Co 90-125

<400> SEQUENCE: 256

Gly Ser Leu Ser Pro Glu Leu Arg Pro Ile Phe
1               5                   10

<210> SEQ ID NO 257
<211> LENGTH: 11
<212> TYPE: PRT
<213> ORGANISM: Halobacterium sp. NRC-1

<400> SEQUENCE: 257

Ser Thr Leu Ser Pro Glu Leu Arg Gly Arg Trp
1               5                   10

<210> SEQ ID NO 258
<211> LENGTH: 11
<212> TYPE: PRT
<213> ORGANISM: Sulfuricurvum kujiense DSM 16994

<400> SEQUENCE: 258

Lys Ser Phe Arg Pro Glu Leu Lys Glu Phe Tyr
1               5                   10

<210> SEQ ID NO 259
<211> LENGTH: 11
<212> TYPE: PRT
<213> ORGANISM: Artificial sequence
<220> FEATURE:
<223> OTHER INFORMATION: synthetic amino acid sequence

<400> SEQUENCE: 259

```
Lys Ser Leu Thr Pro Glu Val Arg Gly Tyr Trp
1               5                   10

<210> SEQ ID NO 260
<211> LENGTH: 11
<212> TYPE: PRT
<213> ORGANISM: Artificial sequence
<220> FEATURE:
<223> OTHER INFORMATION: synthetic amino acid sequence

<400> SEQUENCE: 260

Trp Thr Ser His Pro Glu Ile Arg Ala Tyr Phe
1               5                   10

<210> SEQ ID NO 261
<211> LENGTH: 11
<212> TYPE: PRT
<213> ORGANISM: Artificial sequence
<220> FEATURE:
<223> OTHER INFORMATION: synthetic amino acid sequence

<400> SEQUENCE: 261

Ala Ser Phe Arg Pro Glu Leu Ala Leu Arg Tyr
1               5                   10

<210> SEQ ID NO 262
<211> LENGTH: 11
<212> TYPE: PRT
<213> ORGANISM: Artificial sequence
<220> FEATURE:
<223> OTHER INFORMATION: synthetic amino acid sequence

<400> SEQUENCE: 262

Trp Thr Ser His Pro Glu Ile Arg Ala Tyr Phe
1               5                   10

<210> SEQ ID NO 263
<211> LENGTH: 11
<212> TYPE: PRT
<213> ORGANISM: Artificial sequence
<220> FEATURE:
<223> OTHER INFORMATION: synthetic amino acid sequence

<400> SEQUENCE: 263

Lys Ser Leu Thr Pro Glu Val Arg Glu Tyr Phe
1               5                   10

<210> SEQ ID NO 264
<211> LENGTH: 11
<212> TYPE: PRT
<213> ORGANISM: Artificial sequence
<220> FEATURE:
<223> OTHER INFORMATION: synthetic amino acid sequence

<400> SEQUENCE: 264

Lys Ser Leu Ala Pro Glu Val Arg Glu Leu Phe
1               5                   10

<210> SEQ ID NO 265
<211> LENGTH: 11
<212> TYPE: PRT
<213> ORGANISM: Artificial sequence
<220> FEATURE:
<223> OTHER INFORMATION: synthetic amino acid sequence

<400> SEQUENCE: 265
```

```
Arg Ser Phe Tyr Pro Glu Ile Arg Glu Tyr Phe
1               5                   10
```

<210> SEQ ID NO 266
<211> LENGTH: 11
<212> TYPE: PRT
<213> ORGANISM: Artificial sequence
<220> FEATURE:
<223> OTHER INFORMATION: synthetic amino acid sequence

<400> SEQUENCE: 266

```
Leu Ser Leu Arg Pro Glu Ile Arg Glu Tyr Trp
1               5                   10
```

<210> SEQ ID NO 267
<211> LENGTH: 11
<212> TYPE: PRT
<213> ORGANISM: Artificial sequence
<220> FEATURE:
<223> OTHER INFORMATION: synthetic amino acid sequence

<400> SEQUENCE: 267

```
Gly Thr Ile Arg Pro Glu Ile Arg Glu Met Trp
1               5                   10
```

<210> SEQ ID NO 268
<211> LENGTH: 11
<212> TYPE: PRT
<213> ORGANISM: Artificial sequence
<220> FEATURE:
<223> OTHER INFORMATION: synthetic amino acid sequence

<400> SEQUENCE: 268

```
Asn Ser Phe Lys Pro Glu Ile Pro Asp Tyr Phe
1               5                   10
```

<210> SEQ ID NO 269
<211> LENGTH: 11
<212> TYPE: PRT
<213> ORGANISM: Artificial sequence
<220> FEATURE:
<223> OTHER INFORMATION: synthetic amino acid sequence

<400> SEQUENCE: 269

```
Gly Thr Ile Ser Pro Glu Ile Arg Glu Met Trp
1               5                   10
```

<210> SEQ ID NO 270
<211> LENGTH: 11
<212> TYPE: PRT
<213> ORGANISM: Artificial sequence
<220> FEATURE:
<223> OTHER INFORMATION: synthetic amino acid sequence

<400> SEQUENCE: 270

```
Leu Ser Leu Arg Pro Glu Val Pro Leu Phe Phe
1               5                   10
```

<210> SEQ ID NO 271
<211> LENGTH: 11
<212> TYPE: PRT
<213> ORGANISM: Artificial sequence
<220> FEATURE:
<223> OTHER INFORMATION: synthetic amino acid sequence

<400> SEQUENCE: 271

Ser Ser Gly Val Pro Glu Val Arg Met Met Phe

```
<210> SEQ ID NO 272
<211> LENGTH: 11
<212> TYPE: PRT
<213> ORGANISM: Artificial sequence
<220> FEATURE:
<223> OTHER INFORMATION: synthetic amino acid sequence

<400> SEQUENCE: 272

Ser Ser Val Val Pro Glu Val Arg Met Met Phe
1               5                   10

<210> SEQ ID NO 273
<211> LENGTH: 11
<212> TYPE: PRT
<213> ORGANISM: Artificial sequence
<220> FEATURE:
<223> OTHER INFORMATION: synthetic amino acid sequence

<400> SEQUENCE: 273

Arg Ser Phe Tyr Pro Glu Ile Arg Glu Tyr Phe
1               5                   10

<210> SEQ ID NO 274
<211> LENGTH: 11
<212> TYPE: PRT
<213> ORGANISM: Artificial sequence
<220> FEATURE:
<223> OTHER INFORMATION: synthetic amino acid sequence

<400> SEQUENCE: 274

Gly Thr Ile Arg Pro Glu Ile Pro Asp Tyr Phe
1               5                   10

<210> SEQ ID NO 275
<211> LENGTH: 11
<212> TYPE: PRT
<213> ORGANISM: Artificial sequence
<220> FEATURE:
<223> OTHER INFORMATION: synthetic amino acid sequence

<400> SEQUENCE: 275

Arg Ser Phe Tyr Pro Glu Ile Arg Glu Tyr Phe
1               5                   10

<210> SEQ ID NO 276
<211> LENGTH: 11
<212> TYPE: PRT
<213> ORGANISM: Artificial sequence
<220> FEATURE:
<223> OTHER INFORMATION: synthetic amino acid sequence

<400> SEQUENCE: 276

Leu Ser Gly Ser Pro Glu Leu Arg Met Ile Phe
1               5                   10

<210> SEQ ID NO 277
<211> LENGTH: 11
<212> TYPE: PRT
<213> ORGANISM: Artificial sequence
<220> FEATURE:
<223> OTHER INFORMATION: synthetic amino acid sequence

<400> SEQUENCE: 277

Ser Ser Phe Ser Pro Glu Leu Arg Met Arg Trp
1               5                   10
```

```
<210> SEQ ID NO 278
<211> LENGTH: 11
<212> TYPE: PRT
<213> ORGANISM: Artificial sequence
<220> FEATURE:
<223> OTHER INFORMATION: synthetic amino acid sequence

<400> SEQUENCE: 278

Ala Ser Phe Arg Pro Glu Leu Ala Glu Phe Trp
1               5                   10
```

LIGAND DISCOVERY FOR T CELL RECEPTORS

CROSS REFERENCE

This application claims benefit and is a Continuation of application Ser. No. 17/011,911, filed Sep. 3, 2020, now U.S. Pat. No. 11,125,756, issued Sep. 21, 2021, which claims benefit of application Ser. No. 15/301,930, filed Oct. 4, 2016, now U.S. Pat. No. 10,816,554, issued Oct. 27, 2020, which claims benefit of PCT Application No. PCT/US2015/024244, filed Apr. 3, 2015, which claims benefit of U.S. Provisional Patent Application No. 61/975,646, filed Apr. 4, 2014, which applications are incorporated herein by reference in their entirety.

FEDERALLY SPONSORED RESEARCH AND DEVELOPMENT

This invention was made with Government support under contract CA132681, AI048540, AI057234, and AI103867 awarded by the National Institutes of Health. The Government has certain rights in the invention.

SEQUENCE LISTING

This application contains a sequence listing which has been submitted in ASCII format via EFS-Web and is hereby incorporated by reference in its entirety. Said ASCII copy, created on Jul. 8, 2015, is named S13-123_STAN-1037CON3_SeqList_ST25.txt and is 92,000 bytes in size.

BACKGROUND OF THE INVENTION

T cells are the central mediators of adaptive immunity, through both direct effector functions and coordination and activation of other immune cells. Each T cell expresses a unique T cell receptor (TCR), selected for the ability to bind to major histocompatibility complex (MHC) molecules presenting peptides. TCR recognition of peptide-MHC (pMHC) drives T cell development, survival, and effector functions. Even though TCR ligands are relatively low affinity (1-100 μM), the TCRs are remarkably sensitive, requiring as few as 10 agonist peptides to fully activate a T cell.

Extensive structural studies of TCR recognition of pMHC show the vast majority of studied TCR-pMHC complexes share a consistent binding orientation, driven by conserved contacts between the tops of the MHC helices and the germline-encoded TCR CDR1 and CDR2 loops (see Garcia and Adams (2005) Cell 122, 333-336; Garcia et al. (2009) Nat Immunol 10, 143-147; and Rudolph et al. (2006) Annual Review of Immunology 24, 419-466). These conserved contacts have likely coevolved throughout the development of the adaptive immune system and serve as the basis of MHC restriction of the as TCR repertoire (Scott-Browne et al., 2011). Alteration to the typical TCR-pMHC interaction has been shown to correlate with abrogated signaling and, when present in development, skewed TCR repertoires (Adams et al. (2011) Immunity 35(5):681-93; Birnbaum et al. (2012) Immunol. Rev. 250(1):82-101).

An additional important feature of the TCR is the ability to balance cross-reactivity with specificity. Since the number of T cells that would be necessary to uniquely recognize every possible pMHC combination is extremely high, and since there are few if any 'holes' characterized in the TCR repertoire, it has been posited that a large degree of TCR cross-reactivity is a requirement of functional antigen recognition. How the T cell repertoire can simultaneously be MHC restricted, cross-reactive enough to ensure all potential antigenic challenges can be met, yet still specific enough to avoid aberrant autoimmunity, has remained an open and pressing question in immunology.

The present invention provides materials and methods for the identification of T cell receptor ligands.

RELATED PUBLICATIONS

U.S. Pat. No. 8,450,247, Peelle et al.; Patent Application Publication; Pub. No. US 2010/0210473, Bowley et al.; US 2004/0146976, Dane et al.; International Application WO2004015395; International Application WO2005116646; International Application WO2012022975.

SUMMARY OF THE INVENTION

Compositions and methods are provided for the identification of peptide sequences that are ligands for a T cell receptor (TCR) of interest, in a given MHC context. In the methods of the invention, a library of single chain polypeptides are generated that comprise: the binding domains of a major histocompatibility complex protein; and diverse peptide ligands. The library is initially generated as a population of polynucleotides encoding the single chain polypeptide operably linked to an expression vector, which library may comprise at least $10^6$, at least $10^7$, more usually at least $10^8$ different peptide ligand coding sequences, and may contain up to about $10^{13}$, $10^{14}$ or more different ligand sequences. The library is introduced into a suitable host cell that expresses the encoded polypeptide, which host cells include, without limitation, yeast cells. The number of unique host cells expressing the polypeptide is generally less than the total predicted diversity of polynucleotides, e.g. up to about $5\times10^9$ different specificities, up to about $10^9$, up to about $5\times10^8$, up to about $10^8$, etc.

A TCR of interest is multimerized to enhance binding, and used to select for host cells expressing those single chain polypeptides that bind to the T cell receptor. Iterative rounds of selection are performed, i.e. the cells that are selected in the first round provide the starting population for the second round, etc. until the selected population has a signal above background, usually at least three and more usually at least four rounds of selection are performed. Polynucleotides encoding the final selected population from the library of single chain polypeptides are subjected to high throughput sequencing. It is shown herein that the selected set of peptide ligands exhibit a restricted choice of amino acids at residues, e.g. the residues that contact the TCR, which information can be input into an algorithm that can be used to analyze public databases for all peptides that meet the criteria for binding, and which provides a set of peptides that meet these criteria.

The peptide ligand is from about 8 to about 20 amino acids in length, usually from about 8 to about 18 amino acids, from about 8 to about 16 amino acids, from about 8 to about 14 amino acids, from about 8 to about 12 amino acids, from about 10 to about 14 amino acids, from about 10 to about 12 amino acids. It will be appreciated that a fully random library would represent an extraordinary number of possible combinations. In preferred methods, the diversity is limited at the residues that anchor the peptide to the MHC binding domains, which are referred to herein as MHC anchor residues. The position of the anchor residues in the peptide are determined by the specific MHC binding domains. Class I binding domains have anchor residues at the P2 position, and at the last contact residue. Class II binding domains have an anchor residue at P1, and depending on the allele, at one of P4, P6 or P9. For example, the anchor residues for IE$^k$ are P1 {I,L,V} and P9 {K}; the anchor residues for HLA-DR15 are P1 {I,L,V} and P4 {F, Y}. Anchor residues for DR alleles are shared at P1, with allele-specific anchor residues at P4, P6, P7, and/or P9.

In some embodiments, the binding domains of a major histocompatibility complex protein are soluble domains of Class II alpha and beta chain. In some such embodiments the binding domains have been subjected to mutagenesis and selected for amino acid changes that enhance the solubility of the single chain polypeptide, without altering the peptide binding contacts. In certain specific embodiments, the binding domains are HLA-DR4α comprising the set of amino acid changes {M36L, V132M}; and HLA-DR4β comprising the set of amino acid changes {H62N, D72E}. In certain specific embodiments, the binding domains are HLA-DR15α comprising the set of amino acid changes {F12S, M23K}; and HLA-DR15β comprising the amino acid change {P11S}. In certain specific embodiments, the binding domains are H2 IE$^k$α comprising the set of amino acid changes {I8T, F12S, L14T, A56V} and H2 IE$^k$β comprising the set of amino acid changes {W6S, L8T, L34S}.

In some embodiments, the binding domains of a major histocompatibility complex protein comprise the alpha 1 and alpha 2 domains of a Class I MHC protein, which are provided in a single chain with β2 microglobulin. In some such embodiments the Class I protein has been subjected to mutagenesis and selected for amino acid changes that enhance the solubility of the single chain polypeptide, without altering the peptide binding contacts. In certain specific embodiments, the binding domains are HLA-A2 alpha 1 and alpha 2 domains, comprising the amino acid change {Y84A}. In certain specific embodiments, the binding domains are H2-L$^d$ alpha 1 and alpha 2 domains, comprising the amino acid change {M31R}. In certain specific embodiments the binding domains are HLA-B57 alpha 1, alpha 2 and alpha 3 domains, comprising the amino acid change {Y84A}.

In some embodiments of the invention, a library is provided of polypeptides, or of nucleic acids encoding such polypeptides, wherein the polypeptide structure has the formula:

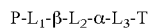

P-L$_1$-β-L$_2$-α-L$_3$-T wherein each of L$_1$, L$_2$ and L$_3$ are flexible linkers of from about 4 to about 12 amino acids in length, e.g. comprising glycine, serine, alanine, etc.

α is a soluble form of a domains of a class I MHC protein, or class II αMHC protein;

β is a soluble form of (i) a β chain of a class II MHC protein or (ii) β$_2$ microglobulin for a class I MHC protein;

T is a domain that allows the polypeptide to be tethered to a cell surface, including without limitation yeast Aga2, or is a transmembrane domain that allows display on a cell surface; and P is a peptide ligand, usually a library of different peptide ligands as described above, where at least 10$^6$, at least 10$^7$, more usually at least 10$^8$ different peptide ligands are present in the library. The MHC binding domains are as described above. The library can be provided as a nucleic acid composition, e.g. operably linked to an expression vector. The library can be provided as a population of host cells transfected with the nucleic acid composition. In some embodiments the host cells are yeast (*S. cerevisae*) cells. The MHC portion of the construct may be a "mini" MHC where the boundaries for inclusion of the protein are set to be the end of the MHC peptide binding domain; or may be set at the end of the Beta2/Alpha2/Alpha3 domains as judged by structure and/or sequence for the 'full length' MHCs.

The multimerized T cell receptor for selection is a soluble protein comprising the binding domains of a TCR of interest, e.g. TCRα/β, TCRγ/δ, and can be synthesized by any convenient method. The TCR can be provided as a single chain, or a heterodimer. In some embodiments, the soluble TCR is modified by the addition of a biotin acceptor peptide sequence at the C terminus of one polypeptide. After biotinylation at the acceptor peptide, the TCR can be multimerized by binding to biotin binding partner, e.g. avidin, streptavidin, traptavidin, neutravidin, etc. The biotin binding partner can comprise a detectable label, e.g. a fluorophore, mass label, etc., or can be bound to a particle, e.g. a paramagnetic particle. Selection of ligands bound to the TCR can be performed by flow cytometry, magnetic selection, and the like as known in the art.

Also provided herein is a method of determining the set of polypeptide ligands that bind to a T cell receptor of interest, comprising the steps of: performing multiple rounds of selection of a polypeptide library as set forth herein with a T cell receptor of interest; performing deep sequencing of the peptide ligands that are selected; inputting the sequence data to computer readable medium, where it is used to generate a search algorithm embodied as a program of instructions executable by computer and performed by means of software components loaded into the computer.

Also provided herein are software products tangibly embodied in a machine-readable medium, the software product comprising instructions operable to cause one or more data processing apparatus to perform operations comprising: generating a n×20 matrix from the positional frequencies of selected peptide ligands obtained by the screening methods of the invention, where n is the number of amino acid positions in the peptide ligand library. A cutoff of amino acid frequencies is set, e.g. less than 0.1, less than 0.05, less than 0.01, and frequencies below the cutoff are set to zero. A database of sequences, e.g. a set of human polypeptide sequences; a set of pathogen polypeptide sequences, a set of microbial polypeptide sequences, a set of allergen polypeptide sequences; etc. are searched with the algorithm using an n-position sliding window alignment with scoring the product of positional amino acid frequencies from the substitution matrix. An aligned segment containing at least one amino acid where the frequency is below the cutoff is excluded as a match.

In some embodiments, a kit is provided for the identification of peptide sequences that are ligands for a T cell receptor (TCR) of interest. Such a kit may comprise a library of polynucleotides encoding a polypeptide of the formula P-L$_1$-β-L$_2$-α-L$_3$-T, where a diverse set of peptide ligands is provided, e.g. at least 10$^6$, at least 10$^7$, more usually at least 10$^8$, at least 10$^9$, at least 10$^{10}$ different peptide ligands are present in the library and may contain up to about 10$^{14}$ different ligands, usually up to about 10$^{13}$ different ligands. The polynucleotide library can be provided as a population of transfected cells, or as an isolated population of nucleic acids. Reagents for labeling and multimerizing a TCR can be included. In some embodiments the kit will further comprise a software package for analysis of a sequence database.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 6: Design and selection of HLA-DR15 based libraries for myelin basic protein (MBP)-reactive human TCRs. (A) HLA-DR15 library design based upon structure of MBP-HLA-DR15/Ob.1A12 complex crystal structure (PDB ID:1YMM). All residues (P(−4)-P10) are fully randomized, except for the P1 and P4 anchors (in black). TCR contacts are colored magenta. (B) Heatmap of amino acid preference by position for Ob.1A12 TCR. The sequence for MBP is represented via outlined boxes. TCR contacts are labeled red on the x axis. (C) Design and selection results of library that suppresses central 'HF' TCR recognition motif at P2-P3 of peptide. Resulting register shift is shown in blue on x axis. (D) Sequence clustering shows distinct, related clusters of selected peptides. Sequence cluster placed in a representation of whole-library sequence space (left: 1× magnification, center: 1000× magnification) for reference.

FIG. 9: Statistics and reads for 2B4 selections of I-Ek library. (A) Summary of total number of Illumina reads by round for 2B4 selections. Corrected sequences correspond to reads which were in frame with no stop codons. Corrected unique peptides were the number of peptides present with greater than 4 unique sequence reads, after corrections for frame, stop codons, and 1 nt read errors (which were coalesced into the parent peptides). (B) Relative enrichment for 25 most abundant peptide after 4 rounds of selection with 2B4 TCR.

FIG. 11: Characterization of library selected peptides via signaling and affinity. (A) Dose response curves of IL-2 release assay for 2B4 and 5cc7 T cell blasts. (B) and (C) Dose response curves of CD69 upregulation assay for 2B4 and 5cc7 T cell blasts. Curves in black represent peptides for which there were no sequencing reads for the given TCR. (D) Good correlation between EC50 of CD69 upregulation and IL-2 release for library selected peptide. (E) Sequence of peptides tested for binding via SPR. (F) SPR titrations for selected peptides using refolded 2B4 (left), 5cc7 (center), and 226 (right) TCRs.

FIG. 12: Features of TCR recognition of MCC and library-derived peptides bound to I-Ek. (A) A shared contact exists between Arg29α of CDR1α and the peptide in all four complexes. (B) Side chain flip of 2B4 Glu101β repurposes former peptide-binding contact to intra-loop contact between MCC and 2A complexes. (C) Alignment of 5c1-I-Ek/5cc7 and 5c2-I-Ek/5cc7 complexes shows essentially identical binding footprint. (D) Conversion of a hydrogen bond between Gln50β of 226 and P8 Thr in MCC (black) to a π-cation interaction between Gln50β of 5cc7 and P8 Phe in 501 (red). (E) Significant deviation of TCR Cβ FG loop between MCC-I-Ek/226 and 5c1-I-Ek/5cc7 complexes correlates with reduced signaling potency.

DETAILED DESCRIPTION OF THE EMBODIMENTS

Figure 1:
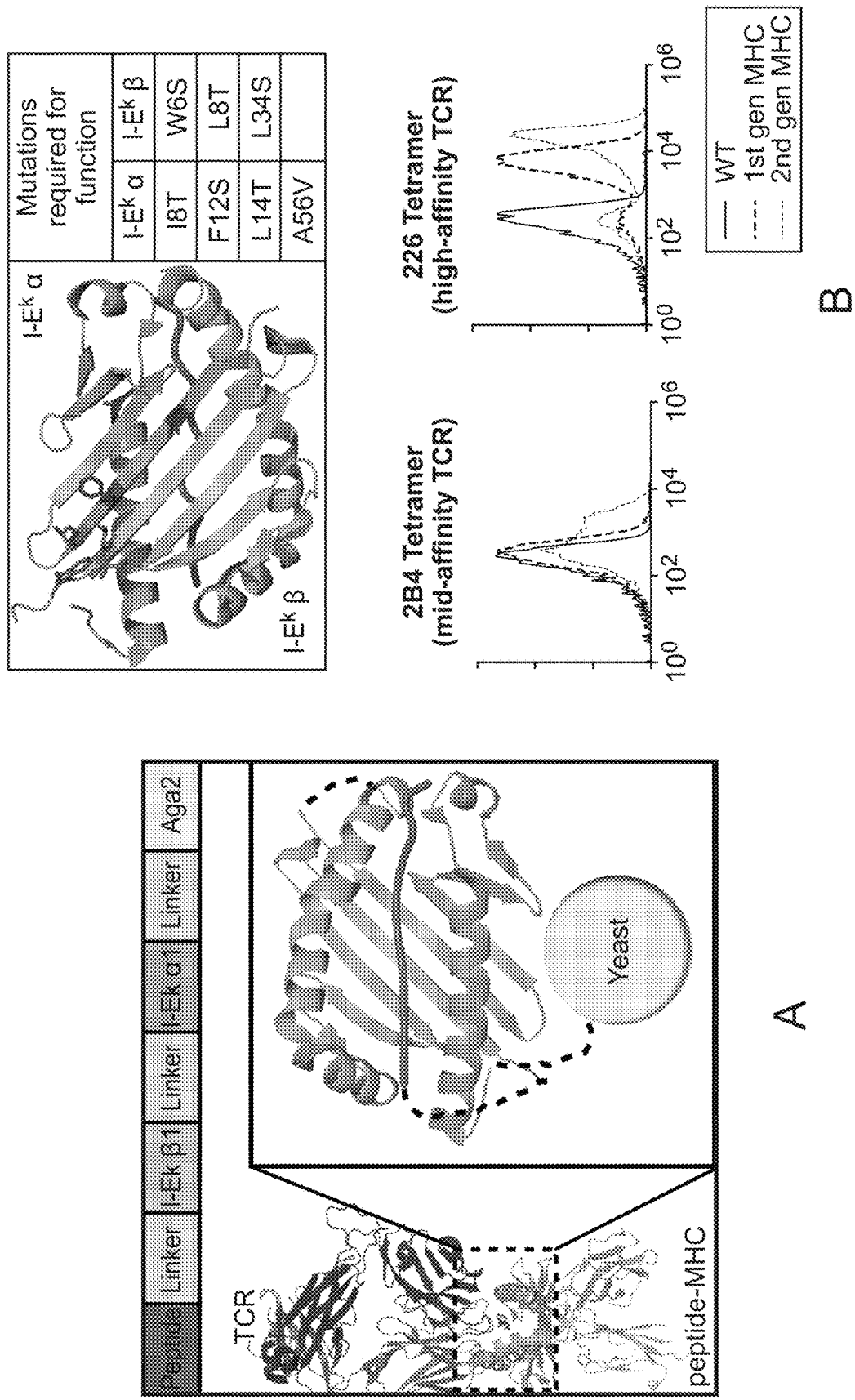
FIG. 1: Library design and selection of I-E$^k$, a murine class II MHC molecule. (A) Schematic of the murine class II MHC I-E$^k$ displayed on yeast, as β1α1 'mini' MHC with peptide covalently linked to MHC N-terminus. (B) Mutations required for correct folding of the β1α1 'mini' I-E$^k$ (top). Mutations found via error prone mutagenesis and selection are colored purple. Rationally introduced mutations are colored red. Staining with 2B4 and 226 tetramers demonstrate function of error prone-only construct (1$^{st}$ gen MHC) as well as error prone+designed mutant construct (2nd gen MHC) (bottom). (C) Design of the peptide library displayed by I-E$^k$. Design is based upon the structure of 2B4 bound to MCC/I-E$^k$ (left). Residues from P(−2) to P10 are randomized, with limited diversity at P(−2), P10, and the P1/P9 anchors (right). Residues are colored corresponding to TCR contacts (magenta), MHC contacts (brown), MHC anchors (black), or neutral contacts (grey). (D) TCR tetramer staining of three clones selected for binding to 2B4 TCR compared to MCC (wild-type). TCR contacts are colored red. See also FIG. 8.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. In this specification and the appended claims, the singular forms "a," "an" and "the" include plural reference unless the context clearly dictates otherwise.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, illustrative methods, devices and materials are now described.

All publications mentioned herein are incorporated herein by reference for the purpose of describing and disclosing the subject components of the invention that are described in the publications, which components might be used in connection with the presently described invention.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

MHC Proteins. Major histocompatibility complex proteins (also called human leukocyte antigens, HLA, or the H2 locus in the mouse) are protein molecules expressed on the surface of cells that confer a unique antigenic identity to these cells. MHC/HLA antigens are target molecules that are recognized by T-cells and natural killer (NK) cells as being derived from the same source of hematopoietic reconstituting stem cells as the immune effector cells ("self") or as being derived from another source of hematopoietic reconstituting cells ("non-self"). Two main classes of HLA antigens are recognized: HLA class I and HLA class II.

The MHC proteins used in the libraries and methods of the invention may be from any mammalian or avian species, e.g. primate sp., particularly humans; rodents, including mice, rats and hamsters; rabbits; equines, bovines, canines, felines; etc. Of particular interest are the human HLA proteins, and the murine H-2 proteins. Included in the HLA proteins are the class II subunits HLA-DPα, HLA-DPβ, HLA-DQα, HLA-DQβ, HLA-DRα and HLA-DRβ, and the class I proteins HLA-A, HLA-B, HLA-C, and β$_2$-microglobulin. Included in the murine H-2 subunits are the class I H-2K, H-2D, H-2L, and the class II I-Aα, I-Aβ, I-Eα and I-Eβ, and β₂-microglobulin.

The MHC binding domains are typically a soluble form of the normally membrane-bound protein. The soluble form is derived from the native form by deletion of the transmembrane domain. Conveniently, the protein is truncated, removing both the cytoplasmic and transmembrane domains. In some embodiments, the binding domains of a major histocompatibility complex protein are soluble domains of Class II alpha and beta chain. In some such embodiments the binding domains have been subjected to mutagenesis and selected for amino acid changes that enhance the solubility of the single chain polypeptide, without altering the peptide binding contacts.

An "allele" is one of the different nucleic acid sequences of a gene at a particular locus on a chromosome. One or more genetic differences can constitute an allele. An important aspect of the HLA gene system is its polymorphism. Each gene, MHC class I (A, B and C) and MHC class II (DP, DQ and DR) exists in different alleles. Current nomenclature for HLA alleles are designated by numbers, as described by Marsh et al.: Nomenclature for factors of the HLA system, 2010. *Tissue Antigens* 75:291-455, herein specifically incorporated by reference. For HLA protein and nucleic acid sequences, see Robinson et al. (2011), The IMGT/HLA database. Nucleic Acids Research 39 Suppl 1:D1171-6, herein specifically incorporated by reference.

The numbering of amino acid residues on the various MHC proteins and variants disclosed herein is made to be consistent with the full length polypeptide. Boundaries were set to either be the end of the MHC peptide binding domain (as judged by examining crystal structures) for the 'mini' MHCs, e.g. as exemplified herein with I-Ek, H2-Ld, and HLA-DR15, and the end of the Beta2/Alpha2/Alpha3 domains as judged by structure and/or sequence for the 'full length' MHCs, as exemplified herein with HLA-A2, -B57, and -DR4.

In some embodiments, the MHC portion of a construct is the MHC portion delineated in any of SEQ ID NO:1-6. It will be understood by one of skill in the art that the peptide and linker portions can be varied from the provided sequences.

MHC context. The function of MHC molecules is to bind peptide fragments derived from pathogens and display them on the cell surface for recognition by the appropriate T cells. Thus T cell receptor recognition can be influenced by the MHC protein that is presenting the antigen. The term MHC context refers to the recognition by a TCR of a given peptide, when it is presented by a specific MHC protein.

Class II HLA/MHC. Class II binding domains generally comprise the α1 and α2 domains for the a chain, and the β31 and β2 domains for the β chain. Not more than about 10, usually not more than about 5, preferably none of the amino acids of the transmembrane domain will be included. The deletion will be such that it does not interfere with the ability of the α2 or β2 domain to bind peptide ligands.

In some embodiments, the binding domains of a major histocompatibility complex protein are soluble domains of Class II alpha and beta chain. In some such embodiments the binding domains have been subjected to mutagenesis and selected for amino acid changes that enhance the solubility of the single chain polypeptide, without altering the peptide binding contacts.

In certain specific embodiments, the binding domains are an HLA-DR allele. The HLA-DRA protein can be selected, without limitation, from the binding domains of DRA*01:01:01:01; DRA*01:01:01:02; DRA*01:01:01:03; DRA*01:01:02; DRA*01:02:01; DRA*01:02:02; and DRA*01:02:03, which may be modified to comprise the amino acid changes {M36L, V132M}; or {F12S, M23K}, depending on whether it is provided in the context of a full-length or mini-allele. The HLA-DRA binding domains can be combined with any one of the HLA-DRB binding domains.

In certain such embodiments, the HLA-DRA allele is paired with the binding domains of an HLA-DRB4 allele. The HLA-DRB4 allele can be selected from the publicly available DRB4 alleles, including without limitation: DRB1*04:01:01; DRB1*04:01:02; DRB1*04:01:03; DRB1*04:01:04; DRB1*04:01:05; DRB1*04:01:06; DRB1*04:01:07; DRB1*04:01:08; DRB1*04:01:09; DRB1*04:01:10; DRB1*04:01:11; DRB1*04:01:12; DRB1*04:01:13; DRB1*04:01:14; DRB1*04:02:01; DRB1*04:02:02; DRB1*04:02:03; DRB1*04:03:01; DRB1*04:03:02; DRB1*04:03:03; DRB1*04:03:04; DRB1*04:03:05; DRB1*04:03:06; DRB1*04:03:07; DRB1*04:03:08; DRB1*04:04:01; DRB1*04:04:02; DRB1*04:04:03; DRB1*04:04:04; DRB1*04:04:05; DRB1*04:04:06; DRB1*04:04:07; DRB1*04:04:08; DRB1*04:05:01; DRB1*04:05:02; DRB1*04:05:03; DRB1*04:05:04; DRB1*04:05:05; DRB1*04:05:06; DRB1*04:05:07; DRB1*04:05:08; DRB1*04:05:09; DRB1*04:05:10; DRB1*04:05:11; DRB1*04:05:13; DRB1*04:05:14; DRB1*04:05:15; DRB1*04:05:16; DRB1*04:06:01; DRB1*04:06:02; DRB1*04:06:03; DRB1*04:06:04; DRB1*04:06:05; DRB1*04:07:01; DRB1*04:07:02; DRB1*04:07:03; DRB1*04:07:04; DRB1*04:08:01; DRB1*04:08:02; DRB1*04:08:03; DRB1*04:09; DRB1*04:10:01; DRB1*04:10:02; DRB1*04:11:01; DRB1*04:11:02; DRB1*04:11:03; DRB1*04:12; DRB1*04:13; DRB1*04:14; DRB1*04:15; DRB1*04:16; DRB1*04:17:01; DRB1*04:17:02; DRB1*04:18; DRB1*04:19; DRB1*04:20; DRB1*04:21; DRB1*04:22; DRB1*04:23; DRB1*04:24; DRB1*04:25; DRB1*04:26; DRB1*04:27; DRB1*04:28; DRB1*04:29; DRB1*04:30; DRB1*04:31; DRB1*04:32; DRB1*04:33; DRB1*04:34; DRB1*04:35; DRB1*04:36; DRB1*04:37; DRB1*04:38; DRB1*04:39; DRB1*04:40; DRB1*04:41; DRB1*04:42; DRB1*04:43; DRB1*04:44; DRB1*04:45; DRB1*04:46; DRB1*04:47; DRB1*04:48; DRB1*04:49; DRB1*04:50; DRB1*04:51; DRB1*04:52; DRB1*04:53; DRB1*04:54; DRB1*04:55; DRB1*04:56; DRB1*04:57; DRB1*04:58; DRB1*04:59; DRB1*04:60; DRB1*04:61; DRB1*04:62; DRB1*04:63; DRB1*04:64; DRB1*04:65; DRB1*04:66; DRB1*04:67; DRB1*04:68; DRB1*04:69; DRB1*04:70; DRB1*04:71; DRB1*04:72:01; DRB1*04:72:02; DRB1*04:73; DRB1*04:74; DRB1*04:75; DRB1*04:76; DRB1*04:77; DRB1*04:78; DRB1*04:79; DRB1*04:80; DRB1*04:81N; DRB1*04:82; DRB1*04:83; DRB1*04:84; DRB1*04:85; DRB1*04:86; DRB1*04:87; DRB1*04:88; DRB1*04:89; DRB1*04:90; DRB1*04:91; DRB1*04:92; DRB1*04:93; DRB1*04:94N; DRB1*04:95:01; DRB1*04:95:02; DRB1*04:96; DRB1*04:97; DRB1*04:98:01; DRB1*04:98:02; DRB1*04:99; DRB1*04:100; DRB1*04:101; DRB1*04:102; DRB1*04:103; DRB1*04:104; DRB1*04:105:01; DRB1*04:105:02; DRB1*04:106; DRB1*04:107; DRB1*04:108; DRB1*04:109; DRB1*04:110; DRB1*04:111; DRB1*04:112; DRB1*04:113; DRB1*04:114; DRB1*04:115; DRB1*04:116; DRB1*04:117; DRB1*04:118; DRB1*04:119N; DRB1*04:120N; DRB1*04:121; DRB1*04:122; DRB1*04:123; DRB1*04:124; DRB1*04:125; DRB1*04:126; DRB1*04:127; DRB1*04:128; DRB1*04:129; DRB1*04:130; DRB1*04:131; DRB1*04:132; DRB1*04:133;

DRB1*04:134; DRB1*04:135; DRB1*04:136; DRB1*04:137; DRB1*04:138; DRB1*04:139; DRB1*04:140; DRB1*04:141; DRB1*04:142N; DRB1*04:143; DRB1*04:144; DRB1*04:145; DRB1*04:146; DRB1*04:147; DRB1*04:148; DRB1*04:149; DRB1*04:150; DRB1*04:151; DRB1*04:152; DRB1*04:153; DRB1*04:154; DRB1*04:155; DRB1*04:156; DRB1*04:157N; DRB1*04:158N; DRB1*04:159; DRB1*04:160; DRB1*04:161; DRB1*04:162; DRB1*04:163; DRB1*04:164; DRB1*04:165; DRB1*04:166; DRB1*04:167; DRB1*04:168; DRB1*04:169; DRB1*04:170; DRB1*04:171; and DRB1*04:172; which may be modified to comprise the amino acid changes {H62N, D72E}.

In other such embodiments the HLA-DRA allele is paired with the binding domains of an HLA-DRB15 allele. The HLA-DRB15 allele can be selected from the publicly available DRB15 alleles, including without limitation: DRB1*15:01:01:01; DRB1*15:01:01:02; DRB1*15:01:01:03; DRB1*15:01:01:04; DRB1*15:01:02; DRB1*15:01:03; DRB1*15:01:04; DRB1*15:01:05; DRB1*15:01:06; DRB1*15:01:07; DRB1*15:01:08; DRB1*15:01:09; DRB1*15:01:10; DRB1*15:01:11; DRB1*15:01:12; DRB1*15:01:13; DRB1*15:01:14; DRB1*15:01:15; DRB1*15:01:16; DRB1*15:01:17; DRB1*15:01:18; DRB1*15:01:19; DRB1*15:01:20; DRB1*15:01:21; DRB1*15:01:22; DRB1*15:02:01; DRB1*15:02:02; DRB1*15:02:03; DRB1*15:02:04; DRB1*15:02:05; DRB1*15:02:06; DRB1*15:02:07; DRB1*15:02:08; DRB1*15:02:09; DRB1*15:02:10; DRB1*15:03:01:01; DRB1*15:03:01:02; DRB1*15:03:02; DRB1*15:04; DRB1*15:05; DRB1*15:06:01; DRB1*15:06:02; DRB1*15:07:01; DRB1*15:07:02; DRB1*15:08; DRB1*15:09; DRB1*15:10; DRB1*15:11; DRB1*15:12; DRB1*15:13; DRB1*15:14; DRB1*15:15; DRB1*15:16; DRB1*15:17N; DRB1*15:18; DRB1*15:19; DRB1*15:20; DRB1*15:21; DRB1*15:22; DRB1*15:23; DRB1*15:24; DRB1*15:25; DRB1*15:26; DRB1*15:27; DRB1*15:28; DRB1*15:29; DRB1*15:30; DRB1*15:31; DRB1*15:32; DRB1*15:33; DRB1*15:34; DRB1*15:35; DRB1*15:36; DRB1*15:37:01; DRB1*15:37:02; DRB1*15:38; DRB1*15:39; DRB1*15:40; DRB1*15:41; DRB1*15:42; DRB1*15:43; DRB1*15:44; DRB1*15:45; DRB1*15:46; DRB1*15:47; DRB1*15:48; DRB1*15:49; DRB1*15:50N; DRB1*15:51; DRB1*15:52; DRB1*15:53; DRB1*15:54; DRB1*15:55; DRB1*15:56; DRB1*15:57; DRB1*15:58; DRB1*15:59; DRB1*15:60; DRB11*15:61; DRB1*15:62; DRB1*15:63; DRB1*15:64; DRB1*15:65; DRB1*15:66; DRB1*15:67; DRB1*15:68; DRB1*15:69; DRB1*15:70; DRB1*15:71; DRB1*15:72; DRB1*15:73; DRB1*15:74; DRB1*15:75; DRB1*15:76; DRB1*15:77; DRB1*15:78; DRB1*15:79; DRB1*15:80N; DRB1*15:81; DRB1*15:82; DRB1*15:83; DRB1*15:84; DRB1*15:85; DRB1*15:86; DRB1*15:87; DRB1*15:88; DRB1*15:89; DRB1*15:90; DRB1*15:91; DRB1*15:92; DRB1*15:93; DRB1*15:94; DRB1*15:95; DRB1*15:96; DRB1*15:97; DRB1*15:98; DRB1*15:99; DRB1*15:100; DRB1*15:101; DRB1*15:102; DRB1*15:103; and DRB1*15:104; which may be modified to comprise the amino acid changes {P11S}.

In other embodiments the Class II binding domains are an H2 protein, e.g. I-Aα, I-Aβ, I-Eα and I-Eβ. In some such embodiments, the binding domains are H2 IE$^k$α which may comprise the set of amino acid changes {I8T, F12S, L14T, A56V}; and H2 IE$^k$β which may comprise the set of amino acid changes {W6S, L8T, L34S}.

Class I HLA/MHC. For class I proteins, the binding domains may include the α1, α2 and α3 domain of a Class I allele, including without limitation HLA-A, HLA-B, HLA-C, H-2K, H-2D, H-2L, which are combined with β$_2$-microglobulin. Not more than about 10, usually not more than about 5, preferably none of the amino acids of the transmembrane domain will be included. The deletion will be such that it does not interfere with the ability of the domains to bind peptide ligands.

In certain specific embodiments, the binding domains are HLA-A2 binding domains, e.g. comprising at least the alpha 1 and alpha 2 domains of an A2 protein. A large number of alleles have been identified in HLA-A2, including without limitation HLA-A*02:01:01:01 to HLA-A*02:478, which sequences are available at, for example, Robinson et al. (2011), The IMGT/HLA database. Nucleic Acids Research 39 Suppl 1:D1171-6. Among the HLA-A2 allelic variants, HLA-A*02:01 is the most prevalent. The binding domains may comprise the amino acid change {Y84A}.

In certain specific embodiments, the binding domains are HLA-B57 binding domains, e.g. comprising at least the alpha1 and alpha 2 domains of a B57 protein. The HLA-B57 allele can be selected from the publicly available B57 alleles, including without limitation: B*57:01:01; B*57:01:02; B*57:01:03; B*57:01:04; B*57:01:05; B*57:01:06; B*57:01:07; B*57:01:08; B*57:01:09; B*57:01:10; B*57:01:11; B*57:01:12; B*57:01:13; B*57:01:14; B*57:01:15; B*57:01:16; B*57:01:17; B*57:02:01; B*57:02:02; B*57:03:01; B*57:03:02; B*57:04; B*57:05; B*57:06; B*57:07; B*57:08; B*57:09; B*57:10; B*57:11; B*57:12; B*57:13; B*57:14; B*57:15; B*57:16; B*57:17; B*57:18; B*57:19; B*57:20; B*57:21; B*57:22; B*57:23; B*57:24; B*57:25; B*57:26; B*57:27; B*57:28N; B*57:29; B*57:30; B*57:31; B*57:32; B*57:33; B*57:34; B*57:35; B*57:36; B*57:37; B*57:38; B*57:39; B*57:40; B*57:41; B*57:42; B*57:43; B*57:44; B*57:45; B*57:46; B*57:47; B*57:48; B*57:49; B*57:50; B*57:51; B*57:52; B*57:53; B*57:54; B*57:55; B*57:56; B*57:57; B*57:58; B*57:59; B*57:60; B*57:61; B*57:62; B*57:63; B*57:64; B*57:65; B*57:66; B*57:67; B*57:68; and B*57:69; which may be modified to comprise the amino acid change {Y84A}.

In other embodiments, the binding domains comprise H2-L$^d$ alpha 1 and alpha 2 domains, which may comprise the amino acid change {M31R}.

T cell receptor, refers to the antigen/MHC binding heterodimeric protein product of a vertebrate, e.g. mammalian, TCR gene complex, including the human TCR α, β, γ and δ chains. For example, the complete sequence of the human β TCR locus has been sequenced, as published by Rowen et al. (1996) Science 272(5269):1755-1762; the human α TCR locus has been sequenced and resequenced, for example see Mackelprang et al. (2006) Hum Genet. 119(3):255-66; see a general analysis of the T-cell receptor variable gene segment families in Arden Immunogenetics. 1995; 42(6):455-500; each of which is herein specifically incorporated by reference for the sequence information provided and referenced in the publication.

The multimerized T cell receptor for selection in the methods of the invention is a soluble protein comprising the binding domains of a TCR of interest, e.g. TCRα/β, TCRγ/δ. The soluble protein may be a single chain, or more usually a heterodimer. In some embodiments, the soluble TCR is modified by the addition of a biotin acceptor peptide sequence at the C terminus of one polypeptide. After biotinylation at the acceptor peptide, the TCR can be multimerized by binding to biotin binding partner, e.g. avidin, streptavidin, traptavidin, neutravidin, etc. The biotin binding partner can comprise a detectable label, e.g. a fluorophore, mass label, etc., or can be bound to a particle, e.g. a paramagnetic particle. Selection of ligands bound to the TCR can be performed by flow cytometry, magnetic selection, and the like as known in the art.

Peptide ligands of the TCR are peptide antigens against which an immune response involving T lymphocyte antigen specific response can be generated. Such antigens include antigens associated with autoimmune disease, infection, foodstuffs such as gluten, etc., allergy or tissue transplant rejection. Antigens also include various microbial antigens, e.g. as found in infection, in vaccination, etc., including but not limited to antigens derived from virus, bacteria, fungi, protozoans, parasites and tumor cells. Tumor antigens include tumor specific antigens, e.g. immunoglobulin idiotypes and T cell antigen receptors; oncogenes, such as p21/ras, p53, p210/bcr-abl fusion product; etc.; developmental antigens, e.g. MART-1/Melan A; MAGE-1, MAGE-3; GAGE family; telomerase; etc.; viral antigens, e.g. human papilloma virus, Epstein Barr virus, etc.; tissue specific self-antigens, e.g. tyrosinase; gp100; prostatic acid phosphatase, prostate specific antigen, prostate specific membrane antigen; thyroglobulin, α-fetoprotein; etc.; and self-antigens, e.g. her-2/neu; carcinoembryonic antigen, muc-1, and the like.

In the methods of the invention, a library of diverse peptide antigens is generated. The peptide ligand is from about 8 to about 20 amino acids in length, usually from about 8 to about 18 amino acids, from about 8 to about 16 amino acids, from about 8 to about 14 amino acids, from about 8 to about 12 amino acids, from about 10 to about 14 amino acids, from about 10 to about 12 amino acids. It will be appreciated that a fully random library would represent an extraordinary number of possible combinations. In preferred methods, the diversity is limited at the residues that anchor the peptide to the MHC binding domains, which are referred to herein as MHC anchor residues. The position of the anchor residues in the peptide are determined by the specific MHC binding domains. Diversity may also be limited at other positions as informed by binding studies, e.g. at TCR anchors.

Library. In some embodiments of the invention, a library is provided of polypeptides, or of nucleic acids encoding such polypeptides, wherein the polypeptide structure has the formula:

polynucleotide composition encoding the P-$L_1$-β-$L_2$-α-$L_3$-T polypeptide wherein each of $L_1$, $L_2$ and $L_3$ are flexible linkers of from about 4 to about 12 amino acids in length, e.g. comprising glycine, serine, alanine, etc.

α is a soluble form of a domains of a class I MHC protein, or class II αMHC protein;

β is a soluble form of (i) a β chain of a class II MHC protein or (ii) $β_2$ microglobulin for a class I MHC protein;

T is a domain that allows the polypeptide to be tethered to a cell surface, including without limitation yeast Aga2; and P is a peptide ligand, usually a library of different peptide ligands as described above, where at least $10^6$, at least $10^7$, more usually at least $10^8$ different peptide ligands are present in the library.

Conventional methods of assembling the coding sequences can be used. In order to generate the diversity of peptide ligands, randomization, error prone PCR, mutagenic primers, and the like as known in the art are used to create a set of polynucleotides. The library of polynucleotides is typically ligated to a vector suitable for the host cell of interest. In various embodiments the library is provided as a purified polynucleotide composition encoding the P-$L_1$-β-$L_2$-α-$L_3$-T polypeptides; as a purified polynucleotide composition encoding the P-$L_1$-β-$L_2$-α-$L_3$-T polypeptides operably linked to an expression vector, where the vector can be, without limitation, suitable for expression in yeast cells; as a population of cells comprising the library of polynucleotides encoding the P-$L_1$-β-$L_2$-α-$L_3$-T polypeptides, where the population of cells can be, without limitation yeast cells, and where the yeast cells may be induced to express the polypeptide library.

"Suitable conditions" shall have a meaning dependent on the context in which this term is used. That is, when used in connection with binding of a T cell receptor to a polypeptide of the formula polynucleotide composition encoding the P-$L_1$-β-$L_2$-α-$L_3$-T polypeptide, the term shall mean conditions that permit a TCR to bind to a cognate peptide ligand. When this term is used in connection with nucleic acid hybridization, the term shall mean conditions that permit a nucleic acid of at least 15 nucleotides in length to hybridize to a nucleic acid having a sequence complementary thereto. When used in connection with contacting an agent to a cell, this term shall mean conditions that permit an agent capable of doing so to enter a cell and perform its intended function. In one embodiment, the term "suitable conditions" as used herein means physiological conditions.

The term "specificity" refers to the proportion of negative test results that are true negative test result. Negative test results include false positives and true negative test results.

The term "sensitivity" is meant to refer to the ability of an analytical method to detect small amounts of analyte. Thus, as used here, a more sensitive method for the detection of amplified DNA, for example, would be better able to detect small amounts of such DNA than would a less sensitive method. "Sensitivity" refers to the proportion of expected results that have a positive test result.

The term "reproducibility" as used herein refers to the general ability of an analytical procedure to give the same result when carried out repeatedly on aliquots of the same sample.

Sequencing platforms that can be used in the present disclosure include but are not limited to: pyrosequencing, sequencing-by-synthesis, single-molecule sequencing, second-generation sequencing, nanopore sequencing, sequencing by ligation, or sequencing by hybridization. Preferred sequencing platforms are those commercially available from Illumina (RNA-Seq) and Helicos (Digital Gene Expression or "DGE"). "Next generation" sequencing methods include, but are not limited to those commercialized by: 1) 454/Roche Lifesciences including but not limited to the methods and apparatus described in Margulies et al., Nature (2005) 437:376-380 (2005); and U.S. Pat. Nos. 7,244,559; 7,335,762; 7,211,390; 7,244,567; 7,264,929; 7,323,305; 2) Helicos BioSciences Corporation (Cambridge, MA) as described in U.S. application Ser. No. 11/167,046, and U.S. Pat. Nos. 7,501,245; 7,491,498; 7,276,720; and in U.S. Patent Application Publication Nos. US20090061439; US20080087826; US20060286566; US20060024711; US20060024678; US20080213770; and US20080103058; 3) Applied Biosystems (e.g. SOLiD sequencing); 4) Dover Systems (e.g., Polonator G.007 sequencing); 5) Illumina as described U.S. Pat. Nos. 5,750,341; 6,306,597; and 5,969,119; and 6) Pacific Biosciences as described in U.S. Pat. Nos. 7,462,452; 7,476,504; 7,405,281; 7,170,050; 7,462,468; 7,476,503; 7,315,019; 7,302,146; 7,313,308; and US Application Publication Nos. US20090029385; US20090068655; US20090024331; and US20080206764. All references are herein incorporated by reference. Such methods and apparatuses are provided here by way of example and are not intended to be limiting.

Methods and Compositions

Compositions and methods are provided for accurately identifying the set of peptides recognized by a T cell receptor in a given MHC context. The methods involve the generation of a library of polypeptides in which specific MHC binding domains, which provide the MHC context, are combined in a single polypeptide chain with a diverse library of peptide ligands. The diversity of the library is as previously defined. The single chain polypeptide may further comprise a domain that allows the peptide to be tethered to, or otherwise inserted into a cell surface.

The peptide ligand is from about 8 to about 20 amino acids in length, usually from about 8 to about 18 amino acids, from about 8 to about 16 amino acids, from about 8 to about 14 amino acids, from about 8 to about 12 amino acids, from about 10 to about 14 amino acids, from about 10 to about 12 amino acids. In preferred methods, the diversity is limited at the residues that anchor the peptide to the MHC binding domains, which are referred to herein as MHC anchor residues. The position of the anchor residues in the peptide are determined by the specific MHC binding domains. Class I binding domains have anchor residues at the P2 position, and at the last contact residue. Class II binding domains have an anchor residue at P1, and depending on the allele, at one of P4, P6 or P9. For example, the anchor residues for $IE^k$ are P1 {I,L,V} and P9 {K}; the anchor residues for HLA-DR15 are P1 {I,L,V} and P4 {F, Y}. Anchor residues for DR alleles are shared at P1, with allele-specific anchor residues at P4, P6, P7, and/or P9.

The library can be provided in the form of a polynucleotide, e.g. a coding sequence operably linked to an expression vector; which is introduced by transfection, electroporation, etc. into a suitable host cell. Eukaryotic cells are preferred as a host, and may be any convenient host cell that can be transfected and selected for expression of a protein on the cell surface. Yeast cells are a convenient host, although are not required for practice of the methods.

Once introduced in the host cells, expression of the library is induced and the cells maintained for a period of time sufficient to provide cell surface display of the polypeptides of the library.

Selection for a peptide that binds to the TCR of interest is performed by combining a multimerized TCR with the population of host cells expressing the library. The multimerized T cell receptor for selection is a soluble protein comprising the binding domains of a TCR of interest, e.g. α/β, TCRγ/δ, and can be synthesized by any convenient method. The TCR may be a single chain, or a heterodimer. In some embodiments, the soluble TCR is modified by the addition of a biotin acceptor peptide sequence at the C terminus of one polypeptide. After biotinylation at the acceptor peptide, the TCR can be multimerized by binding to biotin binding partner, e.g. avidin, streptavidin, traptavidin, neutravidin, etc. The biotin binding partner can comprise a detectable label, e.g. a fluorophore, mass label, etc., or can be bound to a particle, e.g. a paramagnetic particle. Selection of ligands bound to the TCR can be performed by flow cytometry, magnetic selection, and the like as known in the art.

Rounds of selection are performed until the selected population has a signal above background, usually at least three and more usually at least four rounds of selection are performed. In some embodiments, initial rounds of selection, e.g. until there is a signal above background, are performed with a TCR coupled to a magnetic reagent, such as a superparamagnetic microparticle, which may be referred to as "magnetized". Herein incorporated by reference, Molday (U.S. Pat. No. 4,452,773) describes the preparation of magnetic iron-dextran microparticles and provides a summary describing the various means of preparing particles suitable for attachment to biological materials. A description of polymeric coatings for magnetic particles used in high gradient magnetic separation (HGMS) methods are found in U.S. Pat. No. 5,385,707. Methods to prepare superparamagnetic particles are described in U.S. Pat. No. 4,770,183. The microparticles will usually be less than about 100 nm in diameter, and usually will be greater than about 10 nm in diameter. The exact method for coupling is not critical to the practice of the invention, and a number of alternatives are known in the art. Direct coupling attaches the TCR to the particles. Indirect coupling can be accomplished by several methods. The TCR may be coupled to one member of a high affinity binding system, e.g. biotin, and the particles attached to the other member, e.g. avidin. Alternatively one may also use second stage antibodies that recognize species-specific epitopes of the TCR, e.g. anti-mouse Ig, anti-rat Ig, etc. Indirect coupling methods allow the use of a single magnetically coupled entity, e.g. antibody, avidin, etc., with a variety of separation antibodies.

Alternatively, and in a preferred embodiment for final rounds of selection, the TCR is multimerized to a reagent having a detectable label, e.g. for flow cytometry, mass cytometry, etc. For example, FACS sorting can be used to increase the concentration of the cells of having a peptide ligand binding to the TCR. Techniques include fluorescence activated cell sorters, which can have varying degrees of sophistication, such as multiple color channels, low angle and obtuse light scattering detecting channels, impedance channels, etc.

After a final round of selection, polynucleotides are isolated from the selected host cells, and the sequence of the selected peptide ligands are determined, usually by high throughput sequencing. It is shown herein that the selection process results in determination of a set of peptides that are bound by the TCR in the specific HLA context. The biological activity of these ligands in the activation of T cells has been validated. The set of selected ligands provides information about the restrictions on amino acid positions required for binding to the T cell receptor. Usually a plurality of peptide ligands are selected, e.g. up to 10, up to 100, up to 500, up to 1000 or more different peptide sequences.

The sequence data from this selected set of peptide ligands provides information about the restrictions on amino acids at each position of the peptide ligand. This can be shown graphically, see FIG. 3A-3B, or FIG. 6B-6C for examples. The restrictions can be particularly relevant at the residues contacting the TCR. Data regarding the restrictions on amino acids at positions of the peptide are input to design a search algorithm for analysis of public databases. The results of the search provide a set of peptides that meet the criteria for binding to the TCR in the MHC context. The search algorithm is usually embodied as a program of instructions executable by computer and performed by means of software components loaded into the computer.

Also provided herein are software products tangibly embodied in a machine-readable medium, the software product comprising instructions operable to cause one or more data processing apparatus to perform operations comprising: generating a n×20 matrix from the positional frequencies of selected peptide ligands obtained by the screening methods of the invention, where n is the number of amino acid positions in the peptide ligand library. A cutoff of amino acid frequencies is set, e.g. less than 0.1, less than 0.05, less than 0.01, and frequencies below the cutoff are set to zero. A database of sequences, e.g. a set of human polypeptide sequences; a set of pathogen polypeptide sequences, a set of microbial polypeptide sequences, a set of allergen polypeptide sequences; etc. are searched with the algorithm using an n-position sliding window alignment with scoring the product of positional amino acid frequencies from the substitution matrix. An aligned segment containing at least one amino acid where the frequency is below the cutoff is excluded as a match. The results of the search can be output as a data file in a computer readable medium The peptide sequence results and database search results may be provided in a variety of media to facilitate their use. "Media" refers to a manufacture that contains the expression repertoire information of the present invention. The databases of the present invention can be recorded on computer readable media, e.g. any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a recording of the present database information. "Recorded" refers to a process for storing information on computer readable medium, using any such methods as known in the art. Any convenient data storage structure may be chosen, based on the means used to access the stored information. A variety of data processor programs and formats can be used for storage, e.g. word processing text file, database format, etc.

As used herein, "a computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

A variety of structural formats for the input and output means can be used to input and output the information in the computer-based systems of the present invention. Such presentation provides a skilled artisan with a ranking of similarities and identifies the degree of similarity contained in the test expression repertoire.

The search algorithm and sequence analysis may be implemented in hardware or software, or a combination of both. In one embodiment of the invention, a machine-readable storage medium is provided, the medium comprising a data storage material encoded with machine readable data which, when using a machine programmed with instructions for using said data, is capable of displaying any of the datasets and data comparisons of this invention. In some embodiments, the invention is implemented in computer programs executing on programmable computers, comprising a processor, a data storage system (including volatile and non-volatile memory and/or storage elements), at least one input device, and at least one output device. Program code is applied to input data to perform the functions described above and generate output information. The output information is applied to one or more output devices, in known fashion. The computer may be, for example, a personal computer, microcomputer, or workstation of conventional design.

Each program can be implemented in a high level procedural or object oriented programming language to communicate with a computer system. However, the programs can be implemented in assembly or machine language, if desired. In any case, the language may be a compiled or interpreted language. Each such computer program can be stored on a storage media or device (e.g., ROM or magnetic diskette) readable by a general or special purpose programmable computer, for configuring and operating the computer when the storage media or device is read by the computer to perform the procedures described herein. The system may also be considered to be implemented as a computer-readable storage medium, configured with a computer program, where the storage medium so configured causes a computer to operate in a specific and predefined manner to perform the functions described herein.

Further provided herein is a method of storing and/or transmitting, via computer, sequence, and other, data collected by the methods disclosed herein. Any computer or computer accessory including, but not limited to software and storage devices, can be utilized to practice the present invention. Sequence or other data can be input into a computer by a user either directly or indirectly. Additionally, any of the devices which can be used to sequence DNA or analyze DNA or analyze peptide binding data can be linked to a computer, such that the data is transferred to a computer and/or computer-compatible storage device. Data can be stored on a computer or suitable storage device (e.g., CD). Data can also be sent from a computer to another computer or data collection point via methods well known in the art (e.g., the internet, ground mail, air mail). Thus, data collected by the methods described herein can be collected at any point or geographical location and sent to any other geographical location.

Reagents and Kits

Also provided are reagents and kits thereof for practicing one or more of the above-described methods. The subject reagents and kits thereof may vary greatly. Reagents of interest include reagents specifically designed for use in the methods of the invention. Such a kit may comprise a library of polynucleotides encoding a polypeptide of the formula P-$L_1$-β-$L_2$-α-$L_3$-T, where a diverse set of peptide ligands is provided. The polynucleotide library can be provided as a population of transfected cells, or as an isolated population of nucleic acids. Reagents for labeling and multimerizing a TCR can be included. In some embodiments the kit will further comprise a software package for analysis of a sequence database.

For example, reagents can include primer sets for high throughput sequencing. The kits can further include a software package for sequence analysis. The kit may include reagents employed in the various methods, such as labeled streptavidin, primers for generating target nucleic acids, dNTPs and/or rNTPs, which may be either premixed or separate, one or more uniquely labeled dNTPs and/or rNTPs, such as biotinylated or Cy3 or Cy5 tagged dNTPs, gold or silver particles with different scattering spectra, or other post synthesis labeling reagent, such as chemically active derivatives of fluorescent dyes, enzymes, such as reverse transcriptases, DNA polymerases, RNA polymerases, and the like, various buffer mediums, e.g. hybridization and washing buffers, prefabricated probe arrays, labeled probe purification reagents and components, like spin columns, etc., signal generation and detection reagents, e.g. streptavidin-alkaline phosphatase conjugate, chemifluorescent or chemiluminescent substrate, and the like.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed, site. Any convenient means may be present in the kits.

The above-described analytical methods may be embodied as a program of instructions executable by computer to perform the different aspects of the invention. Any of the techniques described above may be performed by means of software components loaded into a computer or other information appliance or digital device. When so enabled, the computer, appliance or device may then perform the above-described techniques to assist the analysis of sets of values associated with a plurality of peptides in the manner described above, or for comparing such associated values. The software component may be loaded from a fixed media or accessed through a communication medium such as the internet or other type of computer network. The above features are embodied in one or more computer programs may be performed by one or more computers running such programs.

Software products (or components) may be tangibly embodied in a machine-readable medium, and comprise instructions operable to cause one or more data processing apparatus to perform operations comprising: a) clustering sequence data from a plurality of immunological receptors or fragments thereof; and b) providing a statistical analysis output on said sequence data. Also provided herein are software products (or components) tangibly embodied in a machine-readable medium, and that comprise instructions operable to cause one or more data processing apparatus to perform operations comprising: storing and analyzing sequence data.

EXAMPLES

The following examples are offered by way of illustration and not by way of limitation.

Example 1

Mechanism for Specificity of T Cell Recognition of Peptide-MHC

In order to survey a universe of MHC-presented peptide antigens whose numbers greatly exceed the diversity of the T cell repertoire, T cell receptors (TCRs) are thought to be crossreactive. However, experimentally measuring the extent of TCR cross-reactivity has not been achieved. We developed a system to identify MHC-presented peptide ligands by combining TCR selection of highly diverse yeast-displayed peptide-MHC libraries with deep sequencing. While we identified hundreds of peptides reactive with each of five different mouse and human TCRs, the selected peptides possessed TCR recognition motifs that bore a close resemblance to their known antigens. This structural conservation of the TCR interaction surface allowed us to exploit deep sequencing information to computationally identify activating microbial and self-ligands for human autoimmune TCRs. The mechanistic basis of TCR cross-reactivity described here enables effective surveillance of diverse self and foreign antigens, but without requiring degenerate recognition of non-homologous peptides.

T cells are central to many aspects of adaptive immunity. Each mature T cell expresses a unique αs T cell receptor (TCR) that has been selected for its ability to bind to peptides presented by major histocompatibility complex (MHC) molecules. During the course of T cell development, survival, and effector functions, a given TCR surveys a broad landscape of self and foreign peptides and only responds to ligands whose engagement exceeds certain affinity, kinetic and oligomerization thresholds. Unlike antibodies, TCRs generally have low affinity for ligands (KD~1-100 μM), which has been speculated to facilitate rapid scanning of peptide-MHC (pMHC).

Structural studies of TCR-pMHC complexes have revealed a binding orientation where, generally, the TCR CDR1 and CDR2 loops make the majority of contacts with the tops of the MHC helices while the CDR3 loops, which are conformationally malleable, primarily engage the peptide presented in the MHC groove. The low affinity and fast kinetics of TCR-pMHC binding, combined with conformational plasticity in the CDR3 loops, would seem to facilitate cross-reactivity with structurally distinct peptides presented by MHC. Indeed, given that the calculated diversity of potential peptide antigens is much larger than TCR sequence diversity, and certainly exceeds the number of T cells in an individual, TCR crossreactivity appears to be a biological imperative.

Crossreactive TCRs have been implicated in the pathogenesis of a number of autoimmune diseases, and have been proposed to explain why sequential infections in mice result in protective differences in immune pathology and the hierarchy of immunodominance. In humans, there is a growing recognition that vaccination can have a more general impact on morbidity and mortality beyond the expected benefit in preventing the targeted disease. Nevertheless, the true extent of TCR cross-reactivity, and its role in T cell immunity, remains a speculative issue, largely due to the absence of quantitative experimental approaches that could definitively address this question. While many examples exist of TCRs recognizing substituted or homologous peptides related to the antigen, such as altered peptide ligands, most of these peptides retain similarities to the wild-type peptides and are recognized in a highly similar fashion. Only a handful of defined examples exist of a single TCR recognizing non-homologous sequences. Examples from nature are rare, and there has not been a robust methodology to identify non-homologous peptides cross-reactive with a given TCR using screening approaches.

One approach that has been used to estimate cross-reactivity utilizes pooled, chemically synthesized peptide libraries. Based on a calculation taking into account the assumed concentrations of each agonist peptide in the pools, and the aggregate EC50 of the pool in stimulating a T cell clone, it has been extrapolated that ~106 different peptides in mixtures containing ~$10^{12}$ different peptides were agonists. However, while this methodology has successfully isolated a handful of significantly diverse sequences, most studies using the technique find only close homologues to known peptides. Furthermore, these libraries were assayed based solely on bulk stimulatory ability, with only femtomolar concentrations of any given peptide and no knowledge of peptide loading in the MHC or binding to the TCR. Therefore, the contributions of weakly reactive peptides or rare sequences are extremely difficult to isolate.

A more accurate estimate of cross-reactivity requires the isolation of individual sequences from a library of MHC-presented peptides based upon binding to a TCR. Recently, we and others have created libraries of peptides linked to MHC via yeast and baculovirus display as a method to discover TCR ligands through affinity-based selections that rely on a physical interaction between the peptide-MHC and the TCR (Adams et al. (2011). Immunity 35, 681-693; Birnbaum et al. (2012). Immunol Rev 250, 82-101). However, these methods have so far not been used to address the broader question of TCR cross-reactivity, mainly due to the requirement of manually validating and sequencing individual library 'hits', which has restricted the approach to discovering small numbers of peptides.

Here, we use deep sequencing of yeast peptide-MHC libraries selected against five murine and human TCRs. Starting with ~$10^8$ transformant libraries, we discovered hundreds of unique peptide sequences recognized by each TCR. Strikingly, all peptide sequences bear TCR epitopes with close similarity to their previously known agonist antigens and engage the TCRs in structurally similar ways. With an understanding of this property, we created a computational algorithm to predict naturally occurring TCR ligands using data from our deep sequencing results. The algorithm identified thousands of previously unknown microbial and environmental peptides as well as several peptides of human origin predicted to cross-react with self-reactive TCRs derived from a patient with multiple sclerosis. We tested a diverse set of the putative TCR-reactive peptides and found 94% are able to elicit a T cell response. In general, TCR cross-reactivity does not appear to be characterized by broad degeneracy, but rather is constrained to a small number of TCR contact residue 'hotspots' on a peptide, while tolerating greater diversity at other positions. This understanding of the properties of TCR cross-reactivity has broad implications for ligand identification, vaccine design, and immunotherapy.

We developed a system for the rapid and sensitive detection of TCR-binding peptides presented by the murine class II MHC I-$E^k$. This represents an advance over previous reports of class II pMHC molecules displayed on the surface of yeast that did not show the ability to bind TCR (Birnbaum et al., supra; Boder et al. (2005). Biotechnol Bioeng 92, 485-491; Esteban and Zhao (2004). J Mol Biol 340, 81-95.; Jiang and Boder, 2010 Proc Natl Acad Sci USA 107, 13258-13263; Starwalt et al., 2003 Protein engineering 16, 147-156; Wen et al., 2008 J Immunol Methods 336, 37-44; Wen et al., 2011 Protein Eng Des Sel 24, 701-709). We were aided by a large compendium of biophysical data for the interaction of I-$E^k$ with several TCRs.

We designed our construct as a 'mini' single-chain MHC Aga2 fusion, with the truncated peptide binding $\alpha 1 \beta 1$ domains fused via a Gly-Ser linker. We linked the wild-type peptide MCC to the N-terminus via a Gly-Ser linker (FIG. 1A). The initial construct was correctly routed to the yeast surface but did not have the ability to bind to TCR, indicating the pMHC was not correctly folded (FIG. 1B). In order to rescue correct folding of the pMHC, we subjected the mini I-$E^k$ to error-prone mutagenesis combined with introduction of solubility-enhancing mutations.

Figure 8:
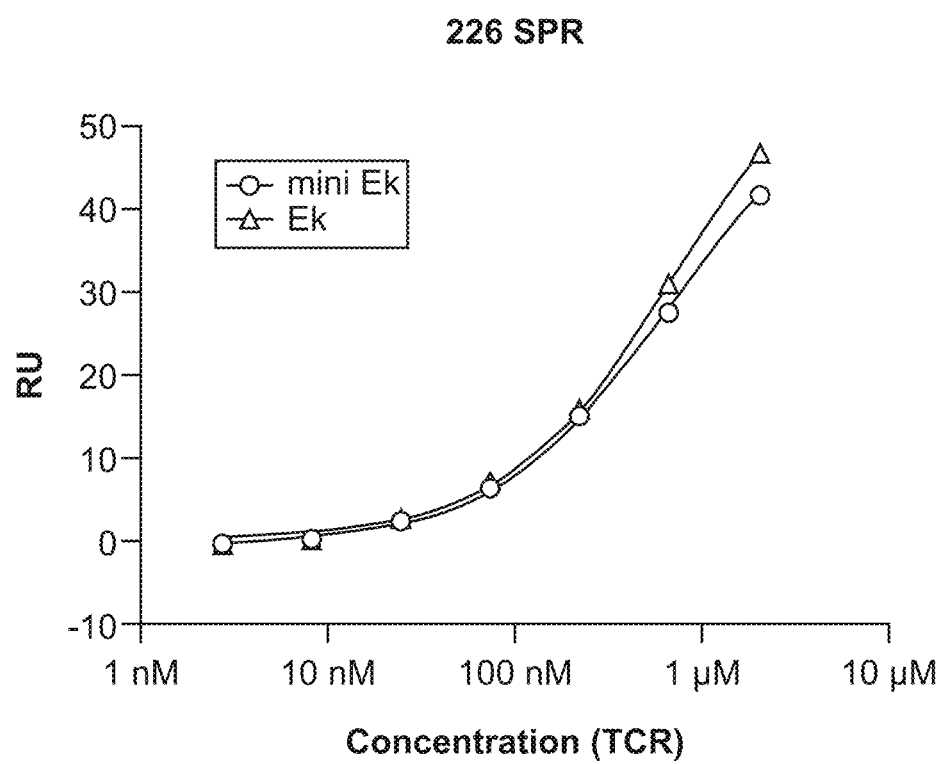
FIG. 8: Affinity measurement of 'mini' MCC-I-E$^k$. SPR measurement using soluble 226 TCR flowed over a surface containing either full length MCC-I-Ek (green) or "mini" MCC-I-Ek, as used for yeast selections
Figure 10:
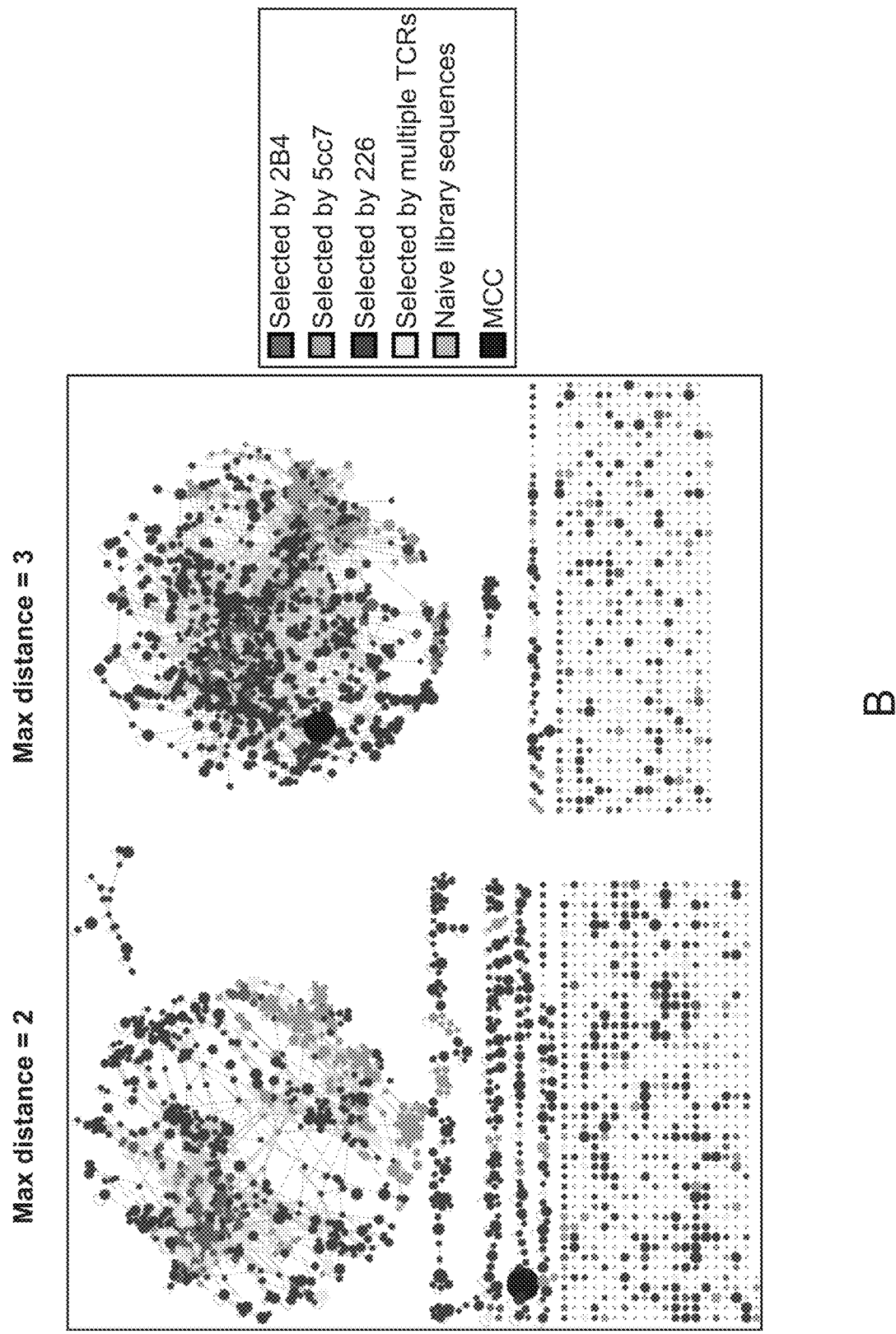
FIG. 10: Reads and distance clustering for selections of I-Ek library. (A) Total number of unique peptide sequences (top) and relative enrichment for 25 most abundant peptides (bottom) through 4 rounds of selection with 5cc7 and 226 TCRs. (B) Minimum distance clustering of all TCR sequences selected with maximum distance of 2 (left) and 3 (right) show different network topologies that coalesce into a single group. Compare to FIG. 3C.
Figure 13:
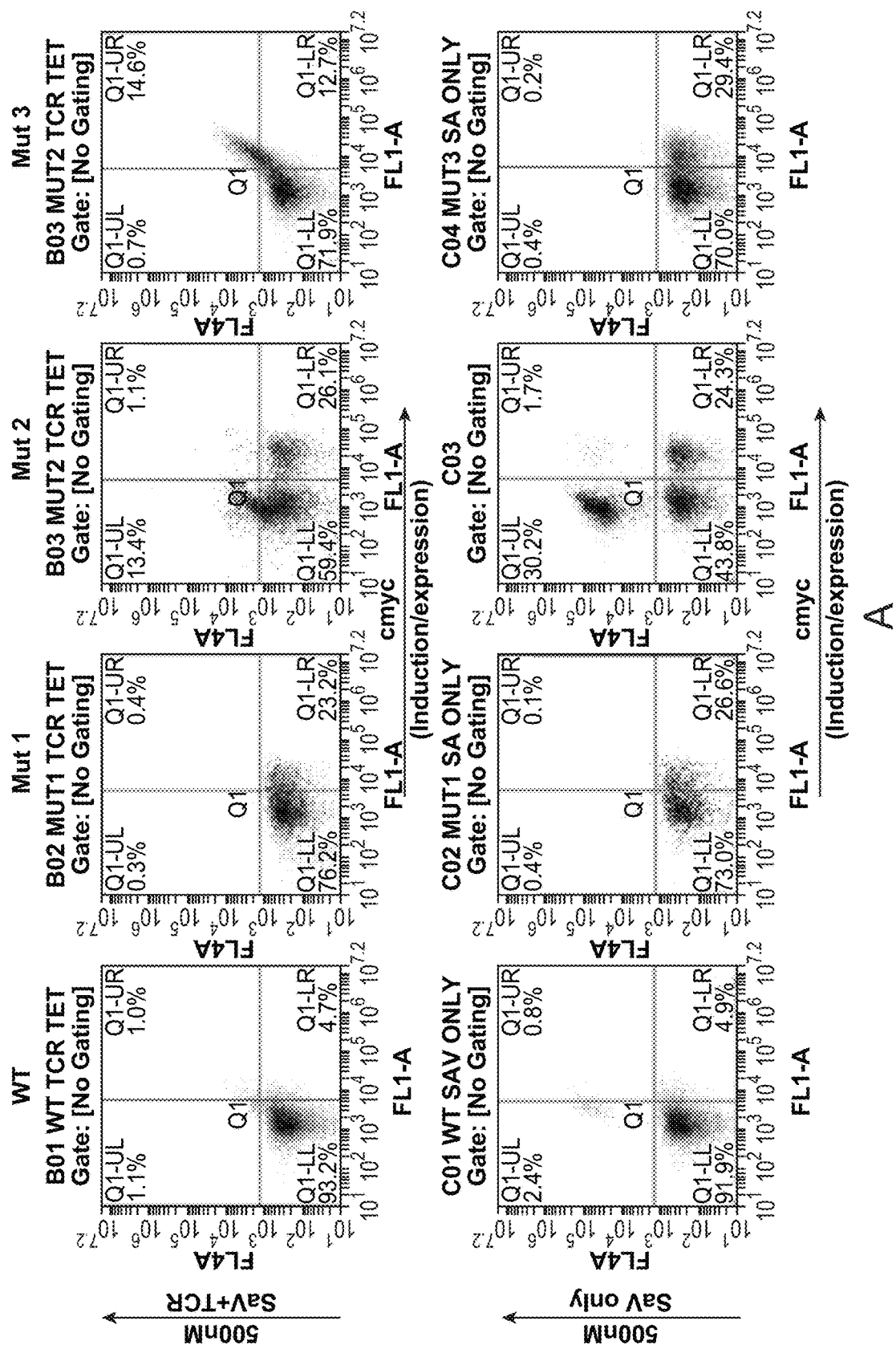
FIG. 13: Development of MBP-HLA-DR15 platform and selection with Ob.1A12 and Ob.2F3 TCRs. (A) Staining of WT HLA-DR15 as well as multiple potential variants with Ob.1A12 tetramer as well as anti HLA-DR15 antibodies. "Mut3" was the final construct used for all studies. (B) Mutations required for functional display of MBP-HLA-DR15 yeast display platform. (C) Plots for amino acid prevalence at the three primary TCR contact positions (P2 (magenta), P3 (green), and P5 (cyan)) show the peptide library enriches from even representation of all amino acids in the pre-selection library to a WT-like motif at each position. (D) Heatmap of amino acid preference by position for Ob.2F3 TCR (orange) shows little change from Ob.1A12 selections (see FIGS. 6B and 6C). (E) Minimum distance clustering of all TCR-selected with maximum distance of 3. Compare to FIGS. 3C, 10B, and 6D.
Figure 14:
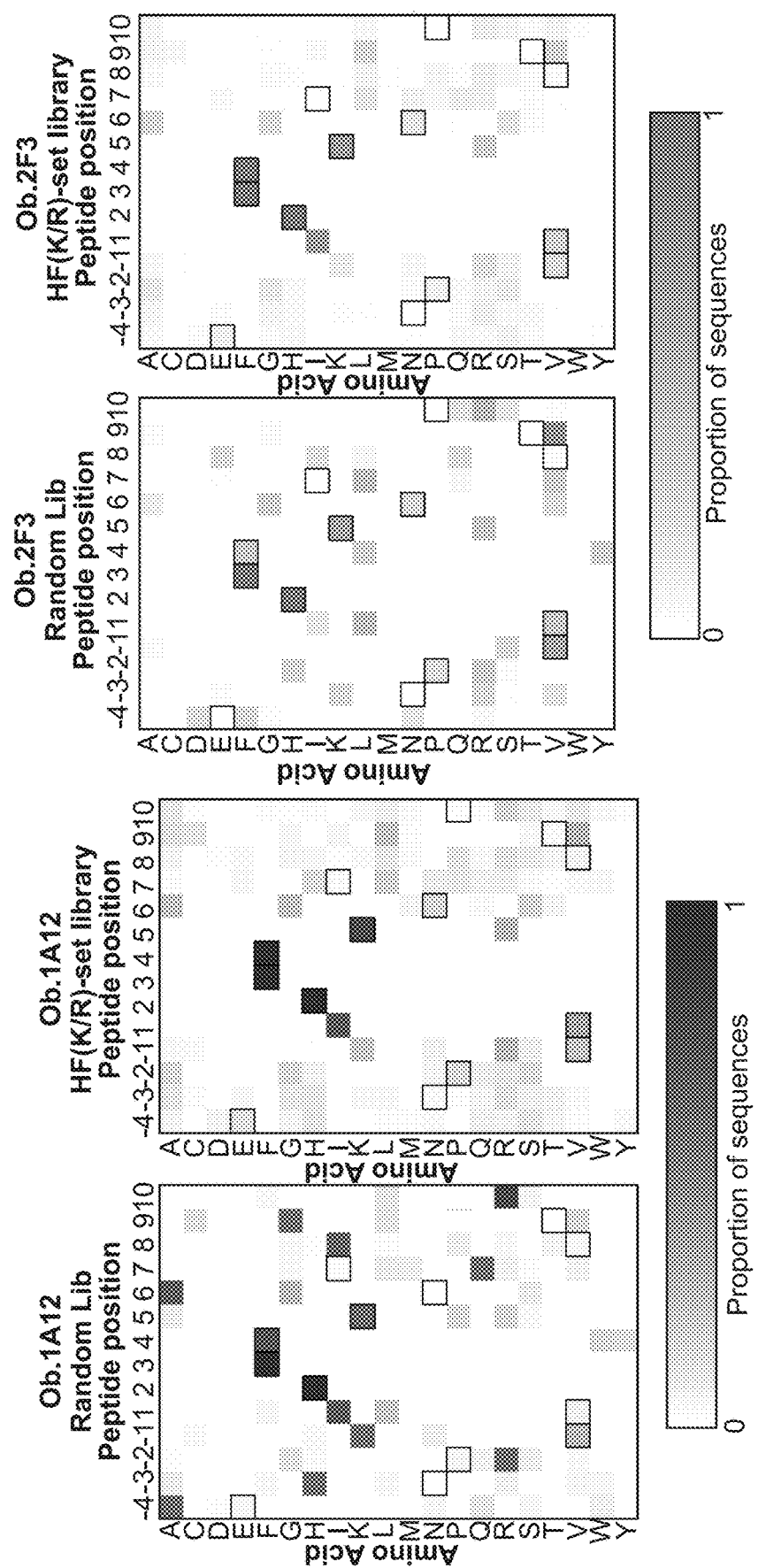
FIG. 14: Creation of substitution matrix based upon TCR selection of HLA-DR15 libraries for prediction of naturally occurring peptide ligands. (A) Heatmaps for selection of library with P2 His, P3 Phe, and P5 Lys/Arg set to determine relative importance of residues more distal to TCR binding hotspot. Selections for Ob.1A12 (purple, right) and Ob.2F3 (orange, right) look extremely similar. (B) Covariation analysis between P(−2) and P(−1) positions for Ob.1A12 (purple, left) and Ob.2F3 (orange, right) show no significant covariation between residues, allowing for assumption of independently varying positions. No covariation for any other positions noted.
Figure 15:
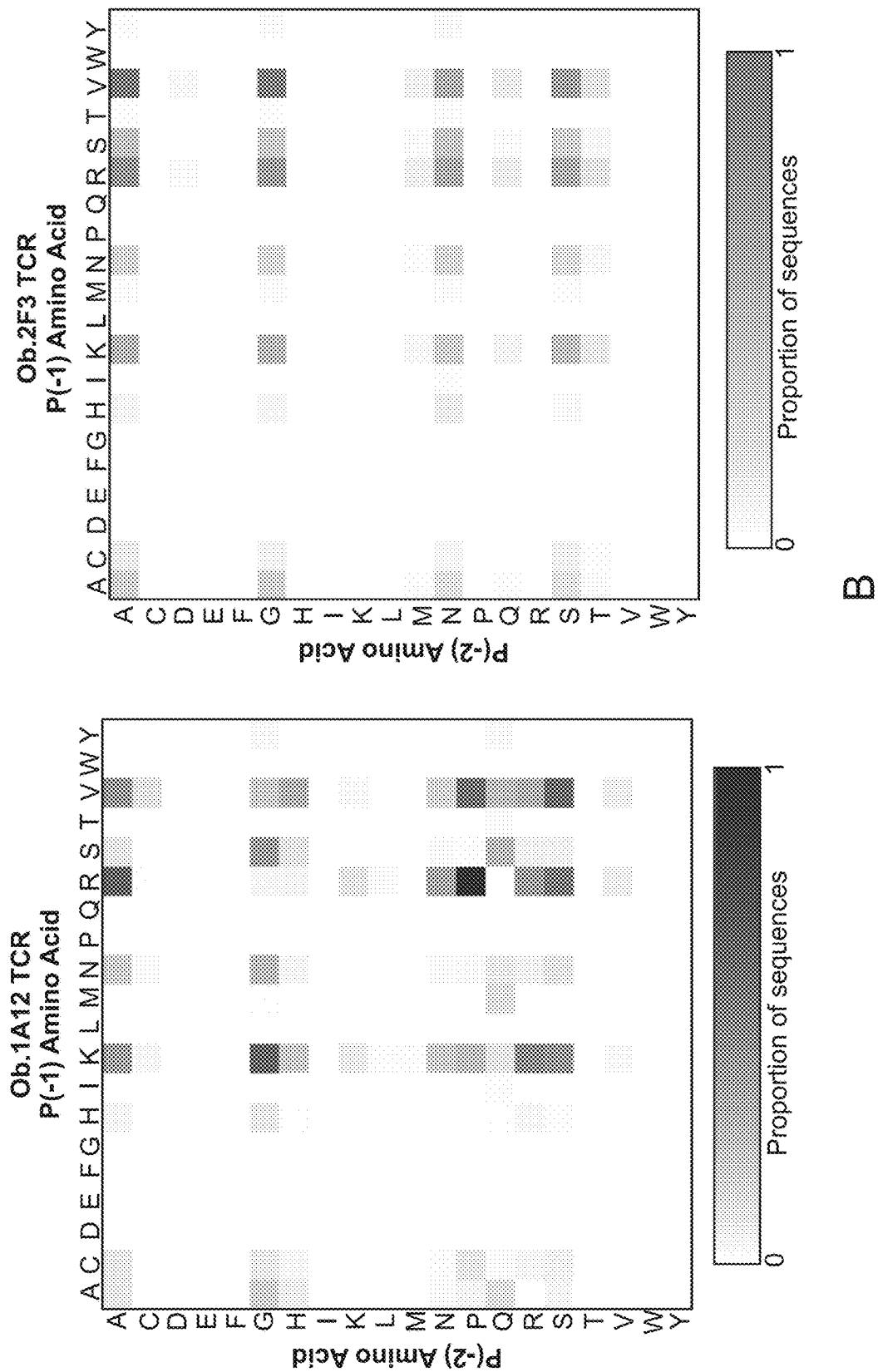
FIG. 15: Sequences of constructs, SEQ ID NO:1-6.

We selected this mutagenized mini scaffold for binding to the 2B4 TCR, which recognizes MCC-I-$E^k$ with moderate affinity and slow kinetics. Our selections yielded a functional construct with three mutations on the $\alpha 1$ domain—two solubilizing mutations in what was previously the $\alpha 1$-$\alpha 2$ interface and one mutation between the MHC helix and the beta sheets (FIG. 1B). Staining was further improved via introduction of three solubility-enhancing mutations of residues underneath the platform that are normally shielded from solvent by the MHC $\alpha 2$ and $\beta 2$ domains (FIG. 1B). None of the MHC residues mutated contacted either the peptide or the TCR. The evolved construct retained specific binding to several MCC-I-$E^k$ recognizing TCRs and showed comparable affinity to the wild-type pMHC (FIGS. 1B, 8).

We then created a peptide library tethered to the MHC construct for display on yeast. Based upon the recently solved 2B4-MCC-I-Ek structure, we mutagenized the peptide from P(-2) to P10 (FIG. 1C). Limited diversity was introduced at the two most distal residues and the primary MHC-binding anchor residues at P1 and P9 to maximize the number of peptides capable of being correctly displayed by the MHC (FIG. 1C). This library had a theoretical sequence diversity of $5.3 \times 10^{13}$, although only $1.8 \times 10^8$ sequences were represented in our library due to the limits of transformation efficiency.

Our first attempts at screening involved 'manual curation' of selections conducted with multivalent TCR. The library showed enrichment after three rounds of selection using highly avid TCR-coated streptavidin beads followed by a higher stringency 'polishing' round of selection using TCR tetramers. The three peptides recovered via sequencing of 12 individual, hand picked clones after selection were related to the WT MCC peptide—the P2, P5, and P8 TCR contacts were all conserved, while P3 showed highly conservative Tyr to Phe mutation (FIG. 1D). These results suggested that a WT-like TCR recognition motif was highly favored. We surmised that these enriched WT sequences present in the later rounds dominated the selections, preventing alternative, potentially non-homologous sequences enriched in early rounds from being recovered. For this reason, we turned to deep sequencing at each step of the selection process to recover all enriched clones.

Figure 2:
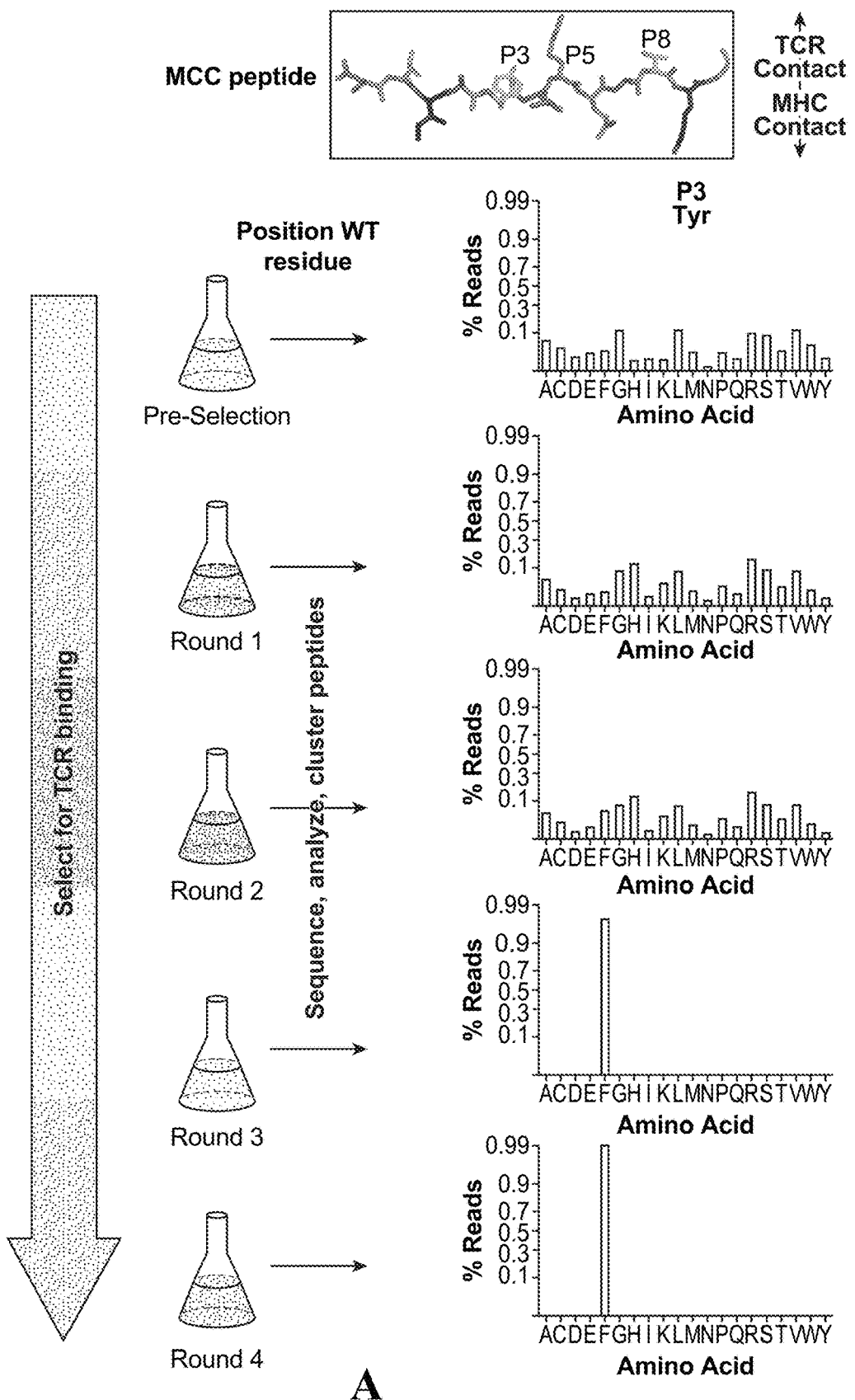
FIG. 2: Deep sequencing of peptide selections on I-E$^k$ converges on one dominant epitope for 2B4 TCR recognition. (A) Plots for amino acid prevalence at the three primary TCR contact positions (P3 (cyan), P5 (magenta), and P8 (orange)) show the peptide library enriches from even representation of all amino acids in the pre-selection library to a WT-like motif at each position. A secondary preference can be seen at P5 and P8 in round 3 but is outcompeted by round 4. (B) Sequence enrichment of 250 most abundant peptides show a convergence from a broad array of sequences to a few related clones. Area in grey represents all clones other than the most prevalent 250. (C) Comparison of total number of peptides and prevalence of 10 most abundant peptides for each round of selection. See also FIG. 9.

Deep sequencing of selections for TCR-binding peptides. Analysis of the pooled yeast library DNA after each successive round of selection via deep sequencing showed enrichment from an essentially random distribution of amino acids to a highly WT-like TCR recognition motif (FIGS. 2A, 9A). After the third round, there were nonhomologous amino acids at P5 and P8 selected above background (Met and Ser for P5, Ile and Leu for P8) that were outcompeted by the WT-like motif by the final round of selection. The P3 position converged to Phe, homologous but not identical to the Tyr in the WT peptide (FIG. 2A) Overall, the number of unique peptides observed via deep sequencing progressed from 132,000 unique in-frame peptides observed in the sequenced portion of pre-selection library to only 207 unique peptides after the 3rd round of selection (FIGS. 2B, 2C, 9A, 9B). By the final round of selection, most of the library was dominated by a handful of sequences, matching the result obtained by manual curation (FIGS. 1D, 2B, 2C).

Figure 3:
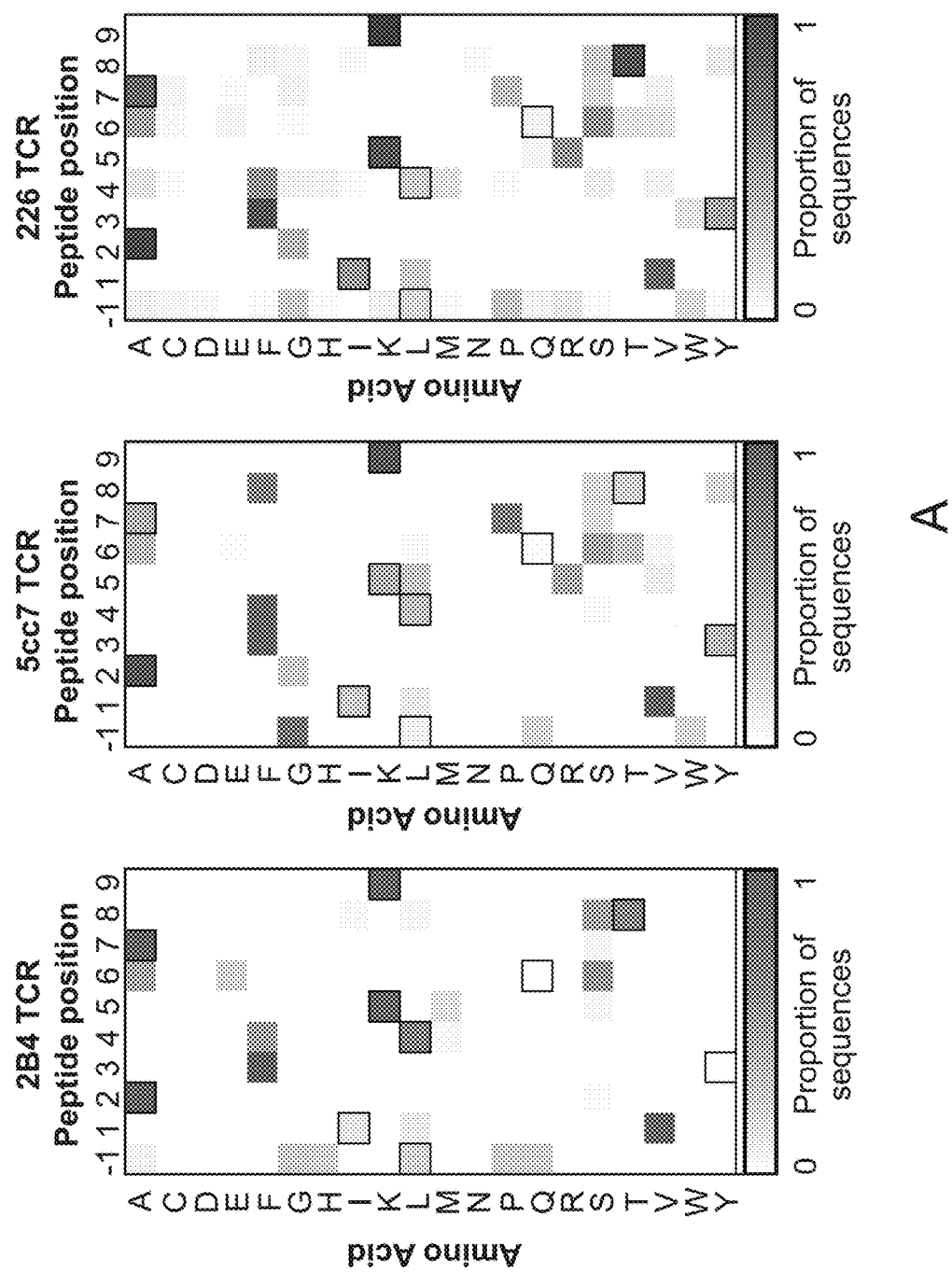
FIG. 3: Three different MCC/I-E$^k$ reactive TCRs require a WT-like recognition motif in the peptide antigens. (A) Heatmaps of amino acid preference by position for 2B4 (left, red) 5cc7 (center, green) and 226 (right, blue) TCRs. The sequence for MCC is represented via outlined boxes. TCR contact residues are labeled red on x axis. (B) Covariation analysis of TCR contact positions P5 (x axis) and P8 (y axis) show distinct coupling of amino acid preferences. (C) Minimum distance clustering of all TCR sequences selected above background show sequences for all TCRs form one large cluster with MCC (black circle, not represented in library but added for reference). Sequence cluster placed in a representation of whole-library sequence space (left: 1×magnification, center: 1000× magnification) for reference. See also FIG. 10.

We therefore chose to conduct all analysis after round 3, since the data consisted of enriched clones that had not yet converged on a small number of sequences. We were also able to track the enrichment profile of individual peptides, finding most peptides enriched roughly 50-fold between rounds (FIGS. 2B, 9B). We repeated the selections with two other TCRs reactive to MCC-I-$E^k$: 226 and 5cc7. We analyzed enrichment for each TCR after the third round of selection, where there is enrichment for a binding motif but before complete convergence to a small number of sequences (FIGS. 2A, 3A, 9B, 10A). While all three TCRs retain a WT-like TCR recognition motif such as P5 Lys (indicated by the outlined boxes in the heatmaps), each TCR also shows some variation in positional preferences (FIG. 3A). For example, where 2B4 can recognize P5 Met, 5cc7 can accommodate P5 Leu, Val, and Arg. The P3 TCR contact position showed the least variance across all three TCRs, with either Phe or Tyr being required for 2B4 and 5cc7, and Phe, Tyr, or Trp being required for 226 (FIG. 3A).

While each TCR recognized a largely WT-like motif, each recognized a different number of unique peptide sequences (FIG. 10A). 2B4 showed the highest stringency for its ligands, with only 207 sequences recovered from the selection that had enriched above the maximum background frequency of $1\times10^{-4}$ observed in any pre-selected clone. 226, as previously reported, showed a greater degree of cross-reactivity, able to recognize 897 unique peptide sequences. The larger number of peptides recognized was largely a function of a higher tolerance for substitutions on TCR-neutral and MHC-contacting residues, such as at positions P(−1) and P4 (FIG. 3A).

The large collection of peptides recovered via deep sequencing enabled us to apply a co-variation analysis to discover intra-peptide structure-activity relationships that were not previously accessible with traditional single residue substitution analysis (FIG. 3B). By using co-variation analysis of the central P5 residue and the C-terminal P8 residue, a pattern emerged: the native, MCC-like 'up-facing' TCR-contact motifs for each TCR (P5 Lys, P8 Ser/Thr) were strongly correlated, while the altered residues (P5 Ser/P8Leu for 2B4, P5 Leu or Arg/P8 Phe for 5cc7) were independently segregated (FIG. 3B). Therefore, the reason some of these TCR contacts were not previously described is that they do not occur independently. Instead, coupled changes across a network of peptide residues may be required to retain TCR binding. These results highlight a degree of cooperativity in the composition of residues comprising a 'TCR epitope' that is clearly revealed with deep sequencing. Furthermore, such intra-peptide residue coupling reveals that cross-reactivity can occur through mutually compensatory substitutions to the parent peptide.

While the selected ligands for all three TCRs possessed shared features, each TCR also selected for a subset of sequences that were not selected by the other two. We wished to determine if these sequences were part of the larger parent MCC-like peptide family or constituted distinct families of peptide sequences. To determine this, we applied distance clustering to all of the peptides selected for all three TCRs (FIG. 3C). We found that while sequences recognized by individual TCRs clustered most closely to each other, essentially all of the selected sequences formed one large cluster of peptides no more than three amino acids different than at least one other peptide in the cluster (FIG. 3C, 101B). This suggests that while each TCR has unique recognition criteria, the three TCRs recognized many of the same peptides. Furthermore, peptides that were recognized by all three TCRs are related to a common specificity domain, and importantly, to the parent MCC ligand.

Even though we conducted unbiased selections of random libraries, the only ligands that were recovered were remarkably similar to the WT ligand at the TCR interface. Indeed, we attempted to prevent the occurrence of wild-type like peptides from being selected by creating a peptide library that suppressed the Lysine codon at P5, but that retained diversity at all other positions. Nevertheless, these 'K-less' libraries failed to select for any TCR tetramer-staining clones when selected with 2B4 TCR. This experiment showed that the recovery of the wild-type TCR binding motifs in the original library was not simply due to wild-type like sequences suppressing the appearance of non-homologous crossreactive peptides.

Functional characterization of I-Ek library hits. We tested the signaling potencies and affinities of a subset of peptides selected for TCR binding. We synthesized 44 of the library peptides selected for binding to various subsets of the TCRs and examined their ability to stimulate T cell blasts from 2B4 and 5cc7 transgenic mice as assayed by CD69 upregulation and IL-2 production. The majority of the peptides predicted to bind 2B4 (19/19) and 5cc7 (17/21) expressing T cells induced CD69 upregulation (FIGS. 4A, 4B, 11A-D). The peptides had a wide range of potencies, with EC50s varying by several logs, including ~50-fold more potent than the wild-type peptide MCC (colored red). When we compared the presence of the MCC-like TCR recognition epitope with TCR signaling, we found that in general, sequences that shared the MCC-like epitope at all three major TCR contacts (colored blue) were more potent in inducing signaling than those peptides that were more distantly related (colored black) (FIGS. 4A, 4B), speaking to the functional dominance of the wild-type motifs. We also tested the peptides selected for binding to one TCR for their ability to crossreact with the other MCC-reactive T cells. Surprisingly, a large proportion of these peptides potently activated TCR signaling (FIGS. 4A, 4B, 11A-D).

Figure 4:
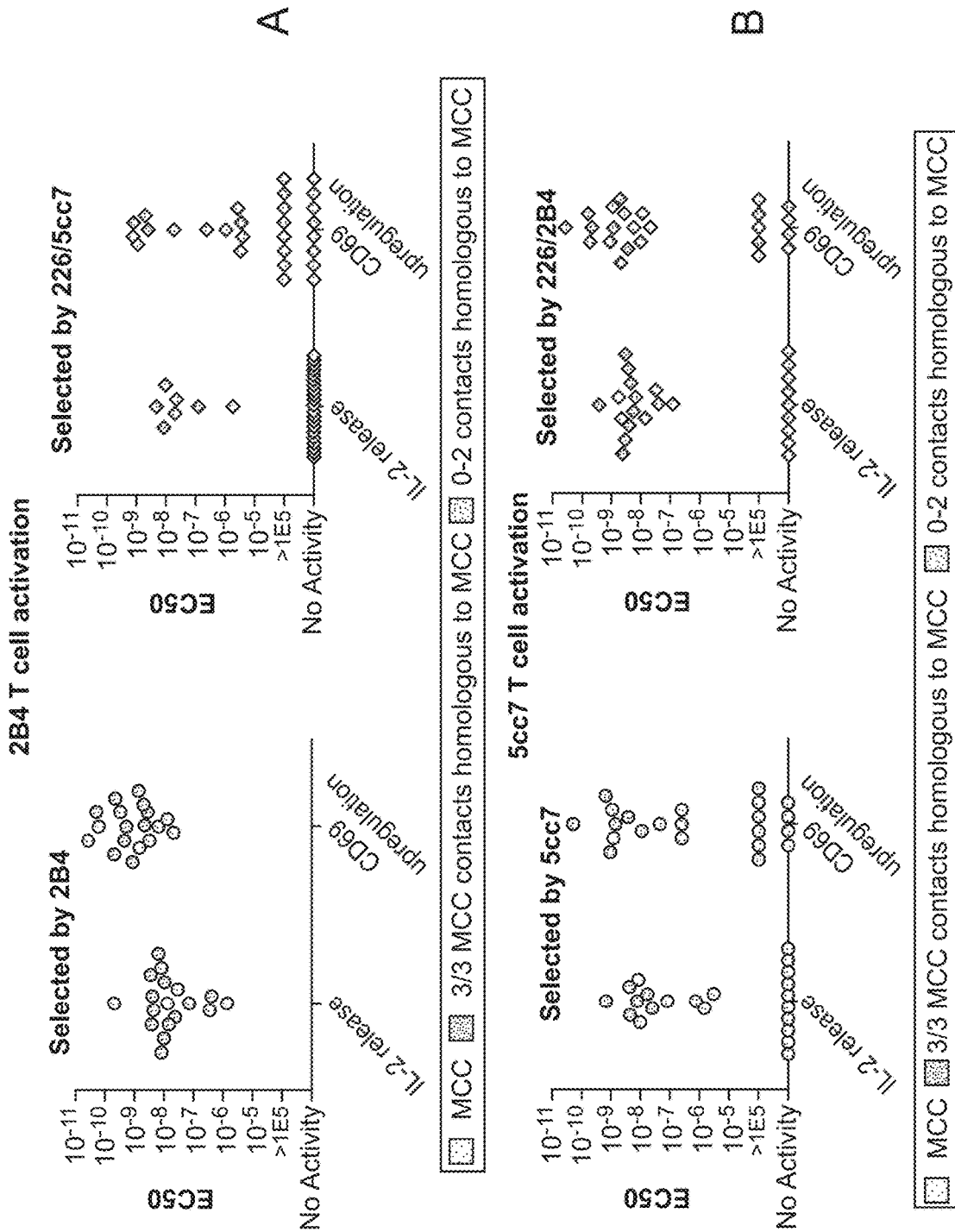
FIG. 4: Relationships between affinity and activity of peptides selected for binding to IE$^k$-reactive TCRs. (A) EC50s of IL-2 release and CD69 upregulation for 2B4 T cells with either peptides selected from library, plus MCC (red) (left), or peptides selected for a TCR other than the one tested (right). Sequences with close homology to MCC are represented in blue. Sequences that do not share 3/3 TCR contacts with MCC are in black. (B) EC50s as in A, but for 5cc7 T cells. (C) Correlation between pMHC-TCR affinity and peptide signaling potency. Each data point represents one peptide. See also FIG. 11.

There was a significant difference in EC50s between peptides that were selected to bind to 2B4 versus the 5cc7/226-selected peptides tested for 2B4 T cell activation. For 5cc7 the EC50s for the two groups (5cc7-selected versus cross-reactive with 2B4/226-selected) are essentially identical. In general, the sequences that showed the most robust activation were again the ones that most closely shared the MCC TCR binding epitope. We additionally chose nine peptides from our initial set of 46 and exchanged them into soluble I-Ek MHC for TCR affinity measurements via surface plasmon resonance (SPR). For 2B4 and 5cc7, TCR bound the pMHC of interest with affinities ranging from KD of ~1 µM (over 10-fold better than MCC) to those with binding only barely detectable at 100 µM TCR (FIG. 11E-F). When we compared the activity and affinity of our selected peptides, there is a loose but positive correlation between strength of TCR-pMHC binding and potency of activation (FIG. 4C). Several peptides with significantly different affinities show similar potencies (FIG. 4C).

Figure 5:
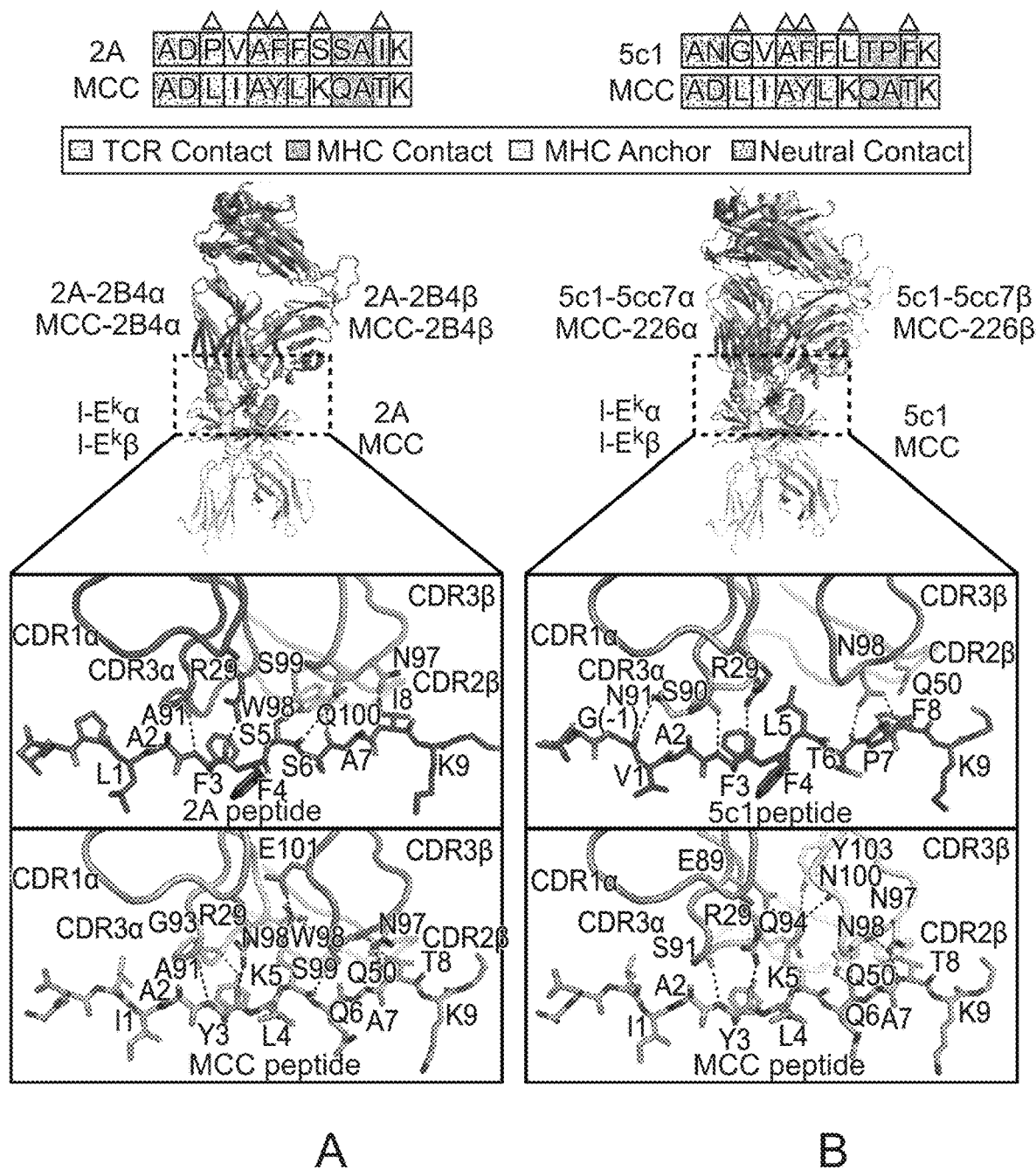
FIG. 5: Peptides distantly related to MCC show highly similar mechanism of recognition and linkages to the cognate antigen. Crystal structures of peptide-MHC/TCR complexes for 2A-I-E$^k$/2B4 and MCC-I-E$^k$/2B4 (PDB ID: 3QIB) (A) as well as 5c1-I-Ek/5cc7 and MCC-I-E$^k$/226 (PDB ID: 3QIU) (B) compared. TCR contacts are shown in magenta (noted with triangles). Each structure aligned based on MHC (top) shows very little change in overall binding geometry despite significant variation of peptide sequence. The TCRs accommodate differences in peptide sequence primarily through rearrangement of the TCR CDR3β (bottom). (C) TCR CDR loop footprints for 2B4 recognizing MCC and 2A peptides, 226 recognizing MCC and MCC K99E peptides, and 5cc7 recognizing 5c1 and 5c2 peptide show very little deviation. (D) Progression of sequences from MCC and 2A peptides. Each peptide is represented in deep sequencing results and differs by one TCR contact from the previous sequence. See also Table 1.

The structural basis of TCR recognition of cross-reactive peptides. To determine the molecular basis of the TCRs' ability to recognize the most diverse of the alternate peptides selected, we determined the crystal structures of 2B4 in complex with the library-derived 2A peptide (containing P5 Ser and P8 Ile) bound to I-$E^k$, as well as 5cc7 in complex with two library-derived peptides bound to I-$E^k$, 5c1 and 5c2 (containing P5 Leu/Arg and P8 Phe, respectively) (Table 1). When these complexes were aligned with previously solved complex structures of TCRs (2B4 and 226) binding to MCC-I-$E^k$, very little deviation in overall TCR-pMHC complex geometry from the parent complexes was observed (FIGS. 5A and 5B). Since the MCC-I-$E^k$-5cc7 complex is not solved, 5c1 and 5c2 were compared to MCC-I-Ek-226, which shares the TCRβ chain with 5cc7 and therefore likely retains a close footprint.

The contacts between TCR germline-derived CDR1/2 loops and MHC helices, which make up roughly 50% of the binding interface between TCR and pMHC, were essentially unchanged in the new peptide complexes versus MCC despite the difference in TCR contact residues in the peptides (FIG. 5C). When we examined the chemistry of MCC versus 2A, and MCC versus 5c1 peptide recognition by the respective TCRs, we saw the interaction between the TCRα CDR loops and the N-terminal half of the peptides are essentially invariant (FIGS. 5A and 5B, lower panels). Each peptide backbone makes a hydrogen bond at the P3 carbonyl with Arg29α in the TCR CDR1α loop. The contacts of 2B4 CDR3α with P2 and P3 in MCC and 2A are essentially identical (FIG. 5A, lower panels).

While an exact analogy cannot be made between 5cc7 recognizing 5c1 and 226 recognizing MCC due to sequence differences in their CDR3 loops, 5cc7 and 226 CDR3α loop conformations and peptide contacts are extremely similar (FIG. 5B, lower panels). The fact that all three MCC-reactive TCRs enrich for the same peptide residues at P2 and P3 (FIG. 3A) indicates that recognition peptides at their N-terminal contacts are highly conserved within this group (FIG. 5B, lower panels). In contrast, 2B4 and 5cc7β chain CDR loop interactions with the C termini of the peptides show marked changes to accommodate the non-MCC sequences. For 2B4, the CDR3β loop conformation completely rearranges to engage the alternate P5 and P8 residues on the 2A peptide (FIG. 5A, lower panels). Gln100β, a residue that makes no contact with the peptide in the 2B4-MCC complex structure, flips its side chain by 180 degrees to form hydrogen bonds with the peptide backbone carbonyl oxygens at P5 and P6 (FIG. 5A, lower panels). Similarly, the side chains of Trp98β and Ser99β form hydrogen bonds with the P5 Ser hydroxyl moiety (FIG. 5A). Asp101β, one of the main contacts with P5 Lys in MCC, also undergoes a rearrangement. Instead of contacting the peptide, the side chain forms a hydrogen bond with Ser95β on the other end of the CDR3β loop, significantly altering the overall topology of the loop.

In the 5c1-I-E$^k$/5cc7 complex, there are far fewer hydrogen bonds formed between the peptide and TCR due to the replacement of P5 Lys with Leu in the 5c1 peptide (FIG. 5B, lower panels). One side chain, Asn98β, changes its hydrogen bonding network from engaging only the carbonyl of P6 on the MCC peptide backbone to simultaneously interacting with the carbonyl oxygen of P6 and the amide nitrogen of P8 of the 501 peptide (FIG. 5B). The second peptide, 5c2, is recognized essentially identically by 5cc7 as 50 despite the substitution of P5 to Arg (Figure S5C). The substitution of a bulkier side chain at P8 (Phe instead of Thr), results in a rocking of 5cc7 such that the TCR C3 FG loop is translated by 15 Å relative to the MCC-226 structure (Figure S5D-E). The shift of the TCRβ chain is correlated with accommodation of a bulky hydrophobic residue Phe at P8 on the peptide. It is interesting to note that 50 and MCC differ by several logs in signaling potency (EC50 of 1.5 µM vs 8.4 nM) despite a relatively small difference in affinity (KD of 115 µM vs 41 µM). Indeed, all tested peptides with P8 Phe signal less efficiently than MCC-like peptides, even when affinities are closely matched (such as for 5c3, which binds to 5cc7 with a KD of 62 µM) (FIG. 11E-F). These structures raise the question if a minor tilt of the TCR relative to the MHC can have consequences for signaling.

Strikingly, upon closer inspection, we find that homologies between what appear to be unrelated peptide sequences emerge from sequence clustering and structural analysis. For example, close structural relationships between the interaction modes of the 2B4-selected peptides MCC and 2A are apparent even though the peptides show little homology at 4/5 TCR contact positions (FIG. 5A). We also set out to determine if we could identify intermediate sequences that would 'evolutionarily' link these two peptide sequences during the selection, given that both reside in the same sequence cluster (FIG. 3C).

Using our dataset of peptide sequences selected for 2B4 binding, we were able to populate a family of peptides that incrementally link MCC and 2A, with each peptide differing by only one TCR contact from the peptide before and after it (FIG. 5D). Thus, connectivity can be established between MCC and 2A through stepwise single amino acid drifts from their parent sequences.

Collectively, despite differences in peptide sequences, all MCC and library-peptide derived complexes share many common features with regards to docking geometry and interaction chemistry. Up-facing peptide residue sequence changes (e.g. P5, P8) are accommodated 'locally' in a structurally parsimonious fashion that preserves most of the parent MCC peptide complex features, as opposed to accommodation through large scale repositioning of the CDR loops on the pMHC surface.

Development and selection of a human MHC platform for yeast display. To exploit our technology to find ligands for TCRs relevant to human disease, we also engineered the human MHC HLA-DR15, an allele with genetic linkage to multiple sclerosis. For yeast surface display, HLA-DR15 was constructed comparably to the murine I-Ek β1α1 'mini' MHC with a peptide fused to the Nterminus (FIG. 6A). We chose to examine two closely-related TCRs, Ob.1A12 and Ob.2F3, that were cloned from a patient with relapsing-remitting multiple sclerosis and recognize HLADR15 bound to an immunodominant epitope of myelin basic protein (MBP, residues 85-99) peptide. These two TCRs utilize the same Vα-Jα and Vβ-Jβ gene segments and differ at one position in the CDR3α loop and two positions in CDR3β. Ob.1A12 TCR is sufficient to cause disease in a humanized TCR transgenic mouse model.

A structure of Ob.1A12 complexed with HLA-DR15-MBP revealed an atypical docking mode, with the TCR shifted towards the N-terminus of the peptide. Ob.1A12 recognition of the MBP peptide is focused on a P2-His/P3-Phe TCR contact motif, and to a lesser extent on P5 Lys (FIG. 6B). The initial wild-type MBP-HLA-DR15 yeast display construct was not stained by Ob.1A12 TCR tetramers (FIG. 6A). Therefore, as with the I-Ek platform, we subjected this construct to error prone mutagenesis and selected for binding with Ob.1A12. In this fashion, mutations were found that enabled functional display, as measured by tetramer staining.

Our final construct combined the most heavily selected mutation (Pro11Ser on HLA-DR15β) with two solubility-enhancing mutations on the bottom of the platform that were analogous to mutations required for I-Ek function (FIG. 6B). This construct stained robustly with Ob.1A12 and Ob.2F3 TCRs, as well as two MHC-specific antibodies (FIG. 6A). We designed a peptide library within the HLA-DR15 mini MHC scaffold to find novel Ob.1A12-binding peptides (FIG. 6A). Since Ob.1A12 binds its cognate pMHC shifted towards the N terminus of the peptide, we extended the library, randomizing from P(−4) to P10 compared to P(−2) to P10 for I-Ek (Hahn et al., 2005). The P1 and P4 positions, the strongest peptide anchors for HLA-DR15, were only afforded limited diversity.

The library was selected for binding to both Ob.1A12 and Ob.2F3 TCR tetramers and then each round was deep sequenced. We observed a strong convergence to a wild-type MBP-like TCR recognition motif for the primary Ob.1A12

TCR contacts (P2 His, P3 Phe, and P5 Lys) (FIG. 6B). Selections conducted with Ob.2F3 produced the same central 'HF' MBP-like motif while showing slightly different enrichment patterns at proximal residues (Figure S6D). Given the dominance of 'HF' in the selection results, we sought to determine if alternative cross-reactive TCR epitopes for Ob.1A12 would emerge if the up-facing 'HF' motif was suppressed.

We made a library that allowed every amino acid except for His at P2, Phe at P3, and Lys at P5 (FIG. 6C). The selected clones still converged to a central HF motif by register shifting towards the C-terminus of the peptide by one amino acid, allowing the previous P4 Phe anchor to be repurposed as the P3 TCR contact, and the P3 position of the library to become the new P2 His TCR contact (FIG. 6C). Furthermore, when we subsequently prevented both His and Phe at P2 and P3 in a new library to suppress potential register shifting, we did not isolate any Ob.1A12-binding peptides. These results show that the 'HF' motif is required for TCR recognition and its enrichment is a function of TCR preference, not any inherent biases caused by the library or MHC anchor positions of the peptide.

Clustering analysis of the selected peptides for both Ob.1A12 and Ob.2F3 showed that the selected peptides clustered with each other over the unselected peptides from the naïve library (FIG. 6D). The overall clustering topology of the selected peptides was different than the I-Ek selections: instead of a single network encompassing all peptides, there were two distinct clusters consisting of peptides no more than 4 amino acids different from each other (FIG. 6D). When the stringency of clustering is increased to allow no more than 3 amino acid differences, matching the analysis done for I-Ek, there were several more sparse clusters. Since Ob1.A12 and Ob.2F3 are so focused on the HF motif, there are fewer total hotspot residues distributed on the peptide compared to the MCC-reactive TCRs we studied.

High-confidence prediction of naturally occurring TCR-reactive peptides. The surprisingly limited tolerance of the TCRs for alternative ligands points to the feasibility of unambiguously identifying natural TCR ligands through selection with a random peptide library. However, library selections and deep sequencing alone are not sufficient to identify naturally occurring ligands for two reasons. First, the size of yeast libraries (~2×10$^8$ unique sequences) relative to all possible pMHC-displayed peptides makes it unlikely that any given naturally occurring peptide sequence will exist in the library. Second, the amino acid substitutions that are permitted at each position along the peptide represent a complex, and as our covariation analysis indicated, cooperative interplay between the peptide, MHC, and TCR that may not be well described by common substitution matrices such as BLOSUM. For example, even though manual inspection of Ob.1A12-binding sequences readily shows the WT-like 'HF' motif, blastp searches do not find MBP as a match even when constrained to the human proteome.

We therefore set out to develop an algorithm to use the aggregate data from our selection results to inform searches for candidate TCR antigens. First, we created a substitution matrix that would more accurately describe the probability of specific amino acid substitutions imparted by the selecting TCR. We hypothesized we could use the positional frequency information derived from our Ob.1A12 and Ob.2F3 deep sequencing data as a pMHC-TCR substitution matrix.

One potential complicating factor in using selection data as a substitution matrix is that the limited coverage of the libraries at every position of the peptide could lead to appearance of residue biases at non-critical (i.e. neutral) peptide positions that do not reflect actual selective pressure. To address this possibility, we created a new HLA-DR15-based library where we fixed the dominant Ob.1A12 binding motif (P2 His, P3 Phe, and P5 Lys/Arg) along with the P1 and P4 MHC-binding anchors, while the remaining residues were fully randomized. In this way, all peptides represented in the library contain the main motif required for Ob.1A12 binding and we could more accurately measure the occurrence of substitutions at other sites along the peptide.

When the selected libraries were sequenced, we found no dominant sequence, but rather a broad array of peptides that had enriched equally. While some proximal positions such as P(−1) and P(−2) still showed distinct residue preferences, other positions such as P7 and P8 showed less convergence relative to the original HLA-DR15 library. These selections provided critical granularity for what amino acids occur away from the TCR-binding 'hotspot' on the peptide, allowing us to construct a more reliable algorithm.

Figure 7:
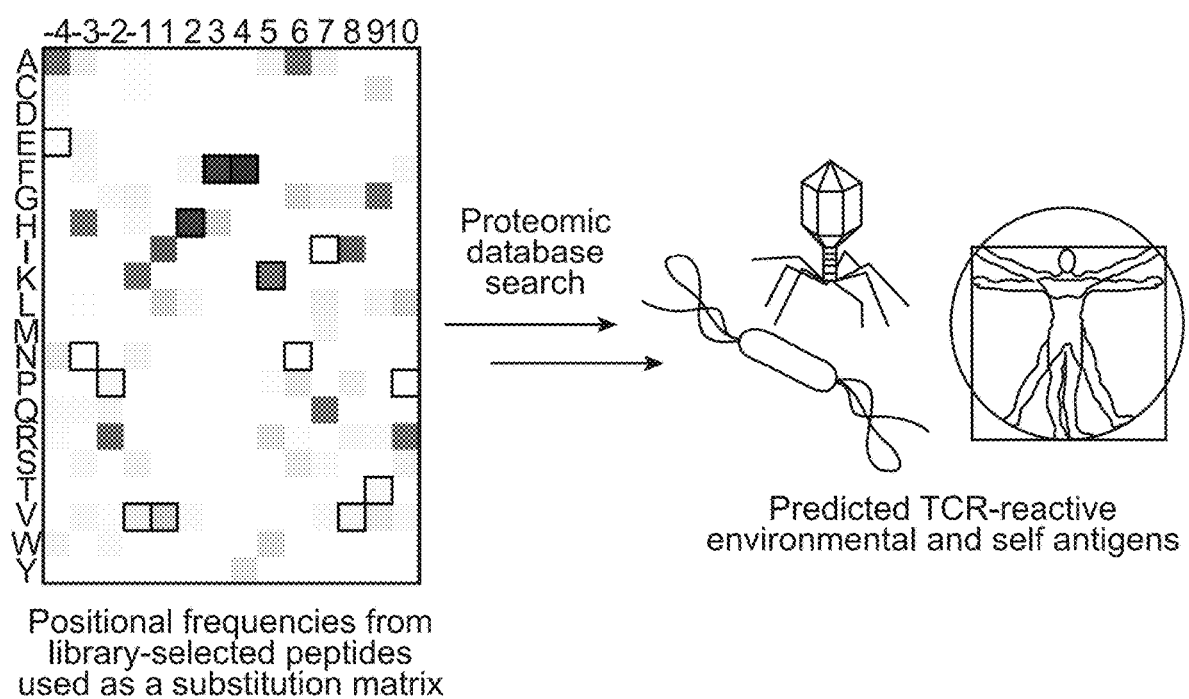
FIG. 7: Discovery of naturally occurring TCR ligands through deep sequencing and substitution matrix-based homology search. (A) Schematic for ligand search strategy, in which a positional substitution matrix is generated from deep sequencing data and then used to find naturally occurring peptides that are represented within the matrix. (B) Functional characterization of a selection of naturally occurring peptides with predicted activity. The peptides comprise a variety of microbial, environmental, and self antigens. Activity is tested via proliferation of T cells when exposed to peptide. Heatmaps are normalized to 10 μM dose of MBP peptide for each T cell clone.

We compiled the two 14×20 matrices consisting of the observed frequencies of the 20 amino acids at each of the 14 positions of the library peptides from the focused DR15 pMHC libraries with the 'HF' motif selected by Ob.1A12 and Ob.2F3 (FIG. 7A). Any amino acid with less than 1% prevalence at each position was excluded to minimize possible noise from PCR or read errors. Minimal residue covariation was observed for Ob.1A12 and Ob.2F3 selections, so each position was treated independently.

With this matrix in hand, we developed a peptide search algorithm. Each protein in the NR (NCBI) or human protein (Uniprot) databases was scanned using a 14 position sliding window and scored as a product of the positional substitution matrix (Cockcroft and Osguthorpe, (1991) FEBS letters 293, 149-152). In this way, a candidate peptide containing even a single disallowed substitution would be excluded as a possible hit. The search using the Ob.1A12 based matrix yielded 2331 unique NR hits and 13 human peptides, both including MBP. For the search based on the Ob.2F3 matrix, we had 4825 unique NR hits and 19 unique human peptides, again both including MBP. The peptide hits shared the central P(−1)-P5 motif of MBP but the flanking residues showed very little sequence homology to either MBP or to each other (FIG. 7B).

The predicted peptides are from diverse microbial sources, such as bacteria; environmental sources, such as antigens expressed by plants; and several peptides derived from proteins in the human proteome. To test our computationally predicted ligands for Ob.1A12 and Ob.2F3, we synthesized a diverse set comprising 27 of the potential environmental antigens as well as 6 novel human peptides predicted to cross-react with Ob.1A12 and Ob.2F3. The peptides were added to HLADR15 expressing antigen-presenting cells and incubated with the human T cell clones, and T cell proliferation was measured via 3H-thymidine incorporation. Of the 33 putative ligands, 26/27 of the environmental antigens and 5/6 of the human peptides induced proliferation for Ob.1A12 and/or Ob.2F3, a success rate of 94% (FIG. 7B).

The concept of TCR cross-reactivity is important because key aspects of T cell biology seemingly require recognition of diverse ligands, including thymic development, pathogen surveillance, autoimmunity and transplant rejection. In this study, we aimed to define the mechanisms underlying TCR specificity and cross-reactivity using a combinatorial, biochemical approach that yielded massive datasets based on direct selection. This has given us insight into the structural basis of TCR cross-reactivity and also provides a robust way to discover new peptides (or the original ligand) for a given TCR.

Our results clarify previous controversies on whether TCRs are highly cross-reactive or highly specific. We find that TCR cross-reactivity can be explained based on structural principles: peptides possess 'down-facing' residues that principally fill pockets in the MHC groove and 'up-facing' residues that primarily act to engage the TCR. If the criterion of crossreactivity is simply the number of unique peptide sequences that can be recognized by any given TCR, then TCRs do exhibit a high degree of cross-reactivity. Indeed, our selections are able to identify hundreds of peptides for each receptor. Given the fact that the libraries greatly undersample all possible sequence combinations it is likely that our hundreds of discovered peptides are indicative of thousands of different peptides can be recognized by the studied TCRs.

However, when cross-reactive peptides are examined en masse, we find central conserved TCR-binding (i.e. 'up-facing') motifs. TCR cross-reactivity is not achieved by each receptor recognizing a large number of unrelated peptide epitopes, but rather through greater tolerance for substitutions to peptide residues outside of the TCR interface, differences in residues that contact the MHC, and relatively conservative changes to the residues that contact the TCR CDR loops. The segregation of TCR recognition and MHC binding allow for TCRs to simultaneously accommodate needs for specificity and cross-reactivity, ensuring no 'holes' in the TCR repertoire without requiring degenerate recognition of antigen. This conclusion is consistent with previous studies on human self-reactive TCRs from multiple sclerosis patients: all stimulatory microbial peptides were found to share the primary TCR contact residues with the MBP self-peptide while substantial changes were permissible at the MHC interface.

Although this mechanism is general for αβ TCRs, recognition of nonhomologous antigens can occur to varying degrees in the TCR repertoire. The ability for one TCR to bind to multiple MHCs (e.g. alloreactivity); for one TCR to bind in multiple orientations on one MHC; for a peptide to non-canonically bind MHC (e.g. partially-filled peptide grooves); or for a TCR to have TCR-peptide contacts as a disproportionately large or small part of the overall interface (e.g. 'super-bulged' peptides) will grant some receptors a greater degree of epitope promiscuity. Class I and class II MHC specific TCRs may exhibit different degrees of cross-reactivity as a consequence of the 'low lying' peptides in the class II groove, versus the elevated or 'higher profile' peptides presented by class I.

In retrospect, a close inspection reveals striking commonalities in the peptide binding chemistry by the TCR, in particular a requirement for a hydrophobic contact at the apex of the P7 'bulge' that forms the principal site of contact with the TCR CDR3β. In contrast, a second class I TCR, 2C, was not found to be cross-reactive, instead exhibiting specificity for its endogenous antigen, QL9, in a manner similar to the class II specific TCRs studied here.

An important implication of these findings is that identification of endogenous antigens of TCRs is feasible using peptide-MHC libraries. In our previous view of cross-reactivity, we assumed that a given TCR would cross-react with so many peptides in a library that elucidation of 'natural' leads from a background of degenerately binding sequences would be extremely difficult. Yet we find that we recover essentially only peptides with clear linkages to the natural ligands. The sparse coverage of possible sequences renders it unlikely that any given sequence of interest will be represented with 100% identity in our library.

However, using selection results to constrain computational searches of protein databases proved to be a highly successful strategy, with 94% of peptides that were predicted to bind showing activity with the TCR of interest. Thus, this approach now opens up peptide ligand discovery for 'orphan' TCRs, such as those from regulatory T cells and tumor infiltrating lymphocytes (TILs).

While the naturally occurring peptides in this study were found as a proof of principle for our methodology, they demonstrate that autoimmune T cells have the ability to be activated by immunogens encountered in the environment, which may serve as the triggers for the initiation of autoimmunity. Several of the peptides in our panel are derived from microorganisms such as *Legionella longbeachae* and *Acinetobacter* that have previously been shown to be pathogenic in humans, and thus may have a role in the pathogenesis of multiple sclerosis. Furthermore, a number of other peptides from human pathogens were previously shown to activate human MBP-specific T cell clones. Additionally, the potential for other human peptides to cross-react with autoimmune TCRs with previously 'known' antigens presents the intriguing possibility that individual TCRs can recognize multiple self-peptides, potentially contributing to T cell pathologies in autoimmune disease. This notion is supported by the finding that a murine TCR specific for myelin-oligodendrocyte glycoprotein cross-reacts with a second CNS antigen, neurofilament M. Due to this unexpected crossreactivity, these T cells remained pathogenic even in MOG-deficient mice. Our approach for systematic discovery of peptides recognized by human TCRs thus can advance our understanding of complex pathogenesis of immune-mediated diseases.

Methods

Creation and staining of yeast display constructs I-Ek and HLA-DR15 constructs were codon optimized for yeast expression and synthesized as N-terminal fusions to the yeast surface protein Aga2p (Genscript). Constructs were cloned into the vector pYAL, which contains a Gly-Ser linker and either Myc or Flag epitope tag between the MHC and Aga2p and the Aga2p leader sequence. MHC α1 and β1 boundaries were determined by examination of previously published structures (PDB 3QIB and 1YMM) and appropriate MHC linker lengths were determined via modeling in Coot. For both constructs, MHC β chain residues 3-96 were used, followed by an eight amino acid Gly-Ser linker, followed by MHC α chain residues 1-83. The peptide was linked to the N terminus of the MHC construct via a 12 amino acid linker. MHC constructs were then electroporated into EBY-100 yeast as previously described (Adams et al., 2011, supra), and induced for expression in SGCAA pH 4.5 media at 20° for 24-60 hours until maximum epitope tag staining was observed (typically 40-70% of total population). To stain pMHC with TCR tetramers, biotinylated TCR was incubated with streptavidin coupled to AlexaFluor 647 (created as described in Ramachandiran et al. (2007). J Immunol Methods 319, 13-20) in a 5:1 ratio for 5 minutes on ice to ensure complete tetramer formation. Yeast cells were then stained with 500 nM tetramer+anti-Myc-alexa fluor 488 or anti-DYKDDDDK-alexa fluor 488 antibodies (Cell Signaling #2279 or #5407, respectively) for 3 hours on ice and washed twice with ice cold PBS+0.5% BSA and 1 mM EDTA (PBE buffer) before analysis via flow cytometry (Accuri C6 flow cytometer).

Library creation of 'mini' I-Ek and HLA-DR15 'mini' MHC constructs were mutagenized via error prone PCR (Genemorph II kit, Agilent 200550), with a final error rate of ~3-4 nucleotide substitutions per construct as judged by ligating error prone constructs into a vector and sequencing several clones. Yeast libraries were created by electroporation of competent EBY-100 cells via homologous recombination of linearized pYAL vector and mutagenized pMHC construct essentially as described previously. Final libraries contained approximately 2×10$^8$ yeast transformants. Peptide libraries were created in the same manner as the error prone libraries, except pMHC constructs were instead randomized along the peptide by using mutagenic primers allowing all 20 amino acids via an NNK codon as previously described. The libraries allowed only limited diversity at the known MHC anchor residues to maximize the number of correctly folded and displayed pMHC clones in the library. For I-Ek, P1 and P9 anchors were limited to (ILV) and K using VTT and AAA codons, respectively. P(−2) and P10 were limited to ADNT and AEGKRT using RMA and RVA codons, respectively. For HLA-DR15, P1 and P4 anchors were limited to ILV and FY using VTA and TWT codons, respectively. For the HFK-suppressed DR-15 library, His was suppressed at P2 by using a combination of DNK and NBK codons; Phe was suppressed at P3 by using VNK+NVK; Lys was suppressed at P5 by using BNK+NBK, for a total of 8 primers to construct the library. The resulting PCR product was used as template for a second PCR reaction in which 50 nt of sequence homologous to the vector was added to both ends of the PCR product. ~100 ug of PCR product and ~20 ug linearized vector were purified and used for the creation of each library.

List of primers for error prone libraries:

```
F (gal promoter f):
5'-ATGCAAAAACTGCATAACCAC-3'

R (pyal_rev):
5'-GGGATTTGCTCGCATATAGTTG-3'

For the random I-Ek library:
F primer (initial randomization PCR):
5'-TATTGCTAGCGTTTTAGCAGCTRMTNNKVT

TNNKNNKNNKNNKNNKNNKNNKAAARVAGGCGG

TGGTTCGGGCGGTG-3'

R primer (initial randomization PCR):
5'-CGTCATCATCTTTATAATCGGATC-3'

To add overlap for homologous
recombination with linearized pYAL vector:
F primer:
5'-TTCAATTAAGATGCAGTTACTTCGCTGTT

TTTCAATATTTTCTGTTATTGCTAGCGTTTTA

GCAGCT-3'

R primer: 5'-ACCACCAGATCCACCACCACC
TTTATCGTCATCATCTTTATAATCGGATC-3'
For the random HLA-DR15 library:
F primer (initial randomization PCR):
5'-GTTATTGCTAGCGTATTGGCCNNKNNKNNKN

NKVTANNKNNKTWTNNKNNKNNKNNKNNKNNKAG

AGGTGGTGGTGGTTCAGGT-3'

F primer (to add homologous
recombination region):
5'-TTCAATTAAGATGCAGTTACTTCGCTGTTTT

TCAATATTTTCTGTTATTGCTAGCGTATTGGCC-3'

R primer (used for both PCRs):
5'-ACCGCCACCACCAGATCCACCACCACCCAAGT

CTTCTTCAGAAATAAGC TT-5'

For the 'HF' motif suppression library
F primers (all other primers identical
to main HLADR15 library, with eight PCR
products pooled to serve as second PCR
template):
5'-GTTATTGCTAGCGTATTGGCCNNKNNKNNKNN

KVTADNKVNKTWTBNKNNKNNKNNKNNKNNKAGAG

GTGGTGGTGGTTCAGGT-3'

5'-GTTATTGCTAGCGTATTGGCCNNKNNKNNKNN

KVTADNKVNKTWTNBKNNKNNKNNKNNKNNKAGAG

GTGGTGGTGGTTCAGGT-3'

5'-GTTATTGCTAGCGTATTGGCCNNKNNKNNKNN

KVTADNKNVKTWTBNKNNKNNKNNKNNKNNKAGAG

GTGGTGGTGGTTCAGGT-3'

5'-GTTATTGCTAGCGTATTGGCCNNKNNKNNKNN

KVTADNKNVKTWTNBKNNKNNKNNKNNKNNKAGAG

GTGGTGGTGGTTCAGGT-3'

5'-GTTATTGCTAGCGTATTGGCCNNKNNKNNKNN

KVTANBKVNKTWTBNKNNKNNKNNKNNKNNKAGAG

GTGGTGGTGGTTCAGGT-3'

5'-GTTATTGCTAGCGTATTGGCCNNKNNKNNKNN

KVTANBKVNKTWTNBKNNKNNKNNKNNKNNKAGAG

GTGGTGGTGGTTCAGGT-3'

5'-GTTATTGCTAGCGTATTGGCCNNKNNKNNKNN

KVTANBKNVKTWTBNKNNKNNKNNKNNKNNKAGAG

GTGGTGGTGGTTCAGGT-3'

5'-GTTATTGCTAGCGTATTGGCCNNKNNKNNKNN

KVTANBKNVKTWTNBKNNKNNKNNKNNKNNKAGAG

GTGGTGGTGGTTCAGGT-3'

For the 'HF' motif optimization library
F primer (all other primers identical
to main HLADR15 library):
5'-GTTATTGCTAGCGTATTGGCCNNKNNKNNKNN

KRTACATTTCTTTARANNKNNKNNKNNKNNKAGAG

GTGGTGGTGGTTCAGGT-3'
```

Selection of pMHC libraries To maximize sensitivity of selections, all described selection steps were conducted at 4° using cold buffers, and refrigerated centrifuges. All spins were 5,000×g for 1 minute. Before each round of selection, a small sample of yeast (~1×10$^6$ cells) were stained with an anti-epitope tag antibody. For the first round of selection, ~2×10$^9$ yeast were washed once with PBS+0.5% BSA and 1 mM EDTA (PBE buffer) and then cleared with unloaded Streptavidin Microbeads (250 uL beads in 5 mL PBE) (Miltenyi, 130-048-101) to eliminate any nonspecifically binding yeast clones by incubating 1 hr at 4° with gentle rotation. The yeast were then spun down, resuspended in 5 mL PBE without a wash, and passed through a Miltenyi LS column. Yeast that did not bind to streptavidin alone were then spun down, resuspended in 5 mL PBE, and incubated with Streptavidin Microbeads loaded with TCR (400 nM TCR were added to 250 uL beads, an amount empirically determined to saturate the streptavidin beads) for 3-4 hrs at 4° with gentle rotation. TCR-binding yeast were then selected via an LS column, washed in SDCAA, and then re-cultured in SDCAA, pH 4.5 at 30° C. overnight. Yeast were re-induced upon reaching OD>2. For each round of selection, at least 10-fold more yeast was used than recovered from the previous round to ensure complete coverage of all selected yeast. Second and third rounds of selection were conducted in the same manner, but with reduced volumes (50 □L of beads in 500 LL PBE). Progress of selections was monitored by counting of cells selected to TCR-bound streptavidin beads as compared to streptavidin beads alone via an Accuri C6 flow cytometer. Selections typically showed enrichment for TCR binding after 3-4 rounds. For the final round of selection (conducted when the yeast count enriched by TCR loaded beads was higher than background, usually after 3 rounds), the libraries were stained with 500 nM streptavidin-TCR tetramer as described above, washed 3× with PBE, then incubated with 50 uL anti-Alexa647 Microbeads (Miltenyi, 130-091-395) in 450 □L PBE for 20 minutes. The yeast were washed a final time and passed through a Miltenyi LS column. Enriched yeast were then plated on SDCAA plates for characterization of individual colonies. Individual yeast clones were then screened for tetramer staining as described above. Plasmids containing the selected pMHC were isolated from positive clones via yeast miniprep (Zymoprep II kit, Zymo Research) and sequenced (Sequetech).

Deep sequencing of selection libraries. Pooled plasmids from 5×10$^7$ yeast from each round of selection were isolated via yeast miniprep (Zymoprep II kit, Zymo Research) and used as PCR template to prepare Illumina samples. Amplicon libraries were designed as follows: (Illumina P5-Truseq read 1-(N8)-Barcode-pMHC-(N8)-Truseq read 2-IlluminaP7). N8 was added immediately after both sequencing primers to generate diversity for low complexity sequencing reads. The adapter and barcode sequences were appended via nested 25-round cycles of PCR of the purified plasmids using Phusion polymerase (NEB). Primers were proximal to the peptide on the pMHC, annealing to the Aga2p leader sequence (5' end) and MHC β1 domain (3' end) to ensure high quality sequence reads of the peptide with double coverage. Final PCR products were run on a high percentage agarose gel and purified via gel extraction. PCR products were then quantitated via nanodrop, normalized for each barcoded round of selection to be equally represented, doped with 5-50% PhiX DNA to ensure sufficient sequence diversity for high quality sequence reads, and run on an Illumina MiSeq with 2×150 nt Paired End reads. The initial deep sequencing run, for the 2B4-I-E$^k$ selections, was conducted with 1×150 nt Single End reads. When the sequencing data was analyzed as described below, we saw no significant difference in data quality between single and paired-end reads (as judged by comparing the results for 226/5cc7 when analyzed as single reads vs. paired-end reads). Deep sequencing was conducted at the Stanford Stem Cell Institute Genome Center.

To analyze the sequence data, contigs were generated for each paired end read using PandaSeq. The contigs were then deconvoluted into individual rounds of selections and trimmed to the peptide sequence using Geneious version 6. The number of reads for each unique sequence were then summed and corrected for any potential PCR or sequence read errors by coalescing any sequences differing from only 1 nucleotide from the most dominant representative sequence. Sequences were then translated into peptides, and any reads that contained stop codons or frameshifts were omitted from further analysis. Amino acid frequencies and coevolution analyses were then calculated using scripts and visualized with Matlab (Mathworks Inc.) as previously described.

List of primers used for deep sequencing. The first PCR was conducted with primers specific to the MHC construct that added N8 sequence for read diversity and a 6-nucleotide barcode. The second PCR was conducted with general primers to add the necessarily Illumina adaptor sequences.

```
           I-E^k F primer:
 5'-CTA CAC GAC GCT CTT CCG ATC TNN NNN NNN
   XXX XXX CTG TTA TTG CTA GCG TTT TAG CA-3'
           I-E^k R primer:
 5'-GCT GAA CCG CTC TTC CGA TCT NNN NNN NNA
     ACT CTT TGA GTA CCA TTA TAG AAA-3'
          HLA-DR15 F primer:
 5'-CTA CAC GAC GCT CTT CCG ATC TNN NNN NNN
   XXX XXX CTG TTA TTG CTA GCG TAT TGG CC-3'
          HLA-DR15 R primer:
 5'-GCT GAA CCG CTC TTC CGA TCT NNN NNN NNC
        GTT GAA AAA GTG ACA TTC TC-3'
   Illumina F: 5'-AAT GAT ACG GCG ACC ACC GAG
     ATC TAC ACT CTT TCC CTA CAC GAC GCT CTT
                    CCG ATC T-3'
   Illumina R: 5'-CAA GCA GAA GAC GGC ATA CGA
    GAT CGG TCT CGG CAT TCC TGC TGA ACC GCT CTT
                    CCG ATC -3',
      Where XXX XXX represents the following
                      barcodes:
```

| I-E$^k$ round | DNA barcode | HLA-DR15 Round | DMA barcode |
|---|---|---|---|
| I-E$^k$ pre-selection lib | ATCACG | HLA-DR15 random lib pre-selection | GTGGCC |
| 2B4 rd1 | CGATGT | Random lib Ob.1A12 rd1 | GTTTCG |
| 2B4 rd2 | TTAGGC | Random lib Ob.1A12 rd2 | CGTACG |
| 2B4 rd3 | TGACCA | Random lib Ob.1A12 rd3 | GAGTGG |
| 2B4 rd4 | ACAGTG | Random lib Ob.1A12 rd4 | GGTAGC |
| I-E$^k$ pre-selection lib | GGCTAC | Random lib Ob.2F3 rd1 | ATGAGC |
| 5cc7 rd1 | CTTGTA | Random lib Ob.2F3 rd2 | ATTCCT |
| 5cc7 rd2 | AGTGAA | Random lib Ob.2F3 rd3 | CAAAAG |
| 5cc7 rd3 | AGTTCC | Random lib Ob.2F3 rd4 | GAACTA |
| 5cc7 rd4 | ATGTCA | HLA-DR15 HF-suppressed lib pre-selection | CACGAT |

-continued

```
            I-E^k F primer:
5'-CTA CAC GAC GCT CTT CCG ATC TNN NNN NNN
    XXX XXX CTG TTA TTG CTA GCG TTT TAG CA-3'
            I-E^k R primer:
5'-GCT GAA CCG CTC TTC CGA TCT NNN NNN NNA
    ACT CTT TGA GTA CCA TTA TAG AAA-3'
            HLA-DR15 F primer:
5'-CTA CAC GAC GCT CTT CCG ATC TNN NNN NNN
    XXX XXX CTG TTA TTG CTA GCG TAT TGG CC-3'
            HLA-DR15 R primer:
5'-GCT GAA CCG CTC TTC CGA TCT NNN NNN NNC
    GTT GAA AAA GTG ACA TTC TC-3'
Illumina F: 5'-AAT GAT ACG GCG ACC ACC GAG
    ATC TAC ACT CTT TCC CTA CAC GAC GCT CTT
                CCG ATC T-3'
Illumina R: 5'-CAA GCA GAA GAC GGC ATA CGA
    GAT CGG TCT CGG CAT TCC TGC TGA ACC GCT CTT
                CCG ATC -3',
    Where XXX XXX represents the following
                barcodes:
```

| I-E^k round | DNA barcode | HLA-DR15 Round | DMA barcode |
|---|---|---|---|
| 226 rd1 | CCGTCC | HF suppressed Ob.1A12 rd1 | CACTCA |
| 226 rd2 | GTAGAG | HF suppressed Ob.1A12 rd2 | CAGGCG |
| 226 rd3 | GTCCGC | HF suppressed Ob.1A12 rd3 | CATGGC |
| 226 rd4 | GTGAAA | HF suppressed Ob.1A12 rd4 | CATTTT |
| | | HF suppressed Ob.2F3 rd1 | CGGAAT |
| | | HF suppressed Ob.2F3 rd2 | CTAGCT |
| | | HF suppressed Ob.2F3 rd3 | CTATAC |
| | | HF suppressed Ob.2F3 rd4 | CTCAGA |
| | | HLA-DR 15 HF-motif lib pre-selection | TACAGC |
| | | HF motif Ob.1A12 rd1 | TATAAT |
| | | HF motif Ob.1A12 rd2 | TCATTC |
| | | HF motif Ob.1A12 rd3 | TCCCGA |
| | | HF motif Ob.2F3 rd1 | TCGAAG |
| | | HF motif Ob.2F3 rd2 | TCGGCA |
| | | HF motif Ob.2F3 rd3 | AAACAC |

Clustering of selected peptide sequences. To quantify peptide convergence, a random sampling of 1000 pre-enriched library sequences were compared to the top 1000 most enriched sequences from each of the post-TCR selection library sequences. For each set, dispersion was quantified as the minimum hamming distance from each sequence to the next closest non-identical sequence within the set. While in the preselected library the mean minimum distance was 5 amino acids and no identical or distance 1 amino acid sequences were observed, in each of the selected libraries the majority of sequences were significantly more similar to one another than observed pre-selection, with a significant enrichment of distance 1 ($p<0.001$), distance 2 ($p<0.001$) and distance 3 ($p<0.001$) sequences emerging after selection, as determined by both Chi-squared and permutation sampling studies from the preselected library. To distinguish whether TCR selection resulted in a single convergent peptide solution or multiple independent solutions, for each TCR selection all sequences enriched to a frequency above the highest frequency for any clone in the background library were combined and connected by hamming distance into a network using the maximum mutation distance parameter 1, 2, 3, or 4 as obtained from initial sampling. The networks established that all sequences from all three TCRs generate a single dominant graph in which the true ligand was also connected (although never explicitly discovered), while no unselected library sequences converged into the network.

Profile-based searches for naturally occurring peptide ligands based upon selection results. The positional frequencies from the round 3 fixed HF library were used to generate a 14×20 matrix. The positional frequencies for the P1 and P4 anchors from the most abundant unique sequences from the selected fully random library was used instead of the fixed HF library frequencies to increase diversity of sequences in the search at the respective positions. A cutoff of amino acid frequencies less than 0.01 was used and frequencies below the cutoff were set to zero. The NCBI NR database and Human proteome from Uniprot were both downloaded from the respective servers. Both the NR and human databases were searched with the custom algorithm by using a 14-position sliding window alignment with scoring the product of positional amino acid frequencies from the substitution matrix (Cockcroft and Osguthorpe (1991) FEBS letters 293, 149-152; De la Herran-Arita et al. (2013) Science translational medicine 5, 216ra176). An aligned segment containing at least one amino acid where the frequency was below the 0.01 frequency cutoff was excluded as a match regardless of the abundance at other positions. Since the search found thousands of possible unique 14 amino acid peptide matches and the success rate for the functional activation potential of the predicted peptides was unknown, we aligned each of the fixed-HF library peptides with >20 reads to each of the peptide database hits. 26 NR hits and library comparators hits plus 8 human peptide hits (including the WT peptide, MBP) were chosen for functional validation. The peptides were chosen to have diverse statistics such as pairwise identity between search hit and library comparator sequence, search score, counts of the library comparator peptides, and diversity of sequence identity. Broad diversity of statistics was considered to sample the parameters for the hundreds of predicted peptides, the logic was to later use this information to improve our predictions. However, due to the high prediction rate, 94%, no correlations could be made.

Protein expression of pMHC and TCR for selection, affinity measurements, and structure determination. Proteins for this study were created in multiple formats, described below and separated by use.

2B4, 226, and 5cc7 TCR for selection. TCR VmCh chimeras containing an engineered C domain disulfide were cloned into the pAcGP67a insect expression vector (BD Biosciences, 554756) encoding either a C-terminal acidic GCN4-zipper-Biotin acceptor peptide (BAP)-6×His tag (for α chain) or a C-terminal basic GCN4 zipper-6×His tag (for β chain). Each chain also encoded a 3C protease site between the C-terminus of the TCR ectodomains and the GCN4 zippers to allow for cleavage of zippers. Baculoviruses for each TCR construct were created in SF9 cells via contransfection of BD baculogold linearized baculovirus DNA (BD Biosciences 554739) with Cellfectin II (Life Technologies 10362-100). TCRα and β chain viruses were coinfected in a small volume (2 mL) of High Five cells in various ratios to find a ratio to ensure 1:1 α:β stoichiometry.

To prepare TCRs, 1 L of High Five cells were infected with the appropriate ratio of TCRα and TCRβ viruses for 48 hrs at 28°. Collected culture media was conditioned with 100 mM Tris-HCl pH8.0, 1 mM NiCl2, 5 mM CaCl2 and the subsequent precipitation was cleared via centrifugation. The media is then incubated with Ni-NTA resin (Qiagen 30250) at RT for 3 hours and eluted in 1×HBS+200 mM imidazole pH 7.2. TCRs were then site-specifically biotinylated by adding recombinant BirA ligase, 100 μM biotin, 50 mM Bicine pH 8.3, 10 mM ATP, and 10 mM Magnesium Acetate and incubating 4° O/N. The reaction was then purified via size exclusion chromatography using an AKTAPurifier (GE Healthcare) on a Superdex 200 column (GE Healthcare). Peak fractions were pooled and then tested for biotinylation using an SDS-PAGE gel shift assay. Proteins were typically 100% biotinylated.

Insect-expressed 2B4 TCR for crystallography. 2B4 TCR was created as described above, except instead of biotinylation, protein was incubated with recombinant 3C protease (10 μg/mg of TCR) and carboxypeptidase A at 4° overnight. Insect-expressed I-E$^k$ MHC I-Ek was cloned into pAcGP67A with acidic/basic zippers as described for TCRs. The I-E$^k$β construct was modified with an N-terminal extension containing either the 2A peptide via a Gly-Ser linker or CLIP peptide via a Gly-Ser linker containing a thrombin cleavage site.

Expression, biotinylation, and purification of protein were as described for insect-expressed TCRs, with the exception of 72 hours of protein expression. For crystallography, I-Ek was treated with recombinant 3C protease (10 μg/mg of MHC) and carboxypeptidase A and incubated at 4° overnight before size exclusion chromatography.

Refolded Murine TCRs for crystallography and affinity measurements. Refolded 2B4, 226, and 5cc7 were created essentially as described. For 50 and 5c2 crystal structures, the 5c1 and 5c2 peptides were fused to the N-terminus of 5cc7β via a 10-amino acid GlySer linker. TCRs were purified via size exclusion chromatography and assayed via SDS-PAGE to ensure 1:1 α:β stoichiometry. If there were an excess of TCRβ, ββ homodimer was purified away from αβ heterodimer via ion exchange chromatography on a MonoQ column (GE Healthcare) using a 20 mM Tris pH 8/20 mM Tris pH8+ 500 mM NaCl buffer system. Proteins were then reexchanged into HBS for further use.

Refolding and biotinylation of Ob.1A12 and Ob.2F3 TCRs. The α and β chains of Ob.1A12 and Ob.2F3 TCRs were separately cloned into the pET-22b vector (Novagen) and expressed as inclusion bodies in BL21(DE3)*Escherichia coli* cells (Novagen). The inclusion bodies were purified and dissolved in 6 M guanidine hydrochloride, 10 mM dithiothreitol and 10 mM EDTA. To initiate refolding, solubilized TCR α and β chains were mixed at a 1:1 molar ratio and diluted to a final concentration of 25 μg/ml of each chain in a refolding buffer containing 5 M urea, 0.5 M L-arginine-HCl, 100 mM Tris-HCl, pH 8.2, 1 mM GSH and 0.1 mM GSSH. After 40 h at 4° C., the refolding mixture was dialyzed twice against deionized water and twice against 10 mM Tris-HCl, pH 8.0. Refolded TCR was purified by anion exchange chromatography using Poros PI (Applied Biosystems) and MonoQ (GE Healthcare) columns. Two cysteines that form the interchain disulfide bond of the Cα and Cβ Ig domains were repositioned from the C-terminal to the N-terminal part of these domains (via replacement of Cα Thr48 and Cβ Ser57 with cysteines) in order to enhance refolding of TCR heterodimer (Boulter et al., 2003). In the expression construct, a BirA tag was placed at the C-terminal of the TCR β chain. Site-specific biotinylation of the BirA tag was carried out at a protein concentration of 2 mg/ml at a molar ratio of 20:1 (TCR to BirA). Reactions were incubated for 2 h at 30° C. in the presence of 100 μM biotin, 10 mM ATP, 10 mM magnesium acetate and protease inhibitors, followed by extensive dialysis to remove excess biotin. Biotinylation was confirmed by mobility shift with streptavidin using native polyacrylamide gels.

Selection of library derived I-Ek peptides for further characterization. Peptides were chosen from the deep sequencing data across a wide range of sequence prevalence for further study via SPR, activity, and structural characterization. Peptides were chosen that were recognized by 1, 2, or all 3 I-E$^k$ reactive TCRs. All peptides were tested for activity with both 2B4 and 5cc7 T cell clones regardless of for which TCR they were initially selected. A subset of peptides was chosen to further characterize via SPR. The 2A peptide that was structurally characterized in FIG. 5A was discovered by manual curation of an I-Ek peptide library. 2A is highly homologous to peptides represented in the deep sequencing data and co-clusters with MCC.

Surface plasmon resonance. Affinity measurements for peptides bound to I-Ek for 226, 2B4, and 5cc7 TCRs were determined via surface plasmon resonance on a Biacore T100 (GE Healthcare). 10 μM of peptide of interest was added to biotinylated Clip-I-Ek. 1 U thrombin/100 μg MHC was added and incubated at 37°. After 1 hour, pH was lowered by adding sodium cacodylate pH 6.2 to 30 mM and sample was incubated at 37° overnight. Samples were then neutralized with 40 mM HEPES pH 7.2 and stored at 4° until use. pMHC exchanged with the peptide of interest were bound to a Biacore SA chip (GE Healthcare) at a low surface density (100-200 RU) to ensure no recapture of analyte. I-Ek exchanged with a null peptide (MCC K99E) was used as the reference surface. SPR runs were conducted in HBSP+ with 0.1% BSA to reduce nonspecific binding of TCR to the dextran surface. All measurements were made with 3-fold serial dilutions of refolded TCR using 60 s association followed by a 600 s dissociation at 10-30 μL/min flow rate. No regeneration was required because samples returned completely to baseline during dissociation. Measurement of titrations at equilibrium was used to determine KD.

Activity assay for I-Ek-selected peptides. Lymphocytes were isolated from 5cc7 or 2B4 TCR transgenic Rag−/− mice. All cells were maintained in RPMI+10% FBS, 2 mM L-glutamine, 1 mM sodium pyruvate, 1× MEM-NEAA, pen-strep, and 50 μM 2-mercaptoethanol. Antigen specific T cells were stimulated to form blasts with 10 μM MCC added to cells at 1×10$^7$ cells/mL, with 30 U/mL recombinant IL-2 (R&D Systems) added on day 0 and day 1, splitting on subsequent days as necessary. T cell blasts were used between day 6 and day 10 post-stimulation and isolated with Histopaque 1119 (Sigma) before use to ensure live lymphocytes. T cells were placed into fresh media for 6 hours pre-stimulation to ensure cells were at rest before introduction of peptides of interest. Peptides from library plus positive (MCC) and negative (MCC K99E) controls were synthesized via solid phase peptide synthesis (Genscript) and dissolved at 20 mM in DMSO. 1×10$^5$ CH27 cells (an APC line that expresses I-E$^k$) per titration point were incubated with peptide diluted in RPMI (Invitrogen) at 37° for 8 hours in a 96 well plate to allow peptide loading. 5×10$^4$ T cell blasts were then added to each well and the plate was briefly pulsed in a swinging bucket centrifuge to ensure good T cell-APC contact. The T cells were stimulated for 18 hours at 37°+5% CO2 in an incubator. After stimulation, cells were pelleted (300×g 5 minutes). The conditioned media was collected and frozen to measure IL-2 release and the cells were used to measure CD69 upregulation. To measure CD69 upregulation, T cells were stained with anti CD69-PE (clone H1.2F3, eBioscience 12-0691) and anti CD4-APC (clone GK1.5, eBioscience 17-0041) for 20 minutes at 40 Cells were then washed in PBS+0.5% BSA and fixed with 1.6% paraformaldehyde in PBS for 15 minutes at room temperature, and washed one final time before analysis. CD69 upregulation was measured using an Accuri C6 flow cytometer with an autosampler (BD) by measuring CD69 MFI in the CD4+ gate. Data was then normalized and EC50s measured via Prism. IL-2 release was measured in technical triplicates via anti-IL-2 Elisa (Ready-setgo mouse IL-2 ELISA kit, eBioscience 88-7024), as recommended by the manufacturer. Media was diluted 1:50 in buffer to obtain measurement within dynamic range of ELISA. Absorbance was measured via SpectraMax Paradigm (Molecular Devices), with EC50 determined via Graphpad Prism.

T cell Proliferation assays Ob.1A12 and Ob.2F3 T cell clones were restimulated with PHA-L (Roche) in the presence of irradiated peripheral blood mononuclear cells and cultured in RPMI 1640 supplemented with 10% FBS, 2 mM GlutaMAX-I, 10 mM Hepes (all Invitrogen), 1% human serum (Valley Biochemical), and 5 U/ml rIL-2 (Roche), as previously described (Wucherpfennig et al., 1994). T cells were used between 10 and 14 days after restimulation. To determine proliferation, 50×10$^3$ Ob.1A12 or Ob.2F3 T cells were cocultured in a 1:1 ratio with irradiated EBV-transformed MGAR cells that had been treated with 50 µg/ml mitomycin C for 30 min at 37° C. Cells were plated in 0.2 ml/well of a 96-well round bottom plate in AIM-V media (Invitrogen) supplemented with 2 mM GlutaMAX-I. Peptides were tested over a range of concentrations (in triplicates) and proliferation was assessed by [$^3$H]-thymidine incorporation after 72 h of culture.

Crystallization and X-ray data collection of I-Ek-TCR complexes. For the 2A-I-E$^k$-2B4 complex, 2B4 and 2A-I-E$^k$ were expressed and purified separately, as described above, and then mixed at a 1:1 ratio and concentrated to 14 mg/ml. Crystals formed in 100 nl sitting drops in 20 mM sodium/potassium phosphate, 0.1 M Bis-Tris propane pH8.5, 20% PEG-3350. For the 5c1/5c2-I-E$^k$-5cc7 complexes, tethered pMHC-TCR complexes were produced essentially as described in Newell et al, 2011. Briefly, purified CLIP-I-E$^k$ and 5cc7 with peptide tethered to the N-terminus of TCRβ were mixed at a 1:3 ratio and concentrated to 4 mg/mL. 1 U thrombin per 100 □g CLIP-I-E$^k$, and carboxypeptidases A and B were incubated with this sample for 3 hours at room temperature (RT). Sodium cacodylate, pH 6.2 was added to a final concentration of 30 mM and incubated at RT for 24-48 hours. Complex was isolated via size exclusion chromatography and concentrated to 10-15 mg/ml. Crystals formed in 100 nl-sitting drops in 0.2 M potassium citrate, 18% PEG-3350. Crystals used to collect datasets included either 4% 1,3 butanediol (for 5c1) or 4% Tert-butanol (for 5c2). All crystals were flash frozen in liquid nitrogen in mother liquor+30% ethylene glycol, and datasets were collected at Stanford Synchrotron Radiation Lightsource (Stanford, CA) beamlines 11-1 and 12-2. Data were indexed, integrated, and scaled using either XDS/XSCALE or the HKL-2000 program suite.

Structure determination and refinement. All structures were solved via molecular replacement using the program Phaser. The molecular replacement search model for the TCRs was the unliganded 2B4 or 5cc7 TCR (PDB ID 3QJF and 3QJH), with the CDR3 loops deleted to avoid model bias. The molecular replacement search model for MHC was the pMHC from the MCC-I-E$^k$-2B4 complex structure (PDB ID 3QIB) with the peptide deleted to avoid model bias. Manual model building of the peptide and CDR3 loops was performed in COOT followed by iterative rounds of refinement with Phenix, using NCS restraints for the 5cc7 complex structures. For the 5cc7 complex structures, the first complex copy in the asymmetric unit (chains A-E) was used for analysis. Figures were made with PYMOL.

TABLE 1

| | 2B4-2A-I-E$^k$ | 5cc7-5c1-I-E$^k$ | 5cc7-5c2-I-E$^k$ |
|---|---|---|---|
| Data Collection | | | |
| Space Group | C2 | C2 | C2 |
| Cell Dimensions | | | |
| a, b, c (Å) | 239.94, 60.18, 78.36 | 261.60, 101.87, 214.64 | 262.90, 102.21, 214.11 |
| α, β, γ (°) | 90, 104.33, 90 | 90, 94.88, 90 | 90, 95.04, 90 |
| Resolution (Å) | 50-2.60 | 39.81-3.29 | 39.63-3.30 |
| | (2.64-2.60) | (3.36-3.29) | (3.36-3.30) |
| R$_{sym}$ (%) | 9.3 (42.8) | 14.3 (135.6) | 17.7 (198.0) |
| <I/σ(I)> | 13.6 (2.0) | 10.9 (1.3) | 9.3 (1.0) |
| Completeness (%) | 96.8 (88.6) | 98.8 (84.9) | 99.3 (96.5) |
| Redundancy | 3.8 (2.8) | 6.8 (5.8) | 7.1 (6.7) |
| Refinement | | | |
| Resokition (Å) | 50-2.60 | 40-3.29 | 40-3.30 |
| | (2.68-2.60) | (3.33-3.29) | (3.34-3.30) |
| Reflections | 32548 | 84239 | 84648 |
| R$_{cryst}$ (%) | 18.87 (28.13) | 21.07 (35.82) | 18.81 (36.77) |
| R$_{free}$ (%) | 24.50 (36.43) | 24.10 (40.73) | 23.57 (40.12) |
| Number of atoms | | | |
| Protein | 6493 | 25581 | 25597 |
| Ligand | 90 | 70 | 70 |
| Water | 118 | 0 | 0 |
| Wilson B-factor | 47.84 | 99.48 | 102.14 |
| Average B-factors (Å$^2$) | | | |
| All | 57.10 | 119.20 | 124.70 |
| Protein | 57.26 | 119.20 | 124.70 |
| Solvent | 48.36 | — | — |
| R.m.s. deviations from ideality | | | |
| Bond Lengths (Å) | 0.003 | 0.008 | 0.005 |
| Bond Angles (°) | 0.695 | 0.831 | 0.888 |
| Ramachandran statistics | | | |
| Flavored (%) | 96.49 | 96.37 | 95.80 |
| Outliers (%) | 0 | 0 | 0 |
| Rotamer outliers (%) | 0.70 | 0.54 | 0.75 |
| Clashscore | 4.76 | 4.98 | 5.40 |
| PDB accession code | 4P2O | 4P2R | 4P2Q |

TABLE 2

| | | | | | Ob. 1A12 TCR | | | | | | | | | |
|---|---|---|---|---|---|---|---|---|---|---|---|---|---|---|
| Amino | | | | | Peptide Position | | | | | | | | | |
| Acid | −4 | −3 | −2 | −1 | 1 | 2 | 3 | 4 | 5 | 6 | 7 | 8 | 9 | 10 |
| A | 0.06 | 0.11 | 0.15 | 0.05 | 0 | 0 | 0 | 0 | 0 | 0.23 | 0.03 | 0.07 | 0.12 | 0.1 |
| C | 0.02 | 0.03 | 0.02 | 0.04 | 0 | 0 | 0 | 0 | 0 | 0 | 0.01 | 0.01 | 0.11 | 0.02 |
| D | 0.06 | 0.01 | 0 | 0 | 0 | 0 | 0 | 0 | 0 | 0.02 | 0 | 0.02 | 0 | 0.02 |
| E | 0.13 | 0.05 | 0 | 0 | 0 | 0 | 0 | 0 | 0 | 0 | 0.05 | 0.04 | 0 | 0.02 |
| F | 0.02 | 0.01 | 0 | 0 | 0.01 | 0 | 1 | 0.46 | 0 | 0 | 0.02 | 0 | 0 | 0.03 |
| G | 0.06 | 0.1 | 0.15 | 0 | 0 | 0 | 0 | 0 | 0 | 0.23 | 0.02 | 0.06 | 0.05 | 0.03 |
| H | 0.11 | 0.1 | 0.07 | 0.02 | 0 | 1 | 0 | 0 | 0 | 0 | 0.14 | 0.05 | 0 | 0.03 |
| I | 0.01 | 0.01 | 0 | 0 | 0.45 | 0 | 0 | 0.02 | 0 | 0 | 0.04 | 0.02 | 0.05 | 0.02 |
| K | 0.02 | 0.05 | 0.02 | 0.22 | 0 | 0 | 0 | 0 | 0.74 | 0 | 0.04 | 0 | 0 | 0.05 |
| L | 0.03 | 0.05 | 0 | 0 | 0.19 | 0 | 0 | 0.1 | 0 | 0 | 0.17 | 0.1 | 0.23 | 0.08 |
| M | 0.03 | 0.02 | 0 | 0.01 | 0.03 | 0 | 0 | 0.02 | 0 | 0.06 | 0.02 | 0.04 | 0.03 | 0.04 |
| N | 0.04 | 0.04 | 0.06 | 0.07 | 0 | 0 | 0 | 0 | 0 | 0.17 | 0.08 | 0.02 | 0 | 0.02 |
| P | 0 | 0.03 | 0.16 | 0 | 0 | 0 | 0 | 0 | 0 | 0 | 0.1 | 0.11 | 0 | 0.03 |
| Q | 0.07 | 0.06 | 0.09 | 0 | 0 | 0 | 0 | 0 | 0 | 0.04 | 0.07 | 0.05 | 0.01 | 0.03 |
| R | 0.07 | 0.12 | 0.11 | 0.25 | 0 | 0 | 0 | 0 | 0.26 | 0 | 0.08 | 0.12 | 0 | 0.16 |
| S | 0.11 | 0.08 | 0.14 | 0.08 | 0 | 0 | 0 | 0 | 0 | 0.17 | 0.04 | 0.09 | 0.04 | 0.09 |
| T | 0.06 | 0.07 | 0 | 0 | 0 | 0 | 0 | 0 | 0 | 0.06 | 0.02 | 0.06 | 0.04 | 0.05 |
| V | 0.03 | 0.04 | 0.02 | 0.24 | 0.29 | 0 | 0 | 0.02 | 0 | 0 | 0.04 | 0.07 | 0.28 | 0.1 |
| W | 0.02 | 0 | 0 | 0 | 0.01 | 0 | 0 | 0.08 | 0 | 0 | 0.05 | 0 | 0 | 0.05 |
| Y | 0.04 | 0.02 | 0 | 0 | 0.01 | 0 | 0 | 0.3 | 0 | 0 | 0.01 | 0.01 | 0 | 0.03 |
| | | | | | Ob.2F3 TCR | | | | | | | | | |
| A | 0.07 | 0.1 | 0.16 | 0.08 | 0 | 0 | 0 | 0 | 0 | 0.26 | 0.02 | 0.07 | 0.1 | 0.1 |
| C | 0.02 | 0.03 | 0.02 | 0.04 | 0 | 0 | 0 | 0 | 0 | 0.01 | 0.01 | 0.01 | 0.08 | 0.03 |
| D | 0.06 | 0.02 | 0 | 0 | 0 | 0 | 0 | 0 | 0 | 0.01 | 0.01 | 0.02 | 0 | 0.02 |
| E | 0.12 | 0.05 | 0 | 0 | 0 | 0 | 0 | 0 | 0 | 0 | 0.07 | 0.04 | 0 | 0.02 |
| F | 0.02 | 0.01 | 0 | 0 | 0.01 | 0 | 1 | 0.46 | 0 | 0 | 0.01 | 0.01 | 0 | 0.03 |
| G | 0.06 | 0.1 | 0.15 | 0 | 0 | 0 | 0 | 0 | 0 | 0.23 | 0.02 | 0.06 | 0.04 | 0.03 |
| H | 0.08 | 0.08 | 0.08 | 0.03 | 0 | 1 | 0 | 0 | 0 | 0 | 0.04 | 0.05 | 0.01 | 0.03 |
| I | 0.01 | 0.01 | 0 | 0.01 | 0.45 | 0 | 0 | 0.02 | 0 | 0 | 0.04 | 0.02 | 0.07 | 0.02 |
| K | 0.02 | 0.05 | 0.02 | 0.15 | 0 | 0 | 0 | 0 | 0.69 | 0 | 0.04 | 0 | 0 | 0.04 |
| L | 0.03 | 0.04 | 0.01 | 0 | 0.19 | 0 | 0 | 0.1 | 0 | 0 | 0.17 | 0.11 | 0.26 | 0.08 |
| M | 0.03 | 0.02 | 0.01 | 0.01 | 0.03 | 0 | 0 | 0.02 | 0 | 0.03 | 0.01 | 0.04 | 0.04 | 0.04 |
| N | 0.04 | 0.04 | 0.06 | 0.06 | 0 | 0 | 0 | 0 | 0 | 0.15 | 0.11 | 0.02 | 0.01 | 0.02 |
| P | 0 | 0.04 | 0.12 | 0 | 0 | 0 | 0 | 0 | 0 | 0 | 0.09 | 0.09 | 0 | 0.03 |
| Q | 0.08 | 0.07 | 0.07 | 0 | 0 | 0 | 0 | 0 | 0 | 0.03 | 0.13 | 0.05 | 0.02 | 0.03 |
| R | 0.07 | 0.13 | 0.12 | 0.21 | 0 | 0 | 0 | 0 | 0.31 | 0 | 0.12 | 0.12 | 0 | 0.13 |
| S | 0.11 | 0.08 | 0.15 | 0.11 | 0 | 0 | 0 | 0 | 0 | 0.16 | 0.03 | 0.09 | 0.03 | 0.1 |
| T | 0.06 | 0.07 | 0 | 0.01 | 0 | 0 | 0 | 0 | 0 | 0.05 | 0.05 | 0.06 | 0.04 | 0.06 |
| V | 0.04 | 0.04 | 0.02 | 0.26 | 0.29 | 0 | 0 | 0.02 | 0 | 0 | 0.04 | 0.07 | 0.3 | 0.11 |
| W | 0.02 | 0 | 0 | 0 | 0.01 | 0 | 0 | 0.08 | 0 | 0 | 0.01 | 0.01 | 0 | 0.05 |
| Y | 0.04 | 0.02 | 0 | 0.01 | 0.01 | 0 | 0 | 0.3 | 0 | 0 | 0.01 | 0.02 | 0 | 0.03 |

Example 2

Figure 16:
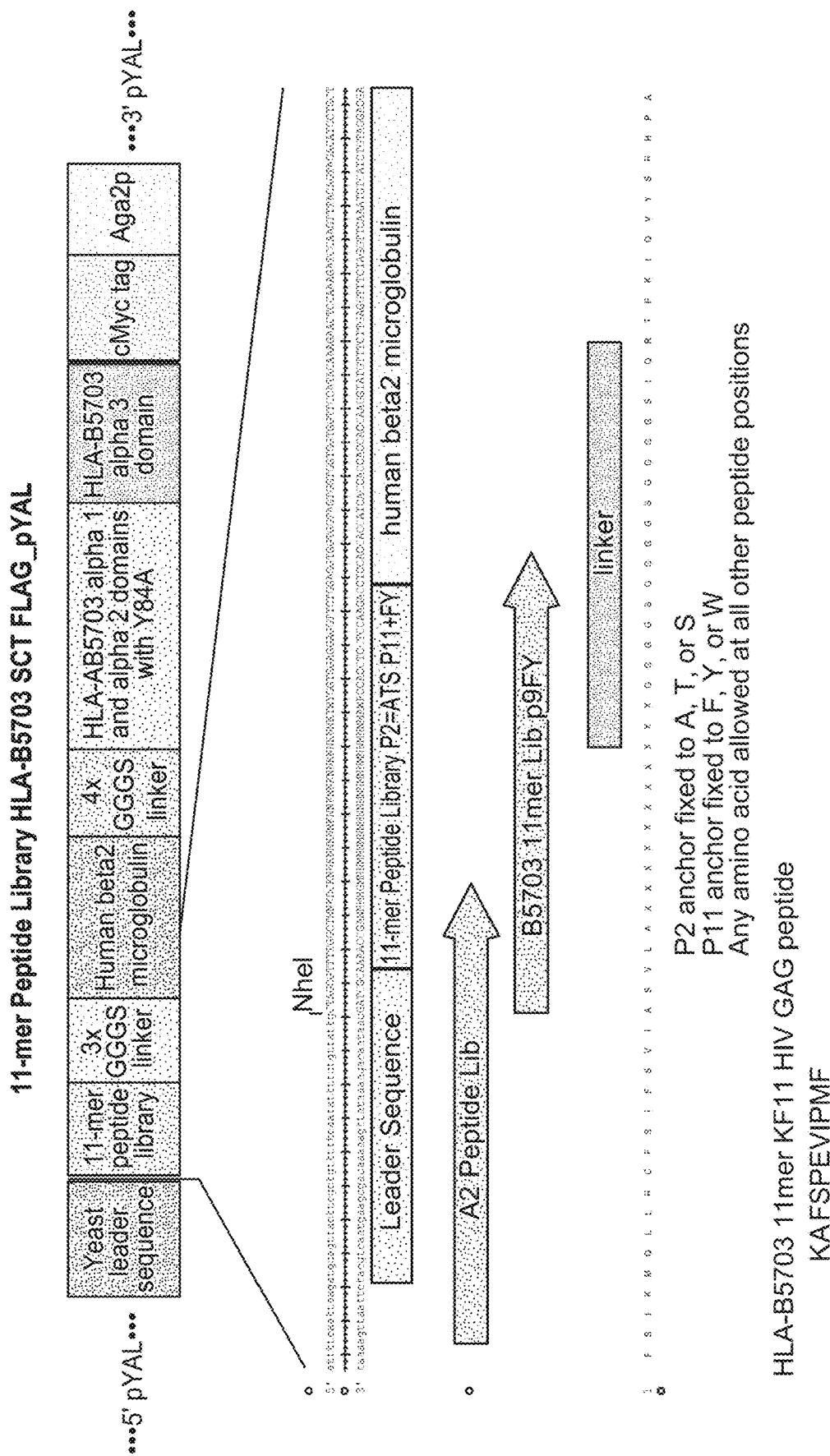
FIG. 16: Schematic of HLA-B5703 library and construct. The library was constructed with the P2 anchor of the peptide ligand fixed to A, T or S and the P11 anchor fixed to F, Y or W.
Figure 17:
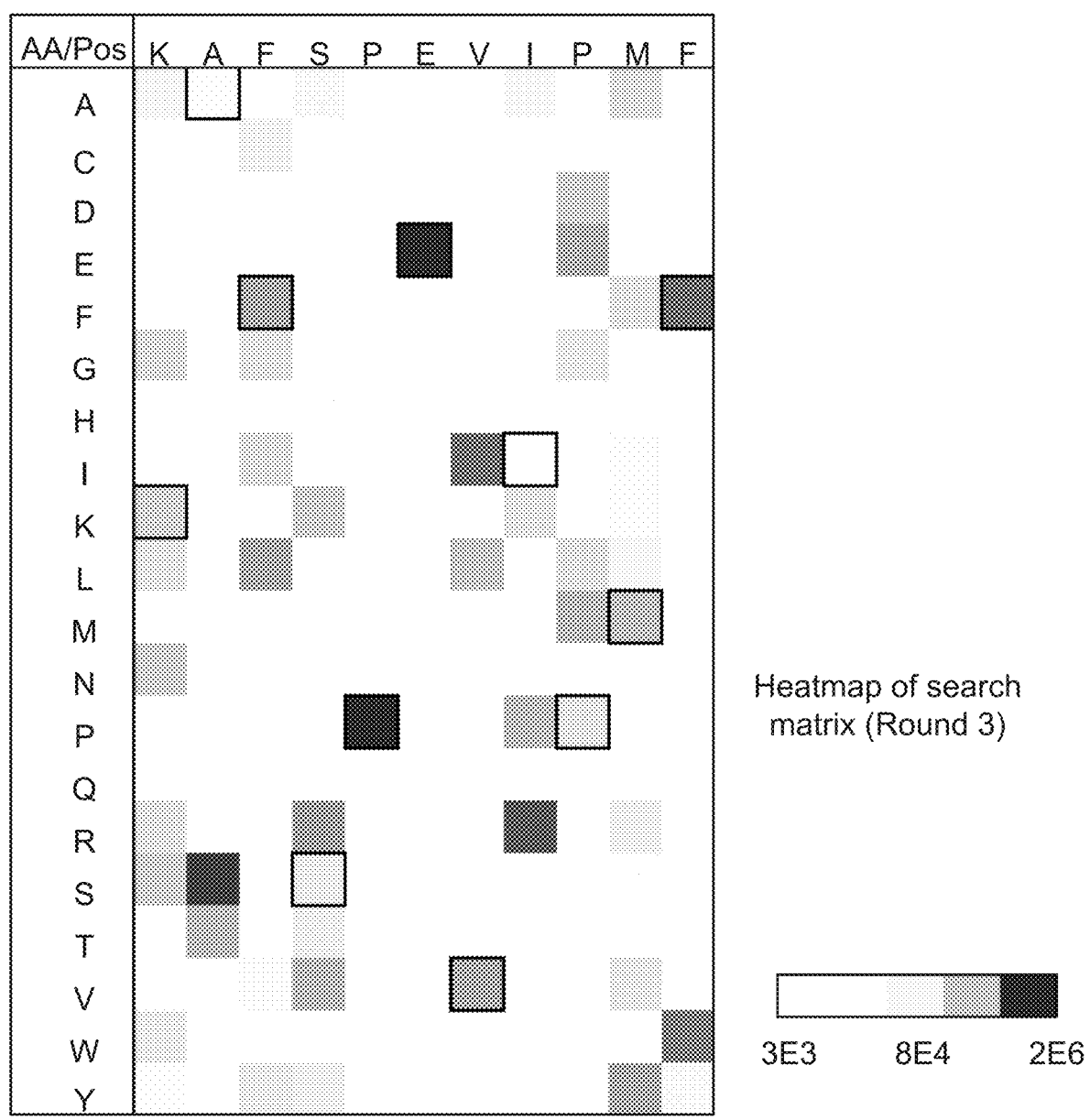
FIG. 17: shows a heatmap of the search matrix after 3 rounds of selection from the HLA-B5703 library in FIG. 16.

A library for the HLA protein B5703 was generated with the peptide ligand as shown in FIG. 16. The library was expressed and screened as described above in Example 1, with the AGA1 T cell receptor. After 3 rounds of selection, a heatmap of the search matrix from high throughput sequencing was generated, shown in FIG. 17.

The top 20 peptides after round 3 has the sequences shown below in Table 3. The number of times the peptides were represented after selection is shown in each column.

| Library Peptide | Naïve | Rd1 | Rd2 | Rd3 | Rd4 |
|---|---|---|---|---|---|
| NSLKPEIPDYF | 11 | 47 | 48656 | 268475 | 171826 |
| GTIRPEIREMW | 5 | 37 | 36754 | 226381 | 113394 |
| SSGVPEVRMMF | 6 | 38 | 40422 | 215079 | 125041 |
| LSLRPEIPLFF | 5 | 74 | 63749 | 183724 | 189891 |
| KSFVPELKPAF | 2 | 36 | 37327 | 157329 | 120443 |
| WTYRPEVRGVW | 4 | 21 | 30482 | 128915 | 91015 |
| RSFYPEIREYW | 7 | 19 | 14782 | 119258 | 48648 |
| SSFSPELRMRW | 3 | 10 | 14335 | 98338 | 48729 |
| KSCTPEVREYF | 0 | 17 | 15114 | 94896 | 49796 |
| ASFSPELRMAW | 0 | 10 | 9925 | 47218 | 31919 |
| KSLAPEVRDLF | 0 | 8 | 6502 | 34865 | 22054 |
| NSVKPEIRPVW | 6 | 10 | 10086 | 33679 | 32818 |
| NSFRPEVAMKY | 6 | 7 | 6013 | 31331 | 19786 |
| KSLTPEVRGYW | 1 | 15 | 13273 | 30634 | 38231 |
| YSFKPELKEIF | 0 | 5 | 5648 | 28641 | 20312 |
| ASFRPELAEFW | 1 | 11 | 14699 | 24829 | 42208 |
| GSLAPEIRMYW | 9 | 11 | 3108 | 23178 | 10848 |

-continued

| Library Peptide | Naïve | Rd1 | Rd2 | Rd3 | Rd4 |
|---|---|---|---|---|---|
| RSFVPEIGMGF | 8 | 18 | 20370 | 22329 | 65722 |
| SALRPEIRLLW | 1 | 50 | 28840 | 21235 | 70740 |

The data was input into a search algorithm and used to define database hits of potential epitopes for the T cell receptor, shown in Table 4 and Table 5 below: TABLE 4 GAG hits

| GI number | Reference | JMBlast Score | NR Peptide | Annotations |
|---|---|---|---|---|
| 255986448 | ACU50607.1 | 8.71E-10 | KAFSPEVXXMF | 278. gag protein [Human immunodeficiency virus 1] |
| 9651280 | AAF91122.1 | 2.00E-09 | RAFSPEVLPMF | 9. gag protein, partial [Human immunodeficiency virus 1] |
| 119361821 | ABL66844.1 | 2.90E-09 | KAFSPEVLPMF | 91. gag protein [Human immunodeficiency virus 1] |
| 166917908 | ABZ03807.1 | 2.90E-09 | KAFSPEVGPMF | 190. gag protein, partial [Human immunodeficiency virus 1] |
| 45644268 | AAS72819.1 | 8.71E-09 | KAFSPEVXPMF | 41. gag protein, partial [Human immunodeficiency virus 1] |
| 269308083 | ACZ34129.1 | 2.90E-08 | KAFSPEVKPMF | 296. gag protein, partial [Human immunodeficiency virus 1] |

TABLE 5

| | | Top 20 NR database hits | | |
|---|---|---|---|---|
| GI number | % ID to KF11 GAG | NR Peptide | Closest Library Hit (>60%) | % ID to Library Peptide |
| 302335486 | 35.7 | RSLAPEVRGYW | KSLTPEVRGYW | 81.8 |
| 345792467 | 42.9 | WTSSPEIRAVF | WTSHPEIRAYF | 81.8 |
| 495145889 | 28.6 | ASSRPELALAY | ASFRPELALRY | 81.8 |
| 459942335 | 35.7 | WTSHPEIKAAF | WTSHPEIRAYF | 81.8 |
| 430749919 | 42.9 | RSLKPEVREVF | KSLTPEVREYF | 72.7 |
| 494716083 | 42.9 | ASLRPEVREAF | KSLAPEVRELF | 72.7 |
| 493030958 | 42.9 | KSLYPEIREVF | RSFYPEIREYF | 72.7 |
| 497464005 | 28.6 | LSGVPEIRERW | LSLRPEIREYW | 72.7 |
| 497193348 | 35.7 | LTIRPEIRPRW | GTIRPEIREMW | 72.7 |
| 488856804 | 42.9 | ASFKPELPDFF | NSFKPEIPDYF | 72.7 |
| 430004692 | 35.7 | STISPEIRLFW | GTISPEIREMW | 72.7 |
| 471573742 | 42.9 | ASLKPEVPLVF | LSLRPEVPLFF | 72.7 |
| 495156089 | 42.9 | SSGAPEVRELF | SSGVPEVRMMF | 72.7 |
| 301092772 | 35.7 | SSVVPELPMAF | SSVVPEVRMMF | 72.7 |
| 348664816 | 42.9 | RSFYPELRLLF | RSFYPEIREYF | 72.7 |
| 497177556 | 50.0 | LTISPEIPPYF | GTIRPEIPDYF | 72.7 |

TABLE 5-continued

Top 20 NR database hits

| GI number | % ID to KF11 GAG | NR Peptide | Closest Library Hit (>60%) | % ID to Library Peptide |
|---|---|---|---|---|
| 497797312 | 42.9 | ESFRPEIRQYF | RSFYPEIREYF | 72.7 |
| 448510490 | 50.0 | GSLSPELRPIF | LSGSPELRMIF | 72.7 |
| 15790131 | 35.7 | STLSPELRGRW | SSFSPELRMRW | 72.7 |
| 313682157 | 42.9 | KSFRPELKEFY | ASFRPELAEFW | 72.7 |

---

What is claimed is:

1. A cell surface library of ligands for a T cell receptor (TCR),
   wherein the library comprises single chain polypeptides displayed on a surface of a host cell, the single chain polypeptides each comprising (a) a peptide ligand and (b) a binding domain of an MHC protein; and
   wherein the binding domain of the MHC protein comprises (i) a soluble domain of a class II MHC α and β chain or (ii) a soluble form of an α domain of a class I MHC protein and a soluble form of β2 microglobulin,
   wherein the host cells are yeast cells, and
   wherein the single chain polypeptides each have a structure of P-$L_1$-β-$L_2$-α-$L_3$-T, wherein
   P is the peptide ligand;
   $L_1$, $L_2$ and $L_3$ are flexible linkers, wherein each of $L_1$, $L_2$ and $L_3$ is about 4 to about 12 amino acids in length;
   α is a soluble form of an α domain of a human class I MHC protein or a soluble form of a human class II MHC protein;
   β is a soluble form of human class I MHC β2 microglobulin or a soluble form of a β domain of a human class II MHC β protein;
   when α is the soluble form of an α domain of a human class I MHC protein, then β is the soluble form of human class I MHC β2 microglobulin, wherein the binding domains are HLA-A2 alpha 1 and alpha 2 domains, comprising the amino acid change {Y84A};
   when α is the soluble form of an α domain of a human class II MHC protein, then β is the soluble form of a β domain of a human class II MHC β protein, wherein the binding domains are HLA-DR4α comprising the set of amino acid changes {M36L, V132M} and HLA-DR4β comprising the set of amino acid changes {H62N, D72E}; and
   T is a domain that tethers the single chain polypeptide to the surface of a host cell in the population of host cells.

2. The library of claim 1, wherein the MHC binding domain comprises α1 and α2 domains of a class I MHC α protein, and β2 microglobulin.

3. The library of claim 1, wherein the MHC binding domain comprises α1 and β1 domains of a class II MHC protein.

4. The method of claim 1 wherein the TCR is multimerized or is an orphan TCR.

5. The library of claim 1, wherein the peptide ligand is from about 8 to about 20 amino acids in length.

6. The library of claim 1, wherein the peptide ligand is randomized at multiple positions, and wherein the peptide ligand has limited diversity at MHC anchor positions.

7. The library of claim 1, wherein the library is created in cells using homologous recombination.

8. The library of claim 1, wherein the cell library comprises at least $10^6$ diverse single chain polypeptides.

9. The library of claim 1, wherein the T is Aga2.

10. The library of claim 1, wherein the flexible linkers are Gly-Ser linkers.

11. The library of claim 1, wherein the peptide ligand is from about 8 to about 20 amino acids in length and is randomized at multiple positions and has limited diversity at an MHC anchor position.

12. The library of claim 1, wherein
    the peptide ligand is from about 8 to about 20 amino acids in length and is randomized at multiple positions and has limited diversity at MHC anchor positions;
    the α is a soluble form of an α domain of a human class I MHC protein comprising α1 and α2 domains of the human class I MHC protein;
    the β is a soluble form of human class I MHC β2 microglobulin;
    the T is Aga2; and
    the host cells are yeast cells.

13. The library of claim 1, wherein
    the peptide ligand is from about 8 to about 20 amino acids in length and is randomized at multiple positions and has limited diversity at MHC anchor positions;
    the α is a soluble form of an α domain of a human class II MHC protein;
    the β is a soluble form of a human class II MHC β protein;
    the T is Aga2; and
    the host cells are yeast cells.

14. Nucleic acids encoding the single chain polypeptides of the cell surface library of claim 1.

15. A cell expressing the library of claim 1 the cell surface.

* * * * *